(12) United States Patent
Vale et al.

(10) Patent No.: US 11,547,427 B2
(45) Date of Patent: Jan. 10, 2023

(54) CLOT RETRIEVAL DEVICES

(71) Applicant: NEURAVI LIMITED, Galway (IE)

(72) Inventors: David Vale, Galway (IE); Michael Gilvarry, Galway (IE); Eamon Brady, Galway (IE); Mahmood Razavi, Irvine, CA (US)

(73) Assignee: NEURAVI LIMITED, Galway (IE)

( * ) Notice: Subject to any disclaimer, the term of this patent is extended or adjusted under 35 U.S.C. 154(b) by 680 days.

(21) Appl. No.: 16/544,423

(22) Filed: Aug. 19, 2019

(65) Prior Publication Data

US 2019/0365399 A1 Dec. 5, 2019

Related U.S. Application Data

(63) Continuation of application No. 15/226,389, filed on Aug. 2, 2016, now Pat. No. 10,420,570, which is a
(Continued)

(51) Int. Cl.
*A61B 17/221* (2006.01)
*A61B 17/22* (2006.01)

(52) U.S. Cl.
CPC .... *A61B 17/221* (2013.01); *A61B 2017/2215* (2013.01); *A61B 2017/22034* (2013.01);
(Continued)

(58) Field of Classification Search
CPC ........ A61B 17/22031; A61B 17/22032; A61B 17/221; A61B 2017/11061; A61B 2017/22034; A61B 2017/22035; A61B 2017/22094; A61B 2017/2212; A61B 2017/2215; A61B 2017/2217; A61B 2002/826; A61B 2002/9155
See application file for complete search history.

(56) References Cited

U.S. PATENT DOCUMENTS 4,455,717 A 6/1984 Gray
4,611,594 A 9/1986 Grayhack et al.
(Continued)

FOREIGN PATENT DOCUMENTS

CN 2557083 Y 6/2003
CN 101172051 A 5/2008
(Continued)

OTHER PUBLICATIONS

US 6,348,062 B1, 02/2002, Hopkins (withdrawn)

*Primary Examiner* — Martin T Ton
(74) *Attorney, Agent, or Firm* — Troutman Pepper Hamilton Sanders LLP

(57) ABSTRACT

A clot retrieval device for removing clot from a blood vessel including a plurality of ring elements comprising a plurality of struts forming one or more closed cells having one or more crown elements and attached together by connecting tethers at connection points, a plurality of openings through which clot may pass and enter the device, each opening being disposed between respective ring elements. Each ring element can be self-expandable from a collapsed configuration to an expanded configuration wherein a radial force biases the ring elements toward the expanded configuration. At least one of the crown element terminates in an apex away from a center axis of the device.

22 Claims, 61 Drawing Sheets

Related U.S. Application Data continuation of application No. 13/829,684, filed on Mar. 14, 2013, now Pat. No. 9,433,429.

(52) U.S. Cl.
CPC ............. *A61B 2017/22061* (2013.01); *A61B 2017/22094* (2013.01)

(56) References Cited

U.S. PATENT DOCUMENTS

| | | |
|---|---|---|
| 4,612,931 A | 9/1986 | Dormia |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | MacGregor et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A * | 1/1995 | Nadal .................. A61F 2/01 606/198 |
| 5,387,219 A | 2/1995 | Rappe |
| 5,387,226 A | 2/1995 | Miraki |
| 5,449,372 A | 9/1995 | Schmaltz |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates |
| 5,665,117 A | 9/1997 | Rhodes |
| 5,695,519 A | 12/1997 | Summer et al. |
| 5,709,704 A | 1/1998 | Nott et al. |
| 5,713,853 A | 2/1998 | Clark |
| 5,769,871 A | 6/1998 | Mers Kelly |
| 5,769,884 A | 6/1998 | Solovay |
| 5,779,686 A | 7/1998 | Sato et al. |
| 5,779,716 A | 7/1998 | Cano |
| 5,800,519 A | 9/1998 | Sandock |
| 5,810,874 A | 9/1998 | Lefebvre |
| 5,814,064 A | 9/1998 | Daniel et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,221,096 B1 * | 4/2001 | Aiba .................. A61F 2/86 606/108 |
| 6,231,597 B1 | 5/2001 | Deem et al. |
| 6,238,412 B1 | 5/2001 | Dubrul |
| 6,245,012 B1 | 6/2001 | Kleshinski |
| 6,245,087 B1 | 6/2001 | Addis |
| 6,251,122 B1 | 6/2001 | Tsu Kernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz et al. |
| 6,355,057 B1 | 3/2002 | DeMarais et al. |
| 6,361,545 B1 | 3/2002 | Macoviak |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,488,701 B1 | 12/2002 | Nolting et al. |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack |
| 6,602,265 B2 | 8/2003 | Dubrul et al. |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |

(56) References Cited

U.S. PATENT DOCUMENTS

| | | |
|---|---|---|
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,695,858 B1 | 2/2004 | Dubrul et al. |
| 6,702,782 B2 | 3/2004 | Miller |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukemik |
| 7,041,116 B2 | 5/2006 | Goto |
| 7,048,758 B2 | 5/2006 | Boyle |
| 7,052,500 B2 | 5/2006 | Bashiri et al. |
| 7,058,456 B2 | 6/2006 | Pierce |
| 7,063,707 B2 | 6/2006 | Bose |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Malaei |
| 7,179,273 B1 | 2/2007 | Palmer et al. |
| 7,185,922 B2 | 3/2007 | Takayanagi et al. |
| 7,220,271 B2 | 5/2007 | Clubb |
| 7,226,464 B2 | 6/2007 | Garner et al. |
| 7,229,472 B2 | 6/2007 | DePalma et al. |
| 7,241,304 B2 | 7/2007 | Boyle et al. |
| 7,288,112 B2 | 10/2007 | Denardo et al. |
| 7,300,458 B2 | 11/2007 | Henkes et al. |
| 7,306,618 B2 | 12/2007 | Demond |
| 7,314,483 B2 | 1/2008 | Landau et al. |
| 7,316,692 B2 | 1/2008 | Huffmaster |
| 7,323,001 B2 | 1/2008 | Clubb |
| 7,331,976 B2 | 2/2008 | McGuckin, Jr. et al. |
| 7,344,550 B2 | 3/2008 | Garrison et al. |
| 7,399,308 B2 | 7/2008 | Borillo et al. |
| 7,410,491 B2 | 8/2008 | Hopkins |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,604,650 B2 | 10/2009 | Bergheim |
| 7,618,434 B2 | 11/2009 | Santra |
| 7,662,165 B2 | 2/2010 | Gilson et al. |
| 7,670,356 B2 | 3/2010 | Mazzocchi |
| 7,678,123 B2 | 3/2010 | Chanduszko |
| 7,691,121 B2 | 4/2010 | Rosenbluth |
| 7,691,124 B2 | 4/2010 | Balgobin |
| 7,708,770 B2 | 5/2010 | Linder |
| 7,717,929 B2 | 5/2010 | Fallman |
| 7,736,385 B2 | 6/2010 | Agnew |
| 7,758,606 B2 | 7/2010 | Streeter et al. |
| 7,758,611 B2 | 7/2010 | Kato |
| 7,766,934 B2 | 8/2010 | Pal |
| 7,771,452 B2 | 8/2010 | Pal |
| 7,780,694 B2 | 8/2010 | Palmer |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,176 B2 | 11/2010 | Mazzocchi |
| 7,846,175 B2 | 12/2010 | Bonnette et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Garrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |

(56) References Cited

U.S. PATENT DOCUMENTS

| | | |
|---|---|---|
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolick et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,221,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,617,435 B2 | 4/2020 | Vale et al. |
| 10,722,257 B2 | 7/2020 | Skillrud et al. |
| 2001/0001315 A1 | 5/2001 | Bates |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0049554 A1 | 12/2001 | Ruiz et al. |
| 2001/0051810 A1 | 12/2001 | Dubrul |
| 2002/0004667 A1 | 1/2002 | Adams et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0042627 A1 | 4/2002 | Brady et al. |
| 2002/0049468 A1 | 4/2002 | Streeter |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0138094 A1 | 9/2002 | Borillo |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans |
| 2002/0188314 A1 | 12/2002 | Anderson et al. |

(56) References Cited

U.S. PATENT DOCUMENTS

| | | |
|---|---|---|
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest |
| 2003/0004540 A1 | 1/2003 | Linder et al. |
| 2003/0004542 A1 | 1/2003 | Wensel |
| 2003/0009146 A1 | 1/2003 | Muni |
| 2003/0009191 A1 | 1/2003 | Wensel |
| 2003/0038447 A1 | 2/2003 | Cantele |
| 2003/0040772 A1 | 2/2003 | Hyodoh et al. |
| 2003/0050663 A1 | 3/2003 | Khachin |
| 2003/0064151 A1 | 4/2003 | Klinedinst |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0208224 A1 | 11/2003 | Broome |
| 2003/0212430 A1 | 11/2003 | Bose |
| 2003/0236533 A1 | 12/2003 | Wlson |
| 2004/0064179 A1 | 4/2004 | Linder et al. |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland |
| 2004/0133232 A1 | 7/2004 | Rosenbluth et al. |
| 2004/0138692 A1 | 7/2004 | Phung |
| 2004/0153117 A1 | 8/2004 | Clubb et al. |
| 2004/0153118 A1 | 8/2004 | Clubb |
| 2004/0199201 A1 | 10/2004 | Kellett et al. |
| 2004/0215318 A1 | 10/2004 | Kwitkin |
| 2004/0220663 A1 | 11/2004 | Rivelli, Jr. |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090779 A1 | 4/2005 | Osypka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0192627 A1 | 9/2005 | Whisenant et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0069424 A1* | 3/2006 | Acosta ............... A61F 2/91 623/1.12 |
| 2006/0074477 A1 | 4/2006 | Berthiaume |
| 2006/0149313 A1 | 7/2006 | Arguello et al. |
| 2006/0155305 A1 | 7/2006 | Freudenthal |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1* | 4/2007 | Pal ............... A61F 2/012 606/200 |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslayski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097386 A1 | 4/2008 | Osypka |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0125798 A1 | 5/2008 | Osborne et al. |
| 2008/0177296 A1 | 7/2008 | Sepetka |
| 2008/0178890 A1 | 7/2008 | Townsend et al. |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188887 A1 | 8/2008 | Batiste |
| 2008/0200946 A1 | 8/2008 | Braun |
| 2008/0200947 A1 | 8/2008 | Kusleika et al. |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262410 A1 | 10/2008 | Jenson et al. |
| 2008/0262528 A1 | 10/2008 | Martin |
| 2008/0262532 A1 | 10/2008 | Martin |
| 2008/0269871 A1 | 10/2008 | Eli |
| 2008/0275488 A1* | 11/2008 | Fleming ............... A61F 2/01 606/200 |

(56) References Cited

U.S. PATENT DOCUMENTS

| | | |
|---|---|---|
| 2008/0275493 A1 | 11/2008 | Farmiga |
| 2008/0281350 A1 | 11/2008 | Sepetka et al. |
| 2008/0312681 A1 | 12/2008 | Ansel |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson |
| 2009/0105737 A1 | 4/2009 | Fulkerson |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0292297 A1 | 11/2009 | Ferrere |
| 2009/0292307 A1 | 11/2009 | Razack |
| 2009/0299393 A1 | 12/2009 | Martin |
| 2009/0299403 A1 | 12/2009 | Chanduszko et al. |
| 2009/0306702 A1 | 12/2009 | Miloslavski |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnett et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054514 A1 | 3/2011 | Arcand |
| 2011/0054516 A1 | 3/2011 | Keegan |
| 2011/0060212 A1 | 3/2011 | Slee et al. |
| 2011/0060359 A1 | 3/2011 | Hannes |
| 2011/0054504 A1 | 5/2011 | Wolf et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2011/0319917 A1 | 12/2011 | Ferrera et al. |
| 2012/0022572 A1 | 1/2012 | Braun et al. |
| 2012/0041449 A1 | 2/2012 | Eckhouse et al. |
| 2012/0041474 A1 | 2/2012 | Eckhouse et al. |
| 2012/0059356 A1 | 3/2012 | diPalma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0123466 A1 | 5/2012 | Porter et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslayski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0366650 A1 | 12/2015 | Zi et al. |

(56) References Cited

U.S. PATENT DOCUMENTS

| | | |
|---|---|---|
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |

FOREIGN PATENT DOCUMENTS

| | | | |
|---|---|---|---|
| CN | 102307613 A | 1/2012 | |
| CN | 102596098 A | 7/2012 | |
| CN | 103764049 A | 4/2014 | |
| CN | 104042304 A | 9/2014 | |
| CN | 105208950 A | 12/2015 | |
| CN | 105662532 A | 6/2016 | |
| CN | 205359559 U | 7/2016 | |
| CN | 107530090 A | 1/2018 | |
| CN | 208582467 U | 3/2019 | |
| DE | 202009001951 U1 | 4/2010 | |
| DE | 102009056450 | 6/2011 | |
| DE | 102010010849 | 9/2011 | |
| DE | 10 2010 014778 A1 | 10/2011 | |
| DE | 102010024085 | 12/2011 | |
| DE | 102011014586 B3 | 9/2012 | |
| EP | 1153581 A1 * | 11/2001 | ............... A61F 2/82 |
| EP | 2301450 B1 | 11/2011 | |
| EP | 2438891 A1 | 4/2012 | |
| EP | 2628455 A1 | 8/2013 | |
| EP | 3156004 A | 4/2017 | |
| GB | 2427554 A | 1/2007 | |
| GB | 2494820 A | 3/2013 | |
| JP | 0919438 A1 | 1/1997 | |
| JP | 2014-511223 A | 5/2014 | |
| JP | 2014-525796 A | 10/2014 | |
| JP | 2015-505250 A | 2/2015 | |
| JP | 2016-513505 A | 5/2016 | |

(56) References Cited

FOREIGN PATENT DOCUMENTS

| | | |
|---|---|---|
| JP | 2019-526365 A | 9/2019 |
| WO | WO 94/24926 | 11/1994 |
| WO | WO 97/27808 | 8/1997 |
| WO | WO 97/38631 A1 | 10/1997 |
| WO | WO 99/20335 | 4/1999 |
| WO | WO 99/60933 | 12/1999 |
| WO | WO 99/56801 | 4/2000 |
| WO | WO 01/21077 | 3/2001 |
| WO | WO 2004/056275 A1 | 7/2001 |
| WO | WO 02/02162 | 1/2002 |
| WO | WO 02/11627 | 2/2002 |
| WO | WO 02/43616 | 6/2002 |
| WO | WO 02/070061 | 9/2002 |
| WO | WO 02/094111 | 11/2002 |
| WO | WO 03/002006 | 1/2003 |
| WO | WO 03/030751 | 4/2003 |
| WO | WO 03/051448 | 6/2003 |
| WO | WO 2004/028571 A2 | 4/2004 |
| WO | WO 2005/000130 A1 | 1/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2006/135823 A2 | 12/2006 |
| WO | WO 2007/054307 | 5/2007 |
| WO | WO 2007/068424 | 6/2007 |
| WO | WO 2008/034615 | 3/2008 |
| WO | WO 2008/051431 A1 | 5/2008 |
| WO | WO 2008/131116 | 10/2008 |
| WO | WO 2008/135823 A1 | 11/2008 |
| WO | WO 2009/031338 A1 | 3/2009 |
| WO | WO 2009/076482 | 6/2009 |
| WO | WO 2009/086482 | 7/2009 |
| WO | WO 2009/105710 A1 | 8/2009 |
| WO | WO 2010/010545 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/120490 A2 | 9/2012 |
| WO | WO 2012/110619 A9 | 10/2012 |
| WO | WO 2012/156924 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 | 12/2015 |
| WO | WO 2016/010995 A1 | 1/2016 |
| WO | WO 2016/089451 A1 | 6/2016 |
| WO | 2017/103686 A2 | 6/2017 |
| WO | WO 2017/089424 A1 | 6/2017 |
| WO | WO 2017/161204 A1 | 9/2017 |
| WO | WO 2020/039082 A1 | 2/2020 |
| WO | WO 2021/113302 A1 | 6/2021 |

* cited by examiner

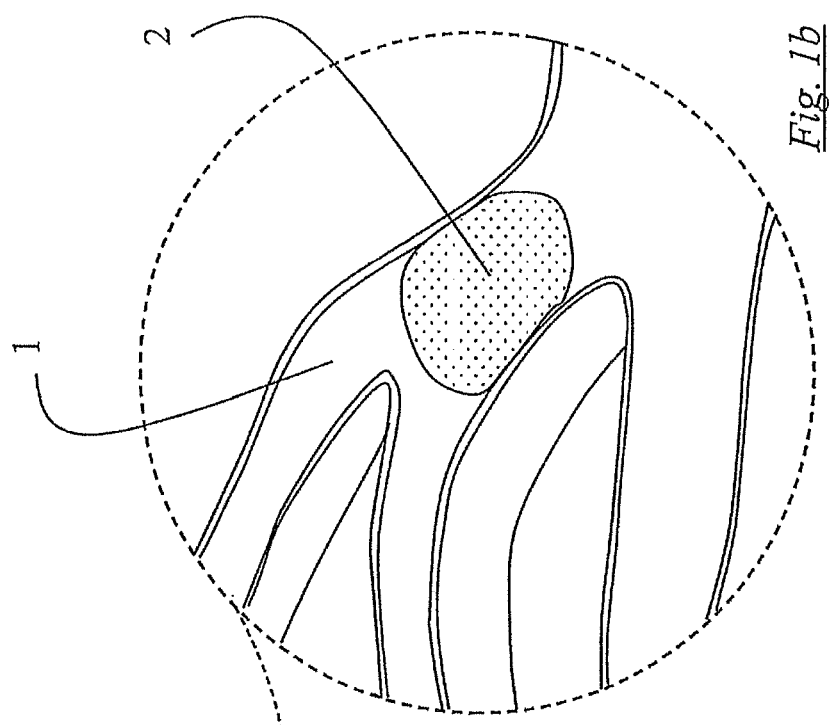
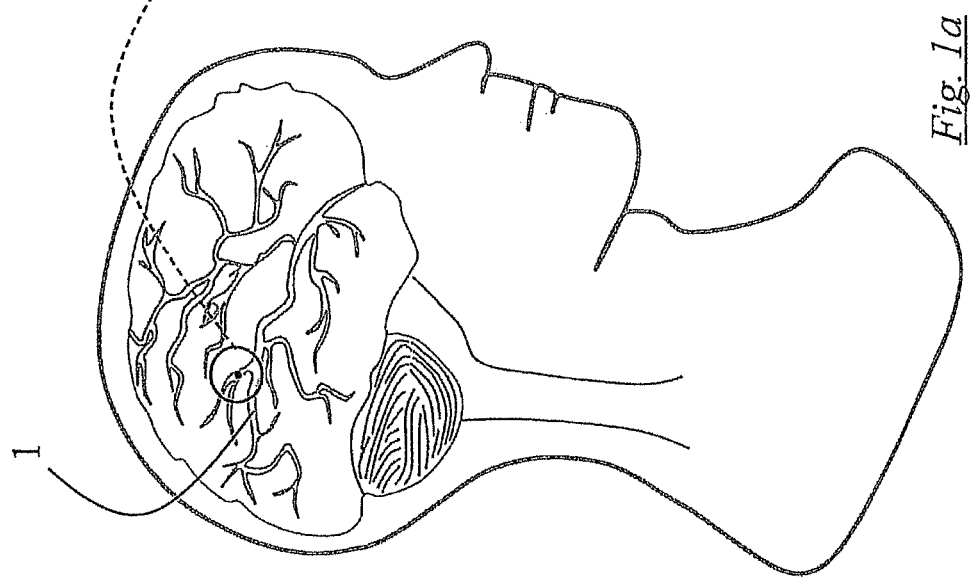
Fig. 1a
Fig. 1b

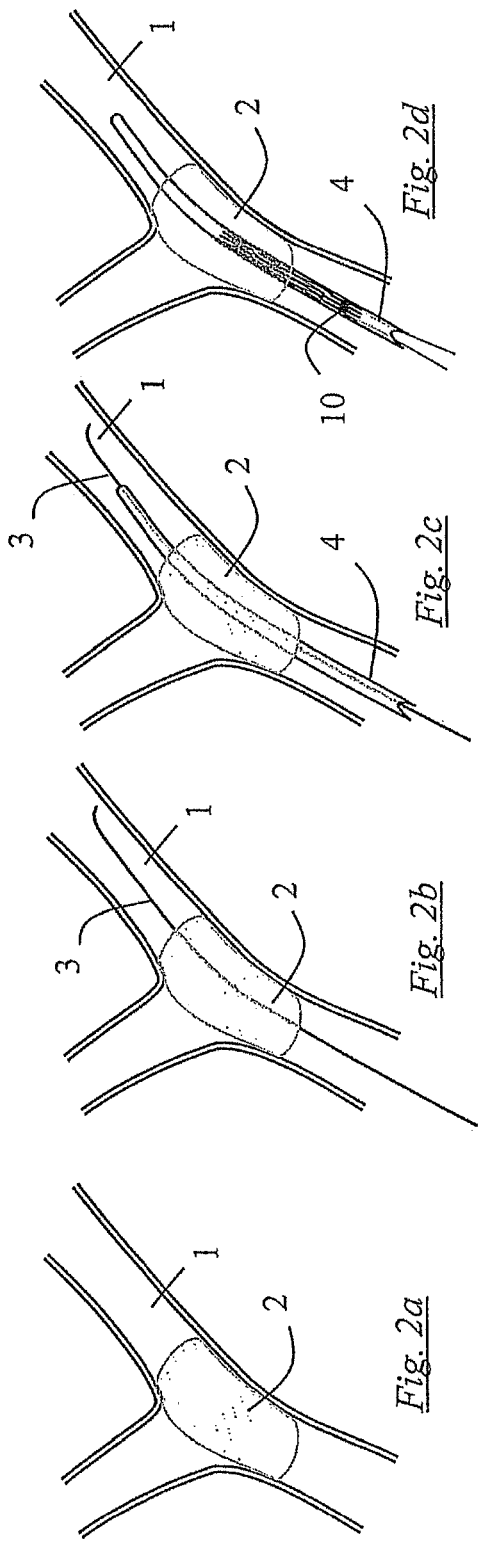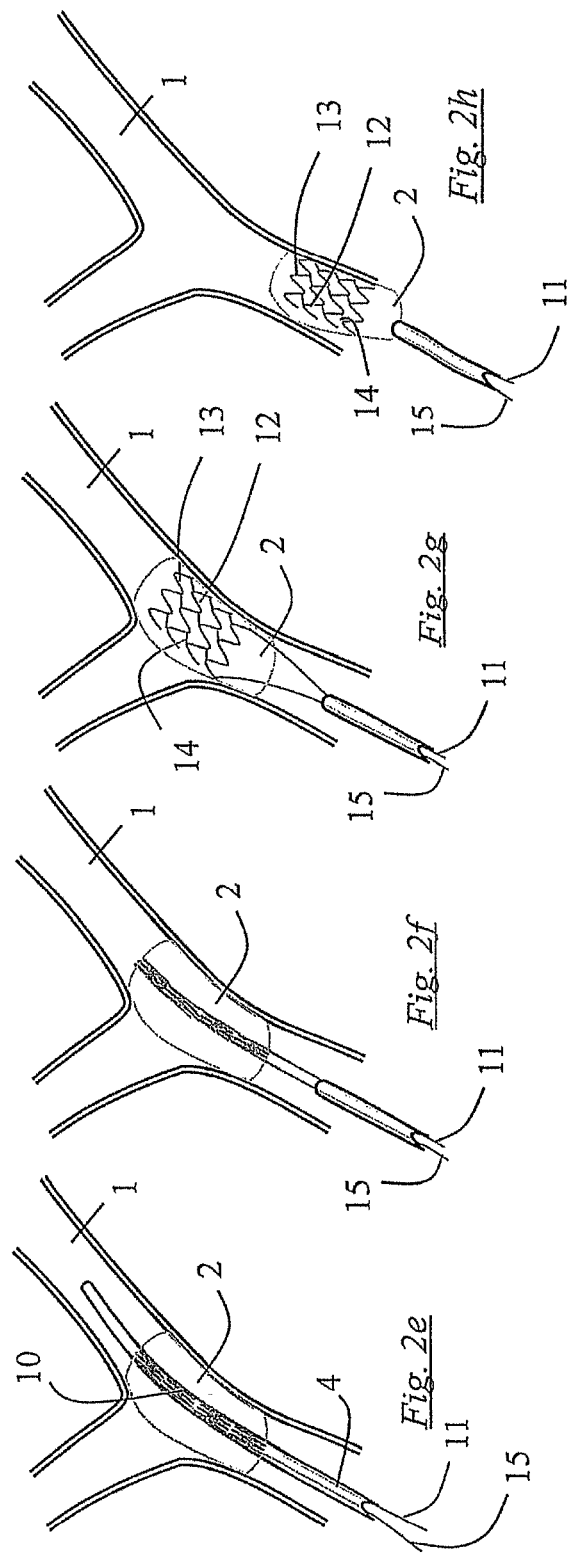

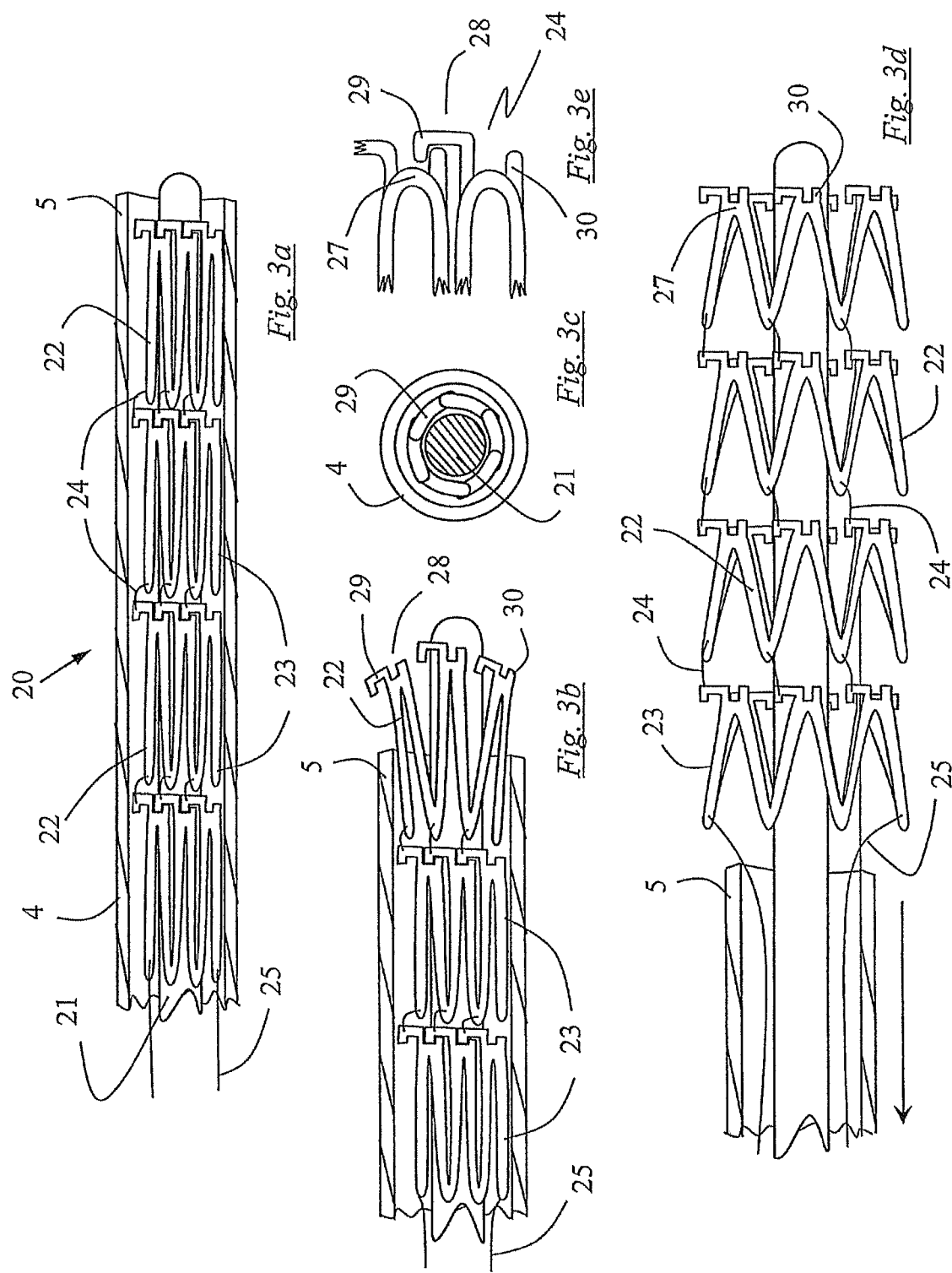

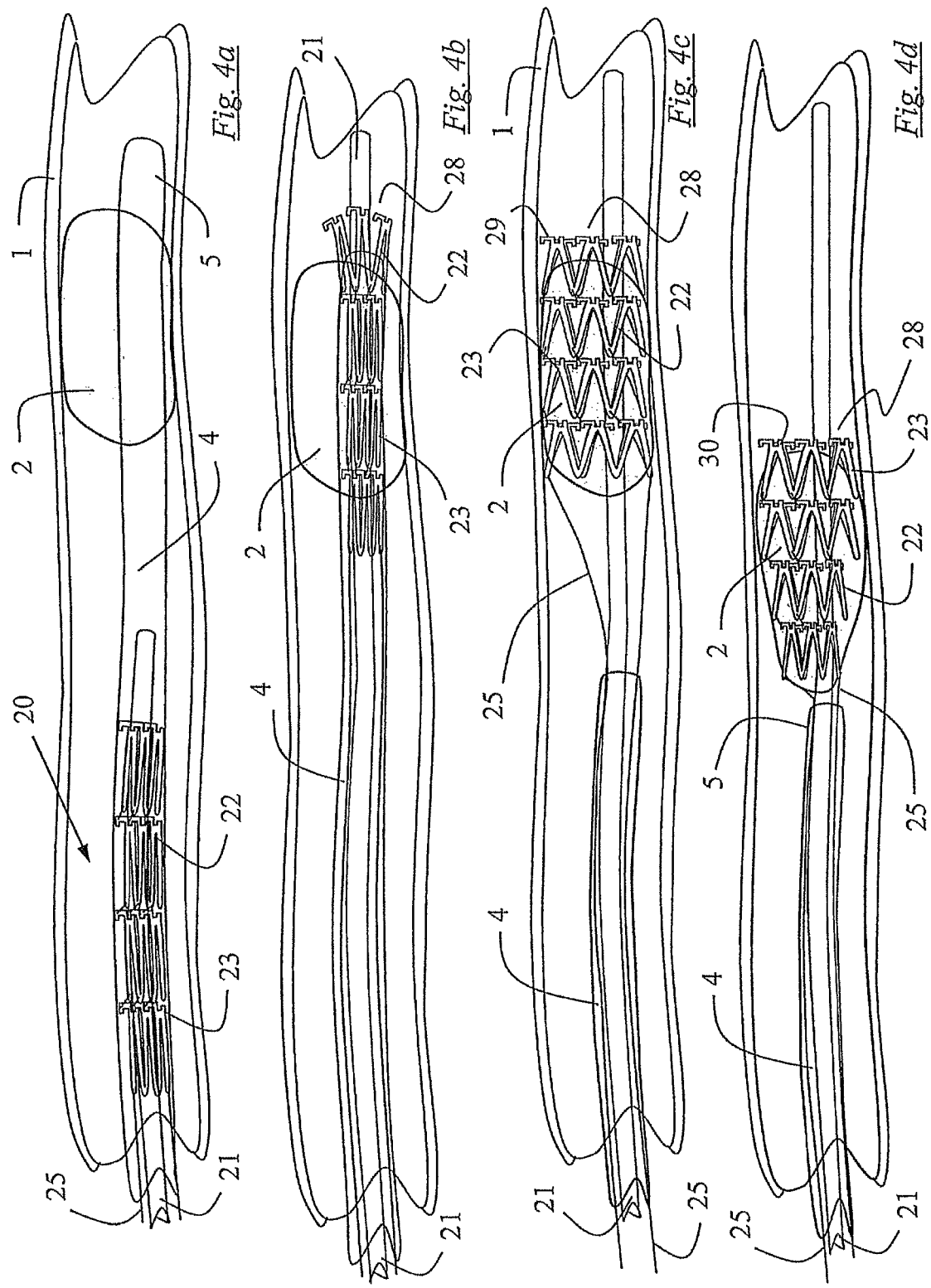

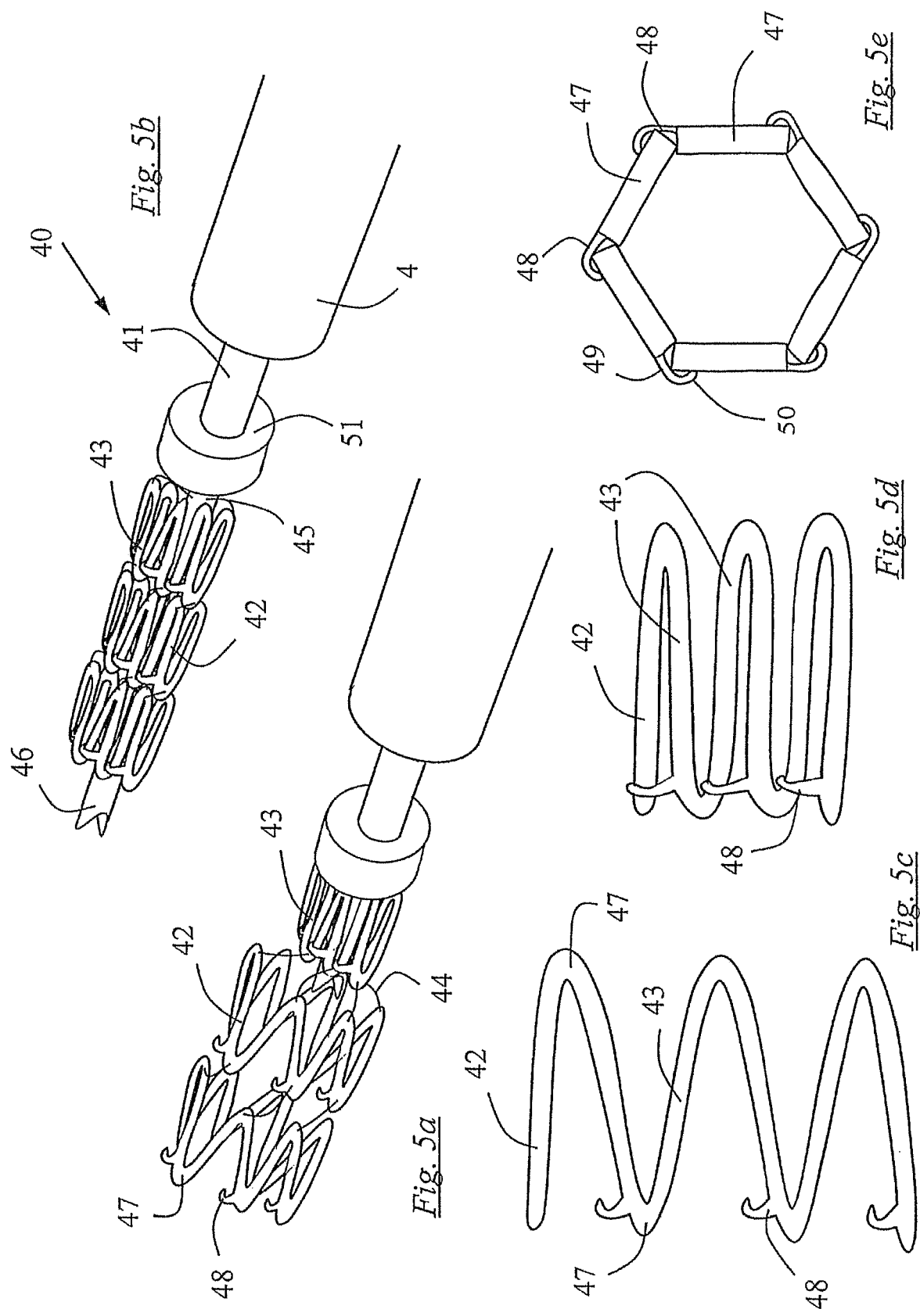

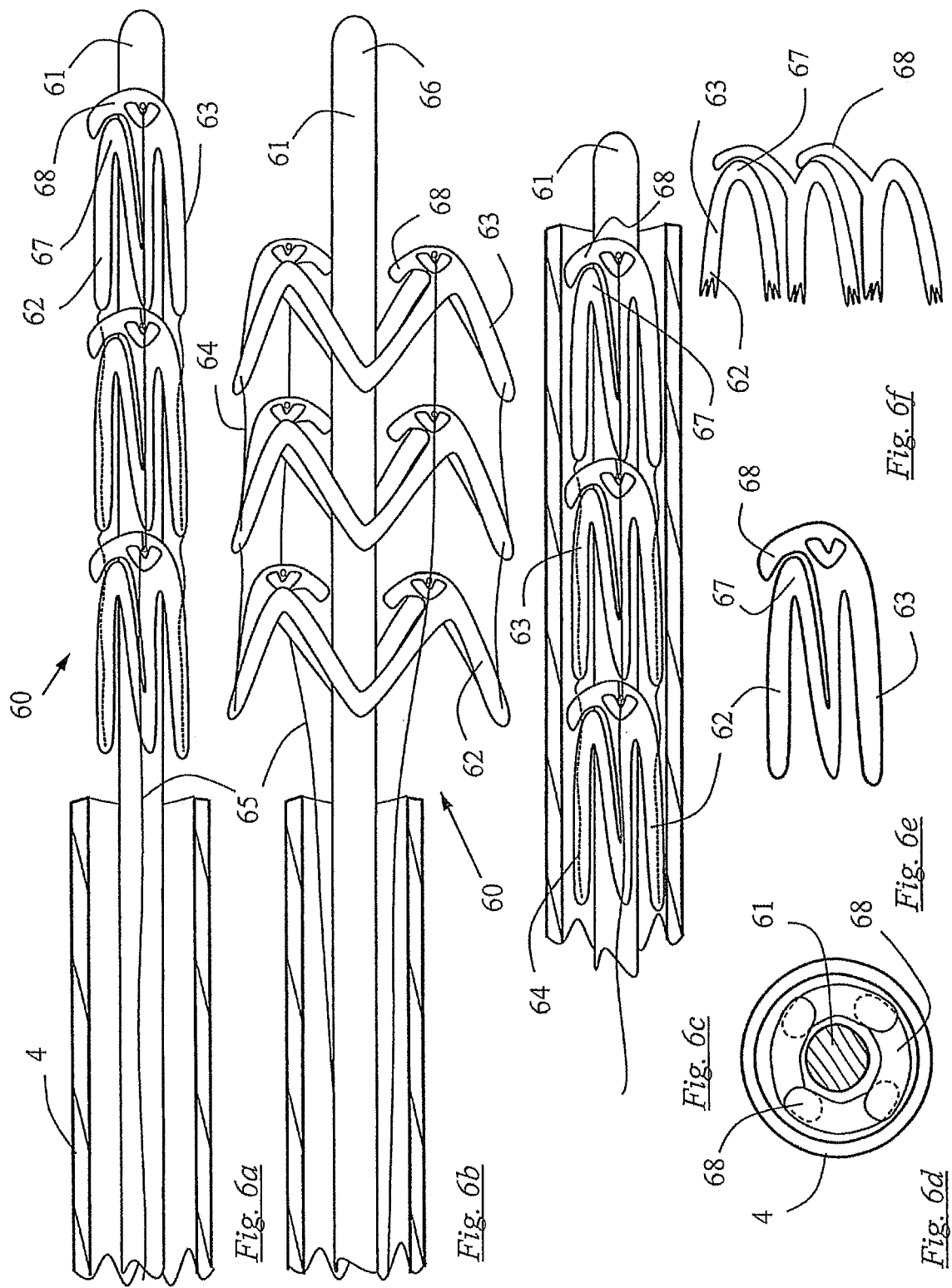

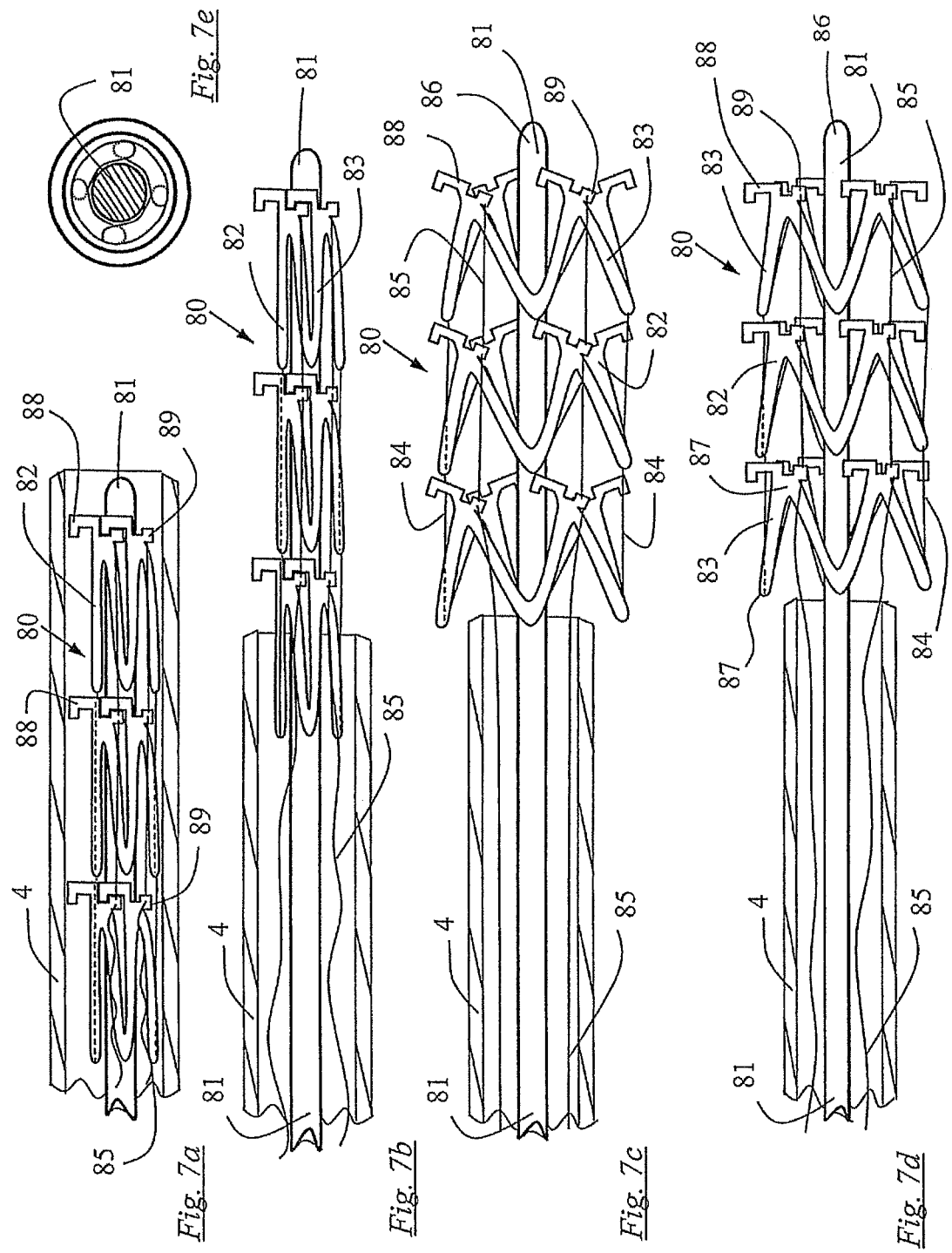

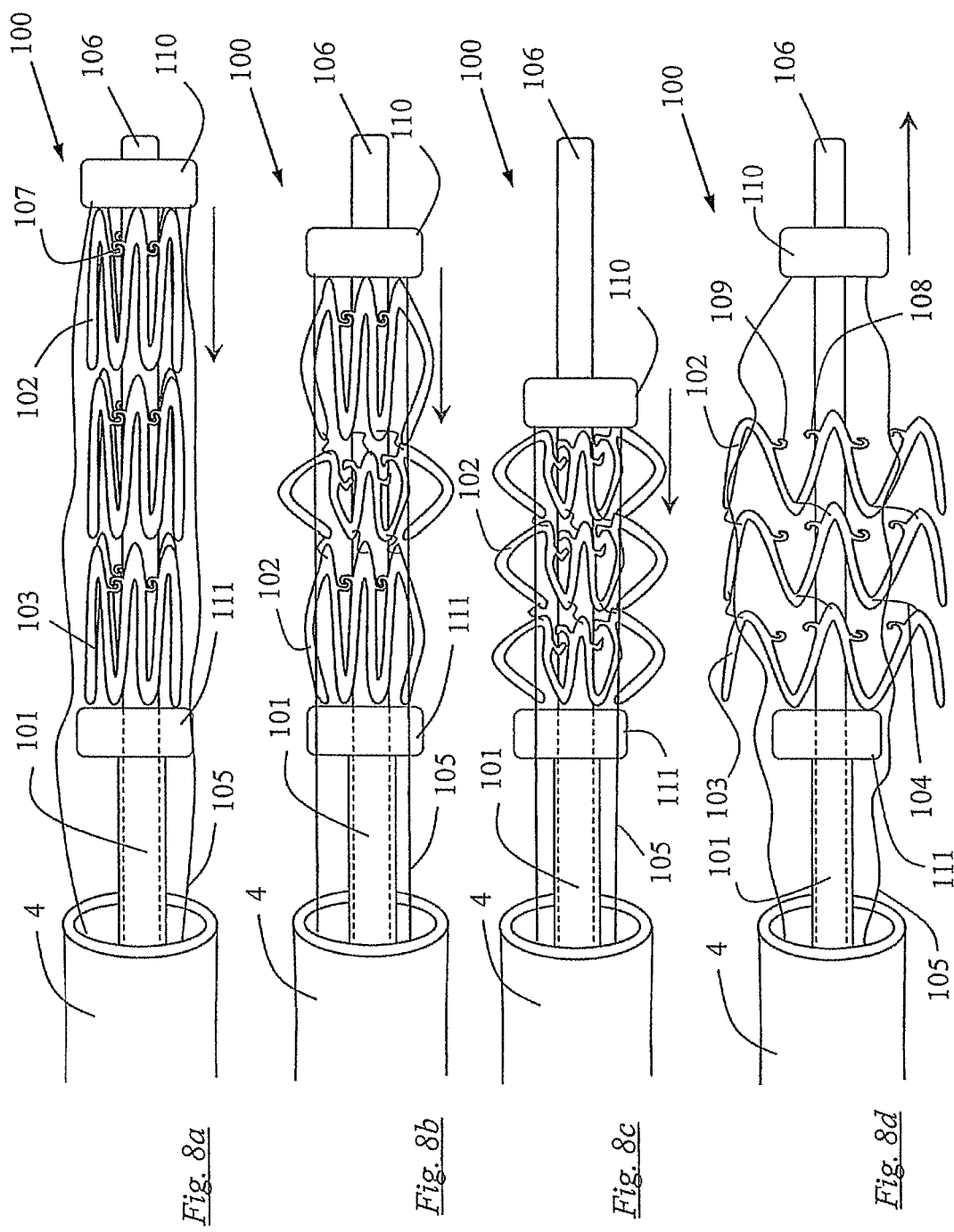

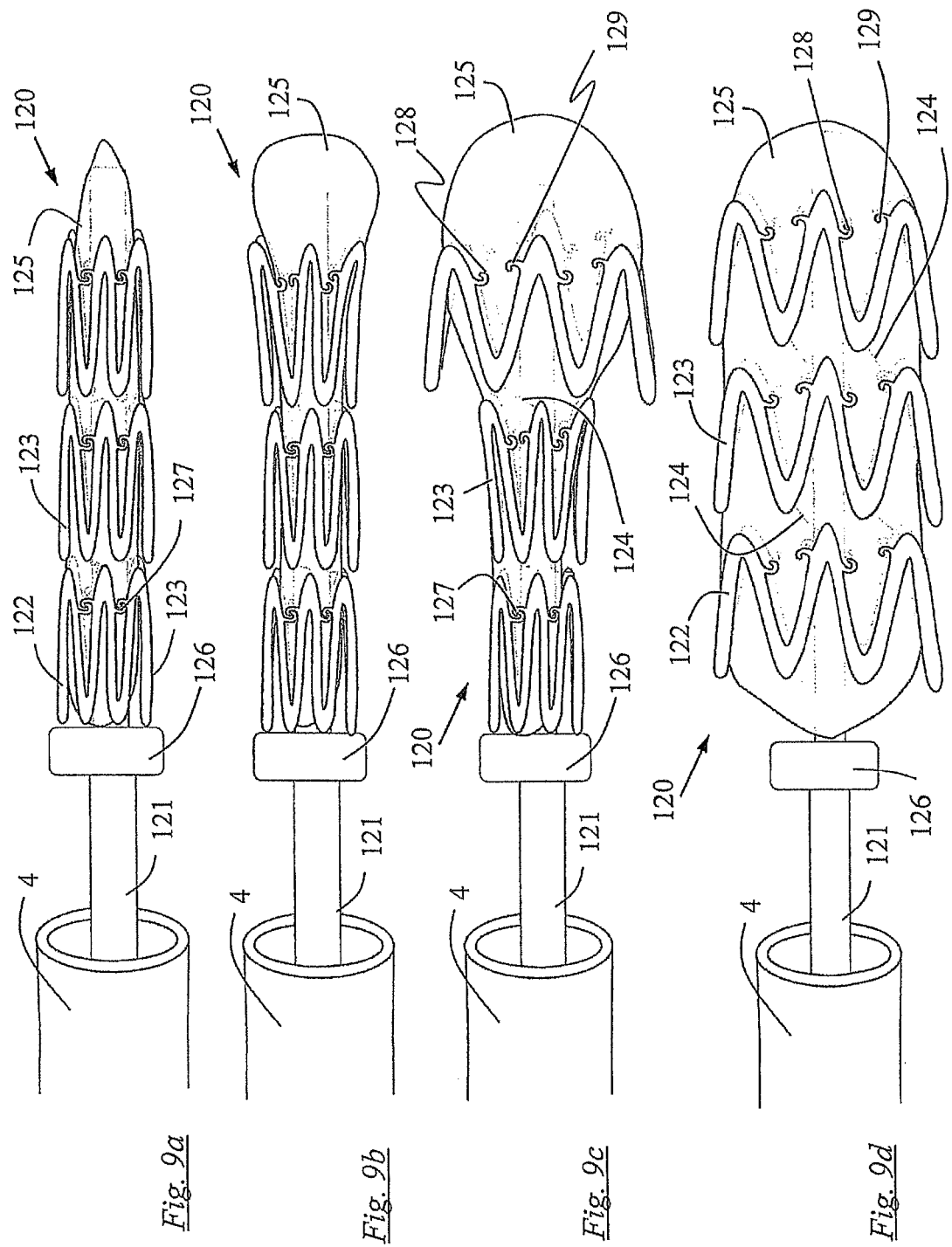

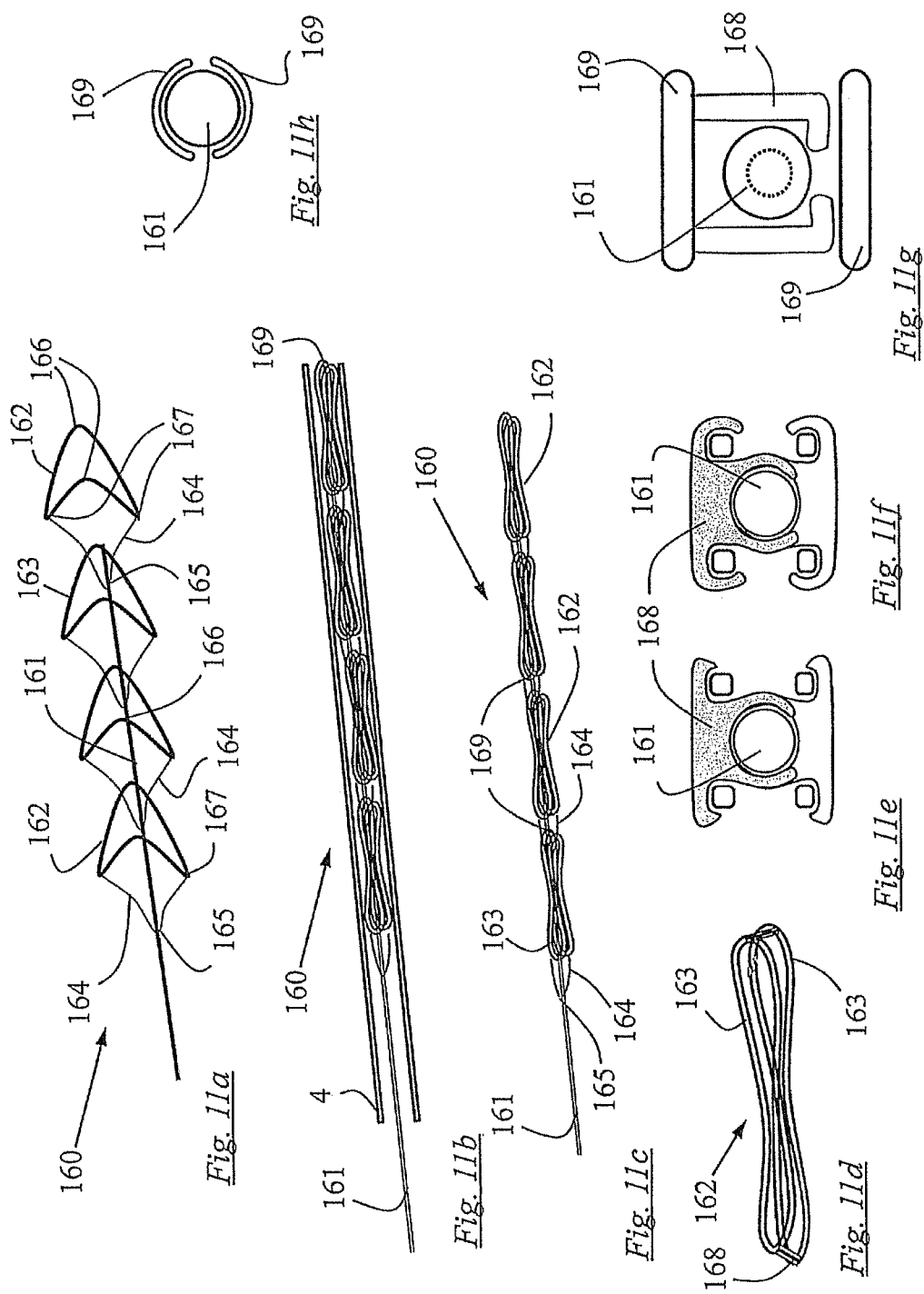

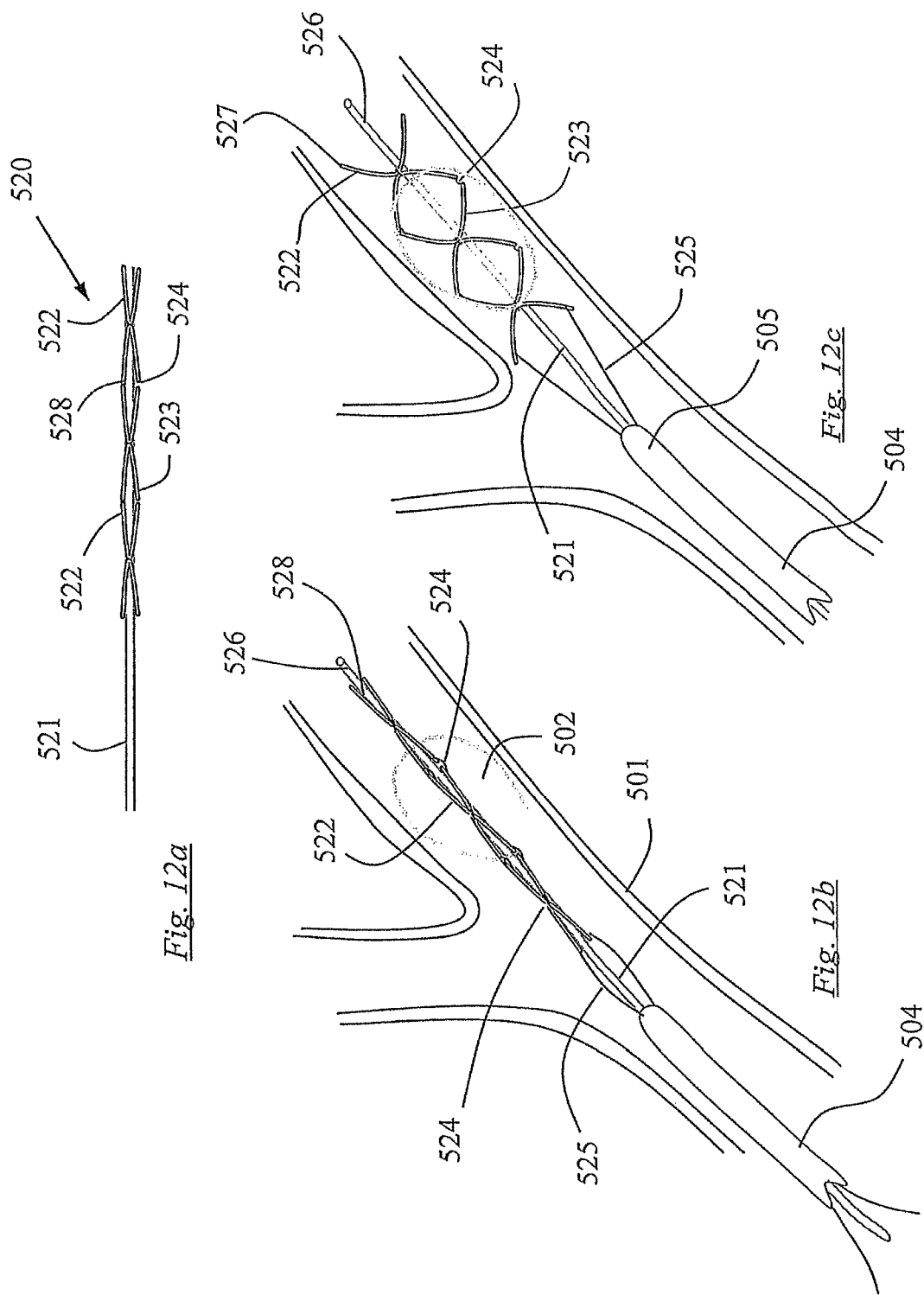

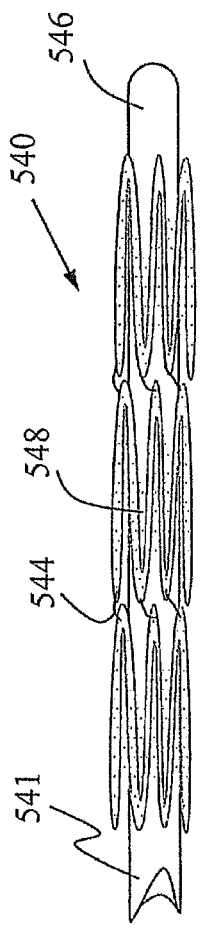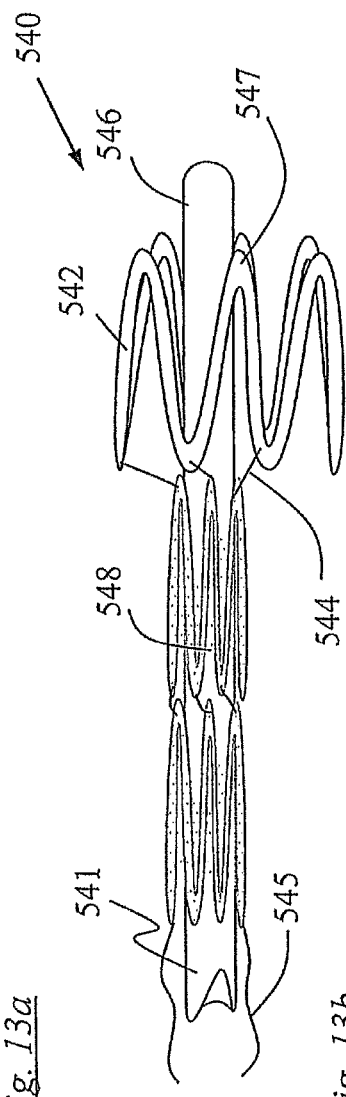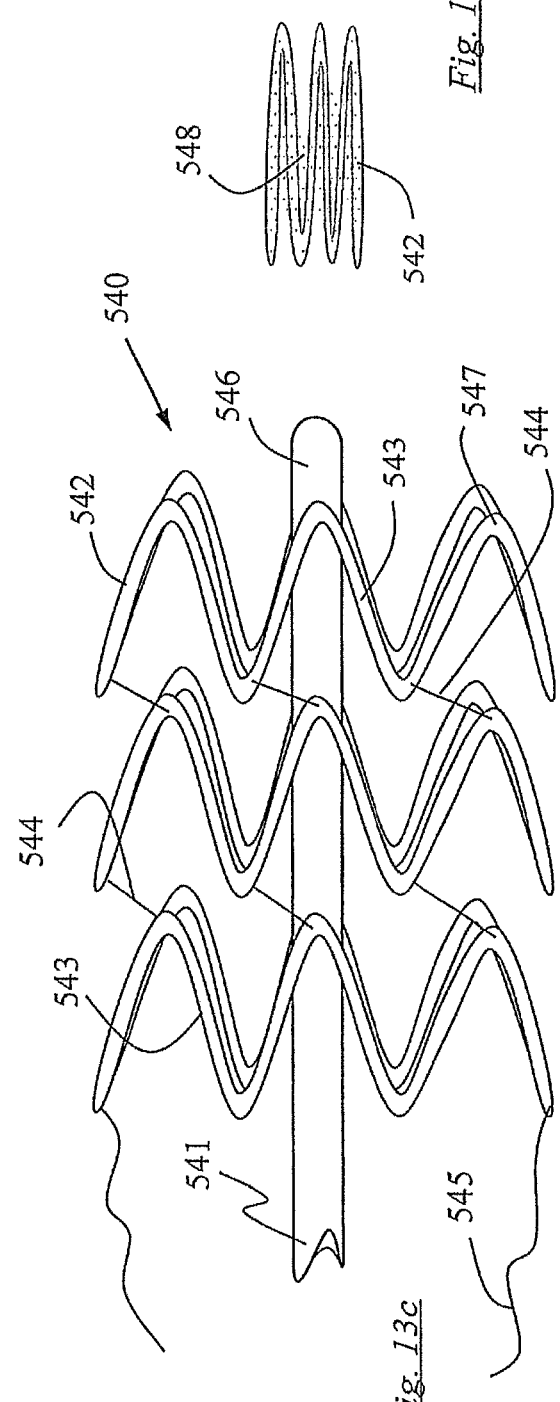
Fig. 13a
Fig. 13b
Fig. 13c
Fig. 13d

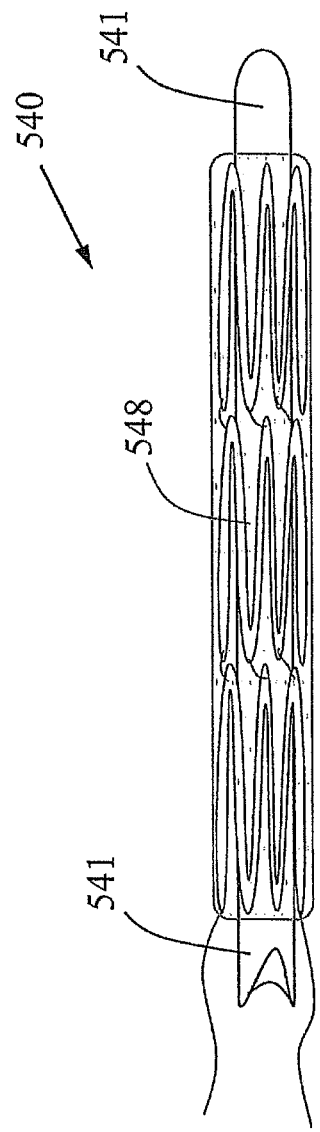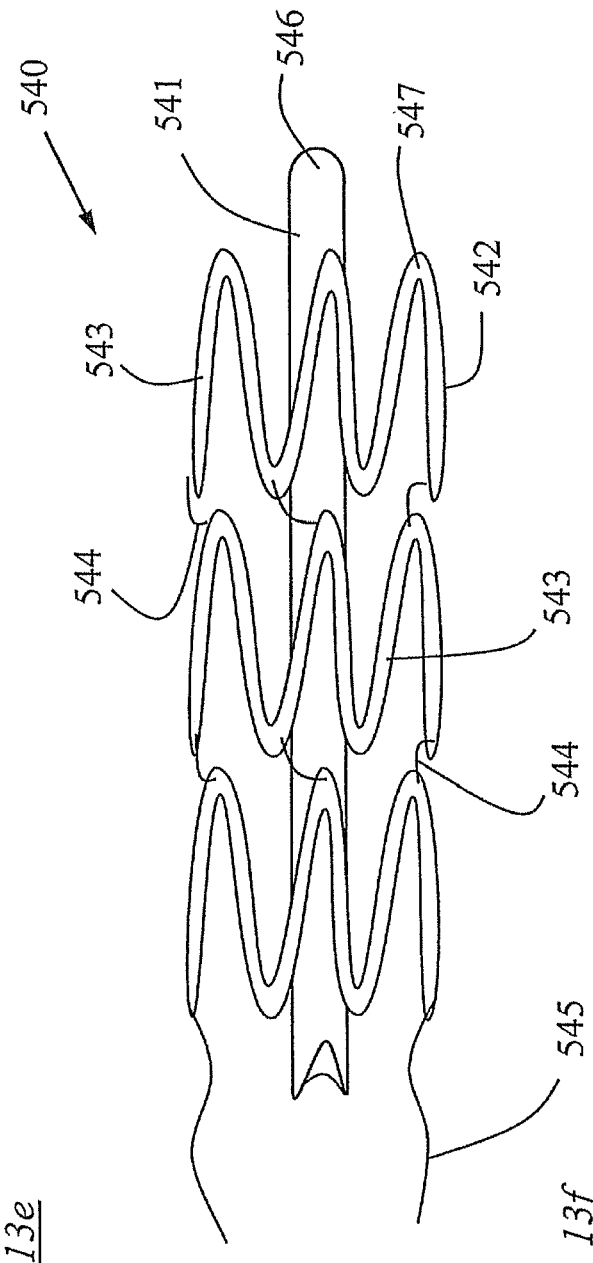
Fig. 13e
Fig. 13f

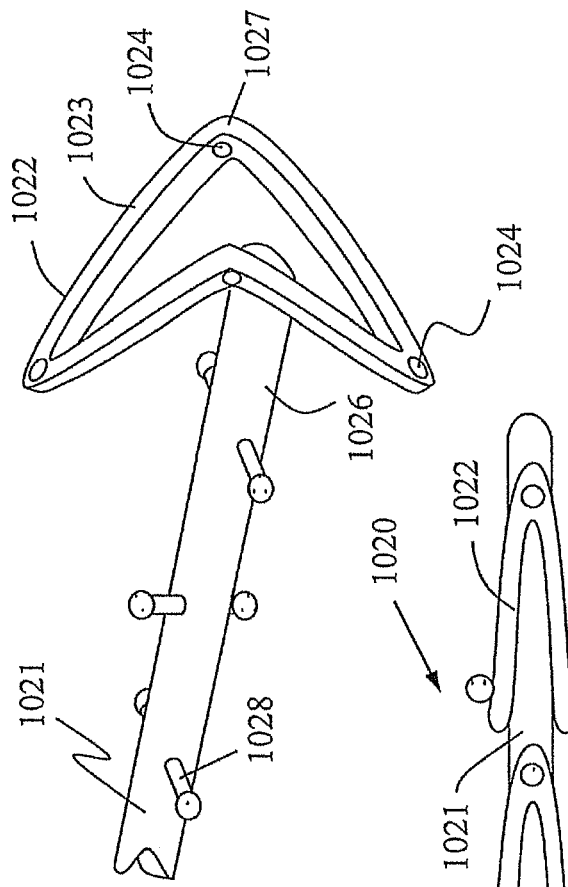
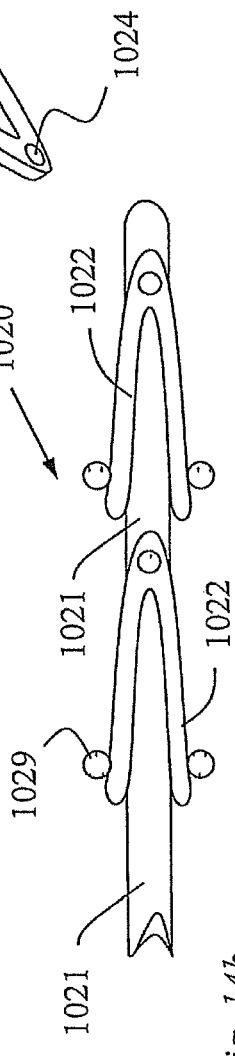
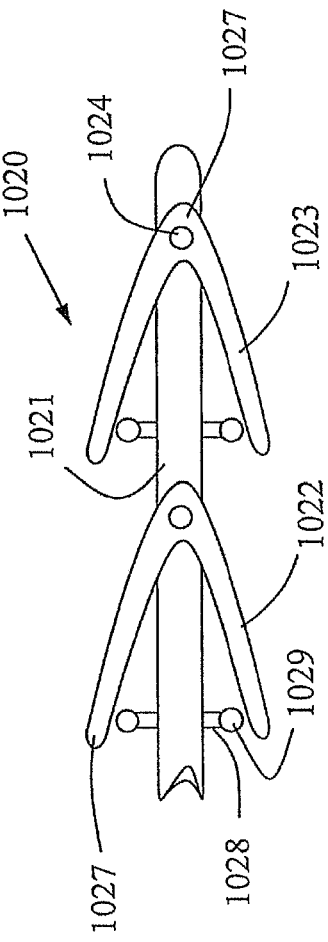
Fig. 14a
Fig. 14b
Fig. 14c

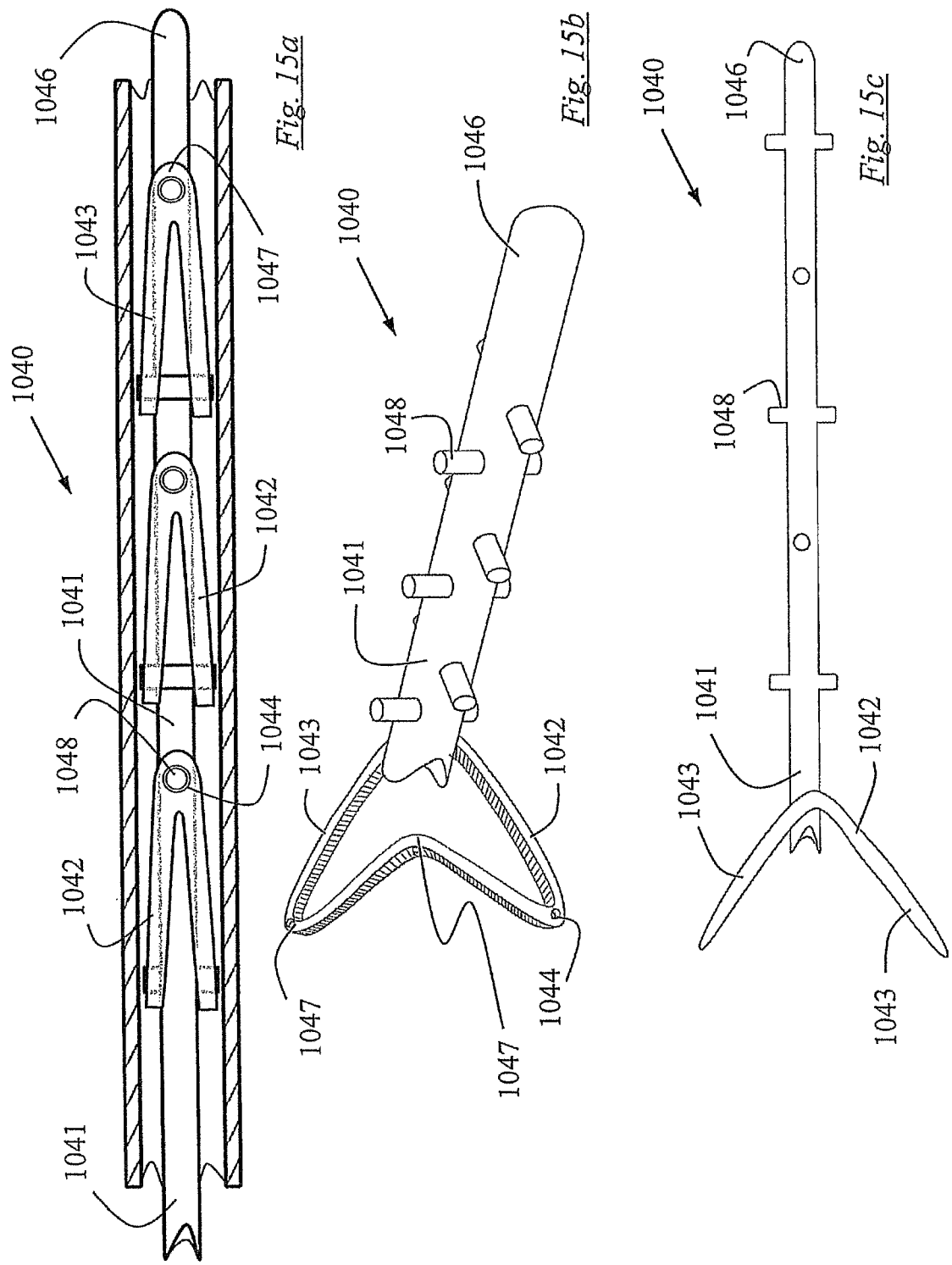

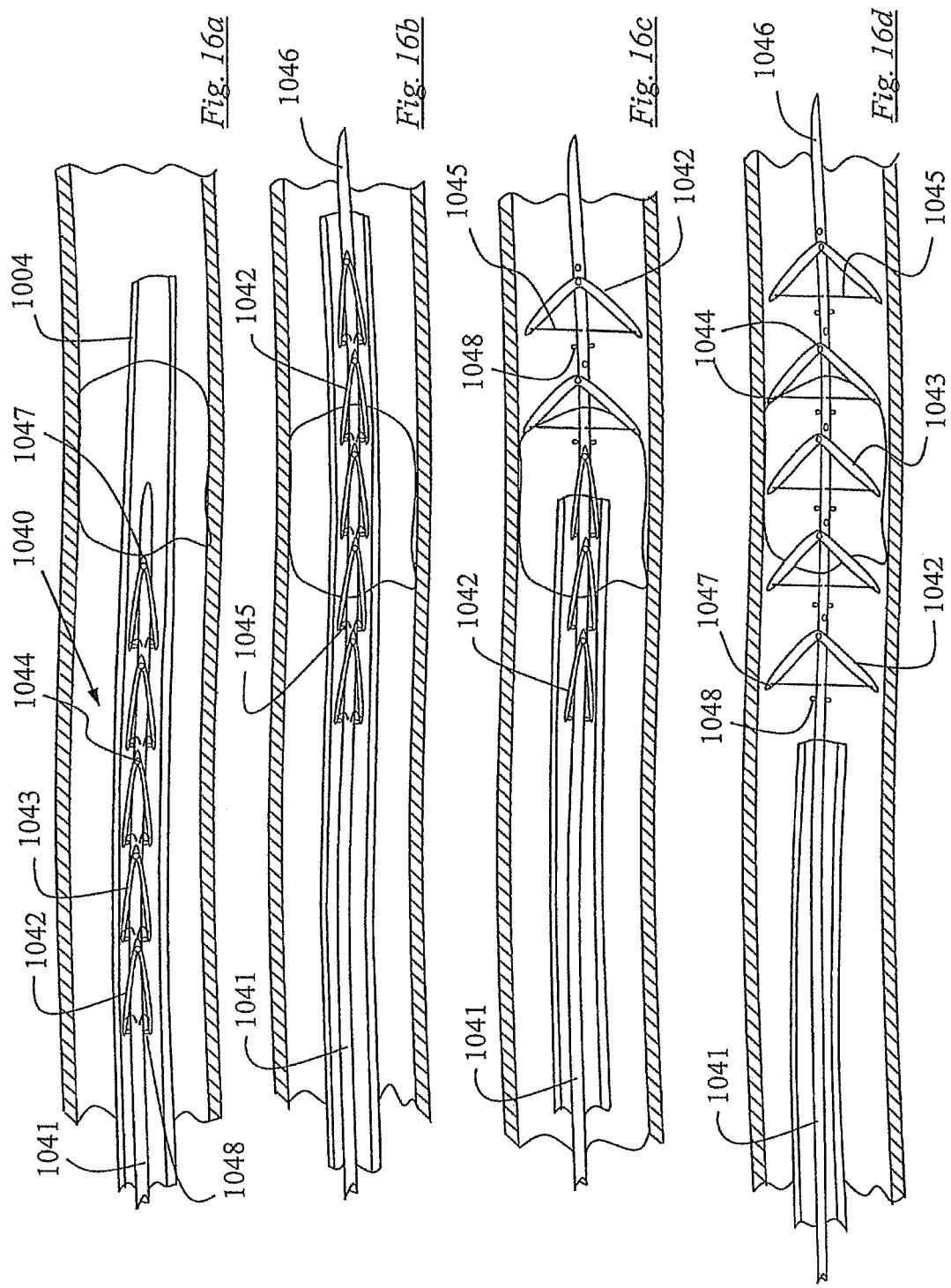

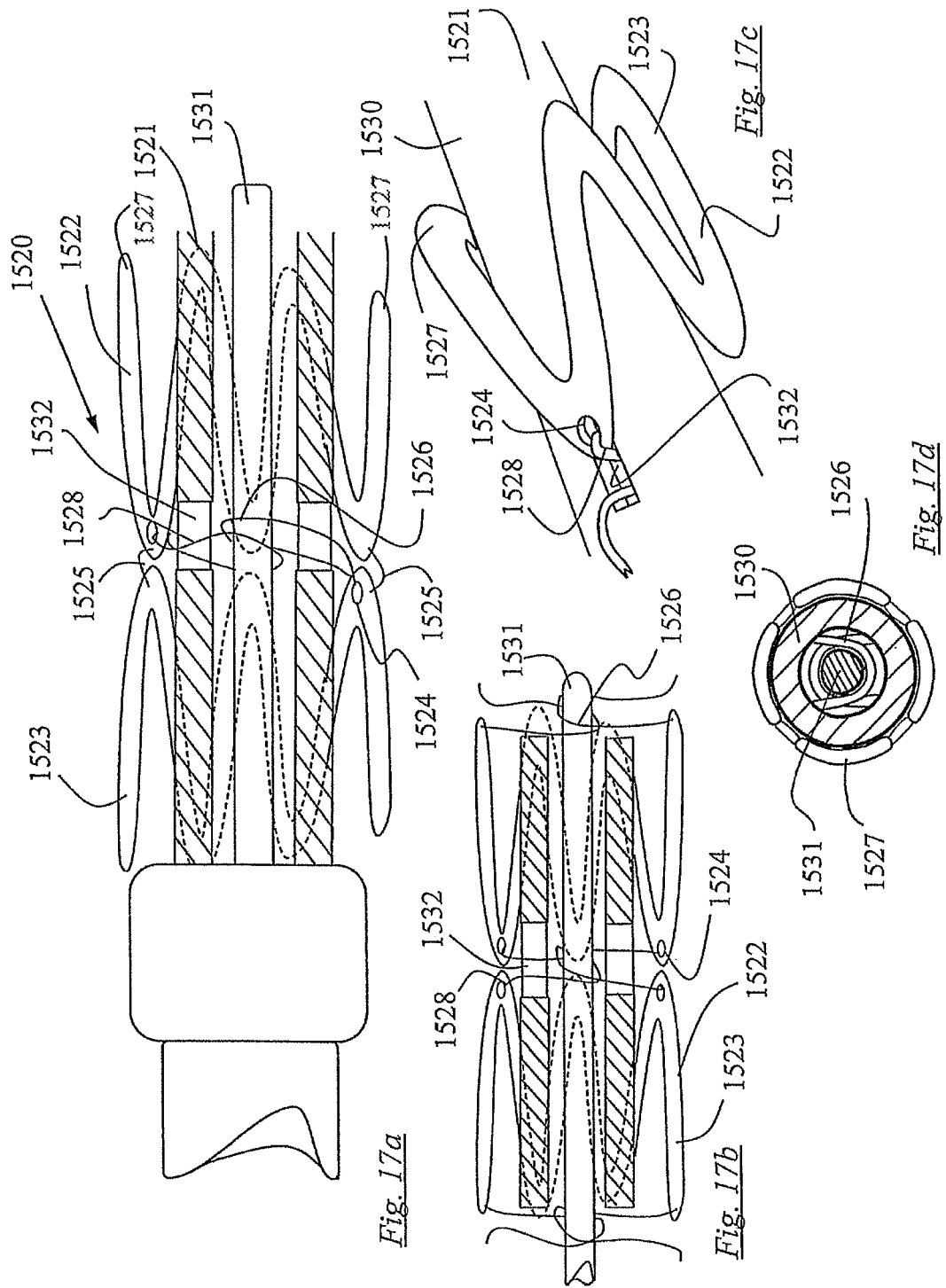

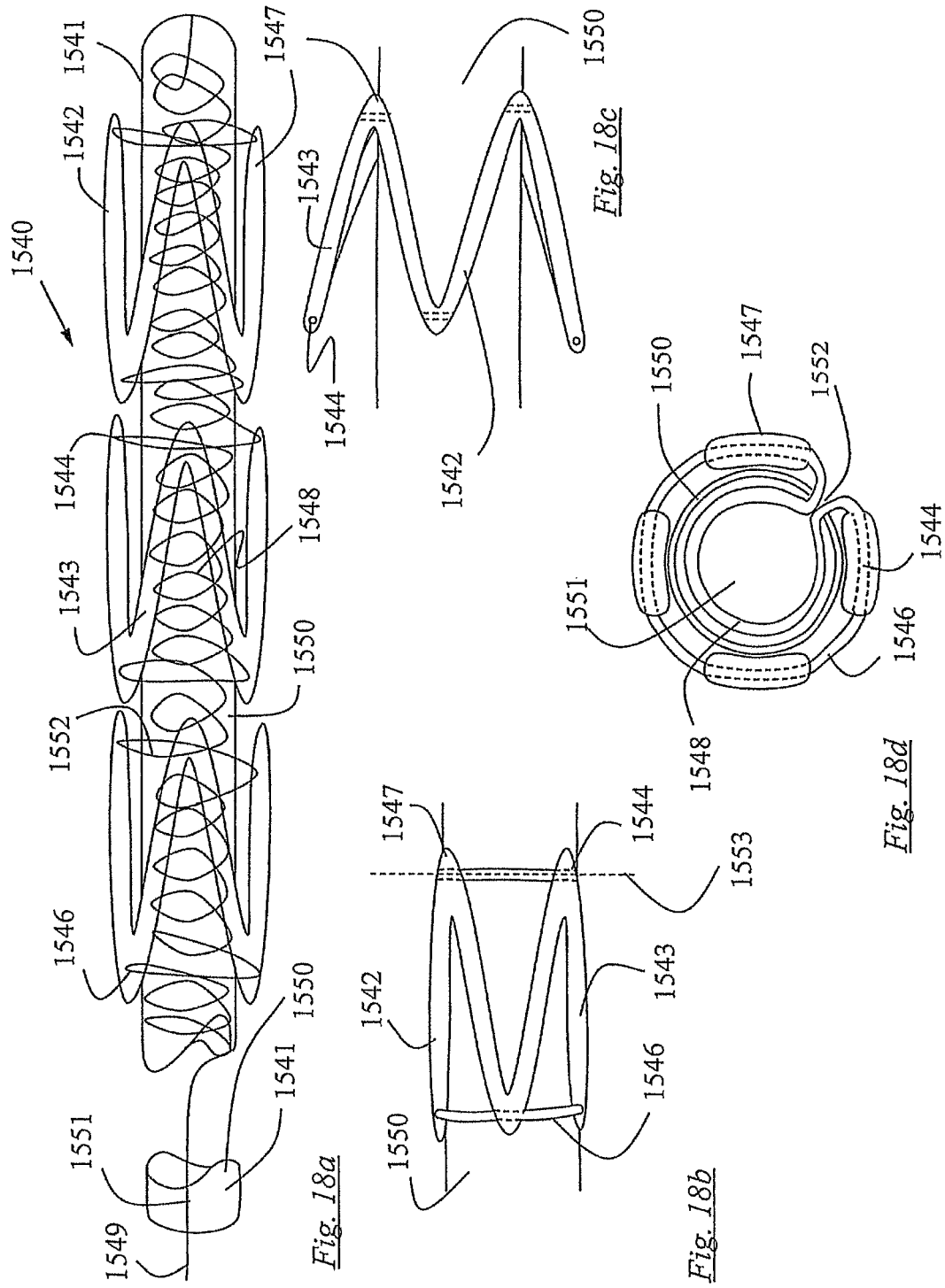

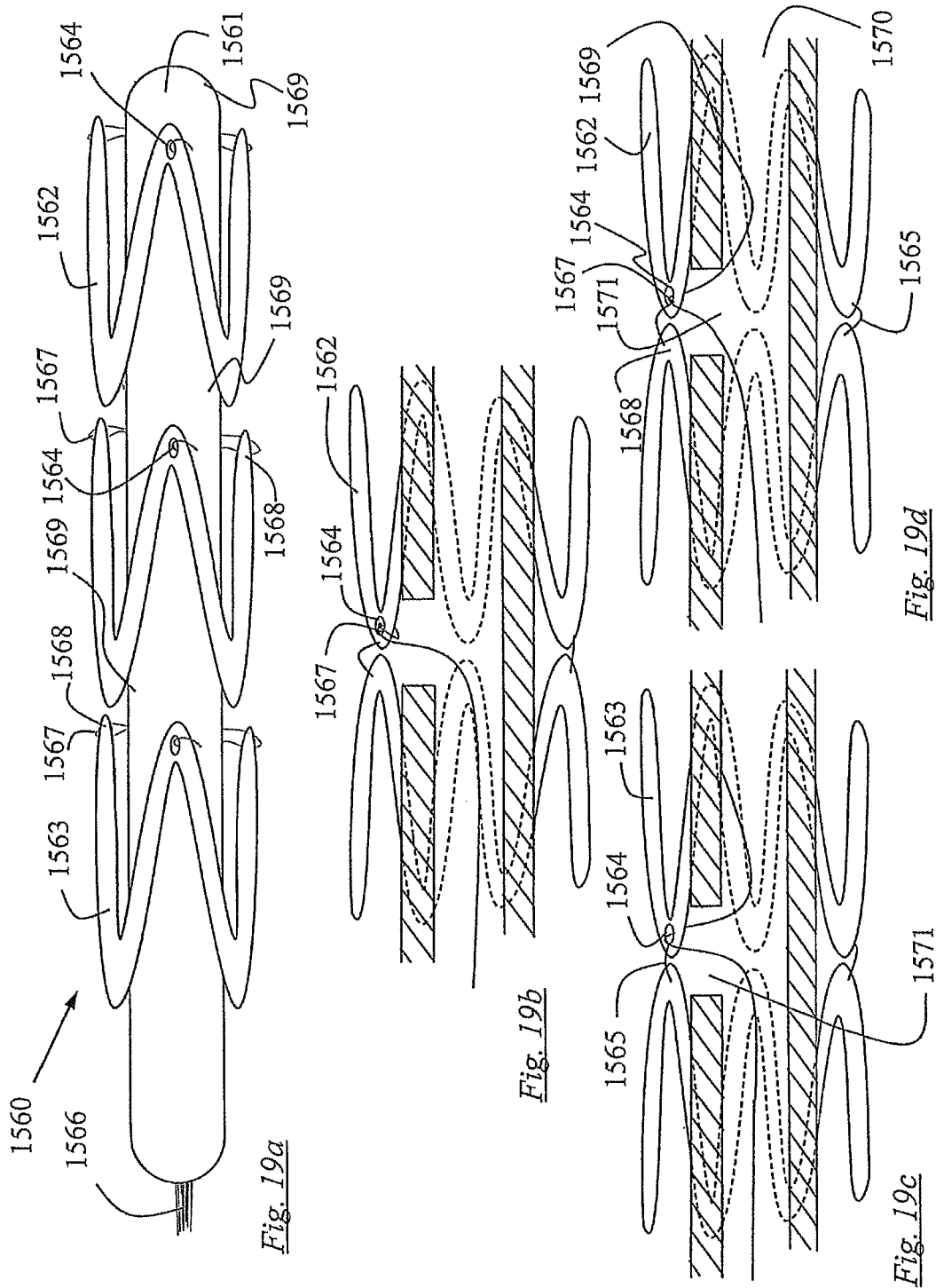

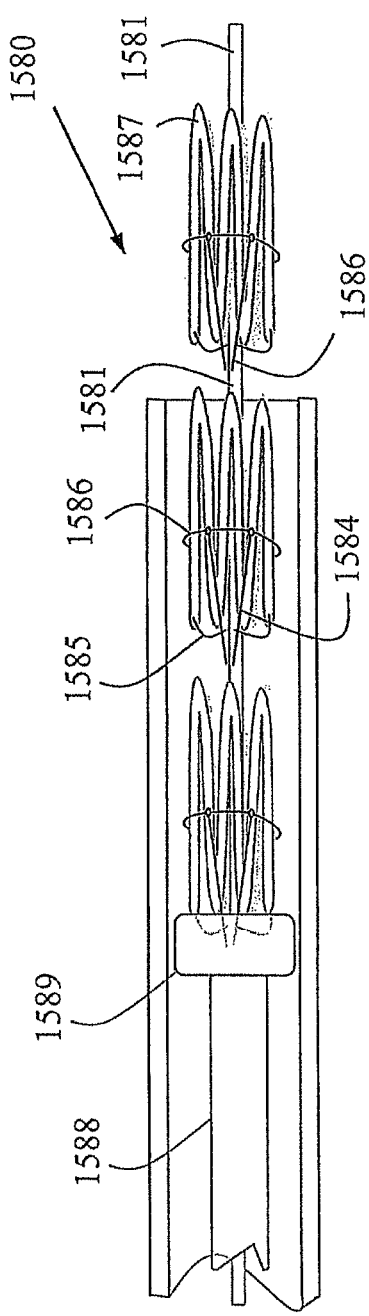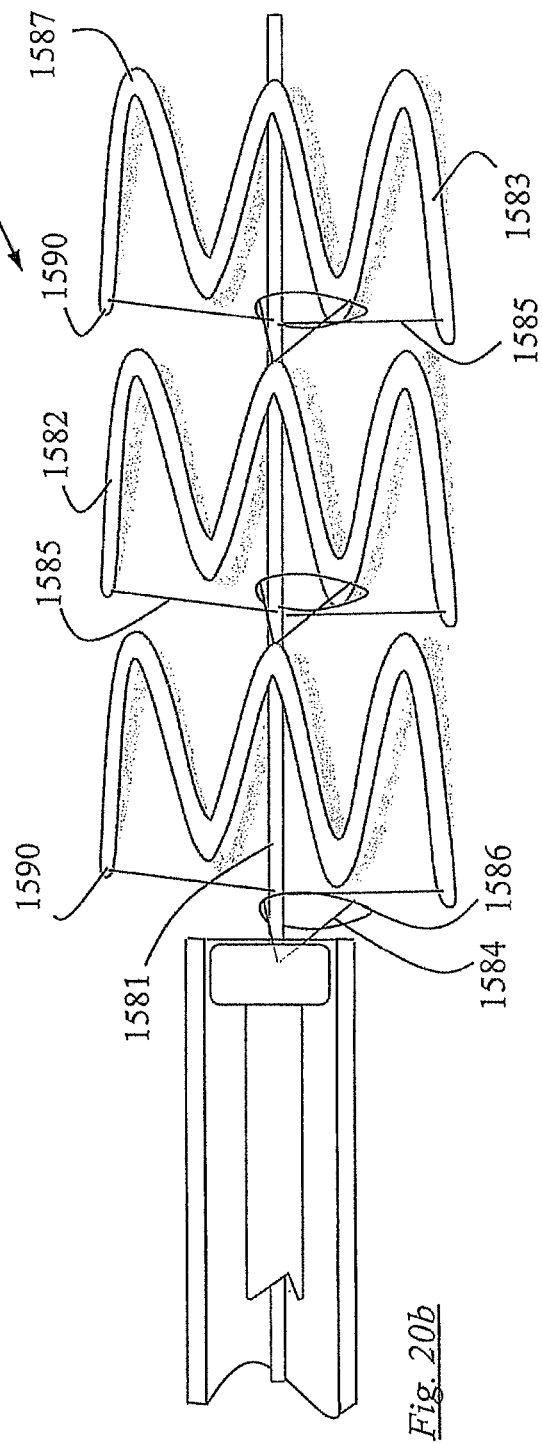
Fig. 20a
Fig. 20b

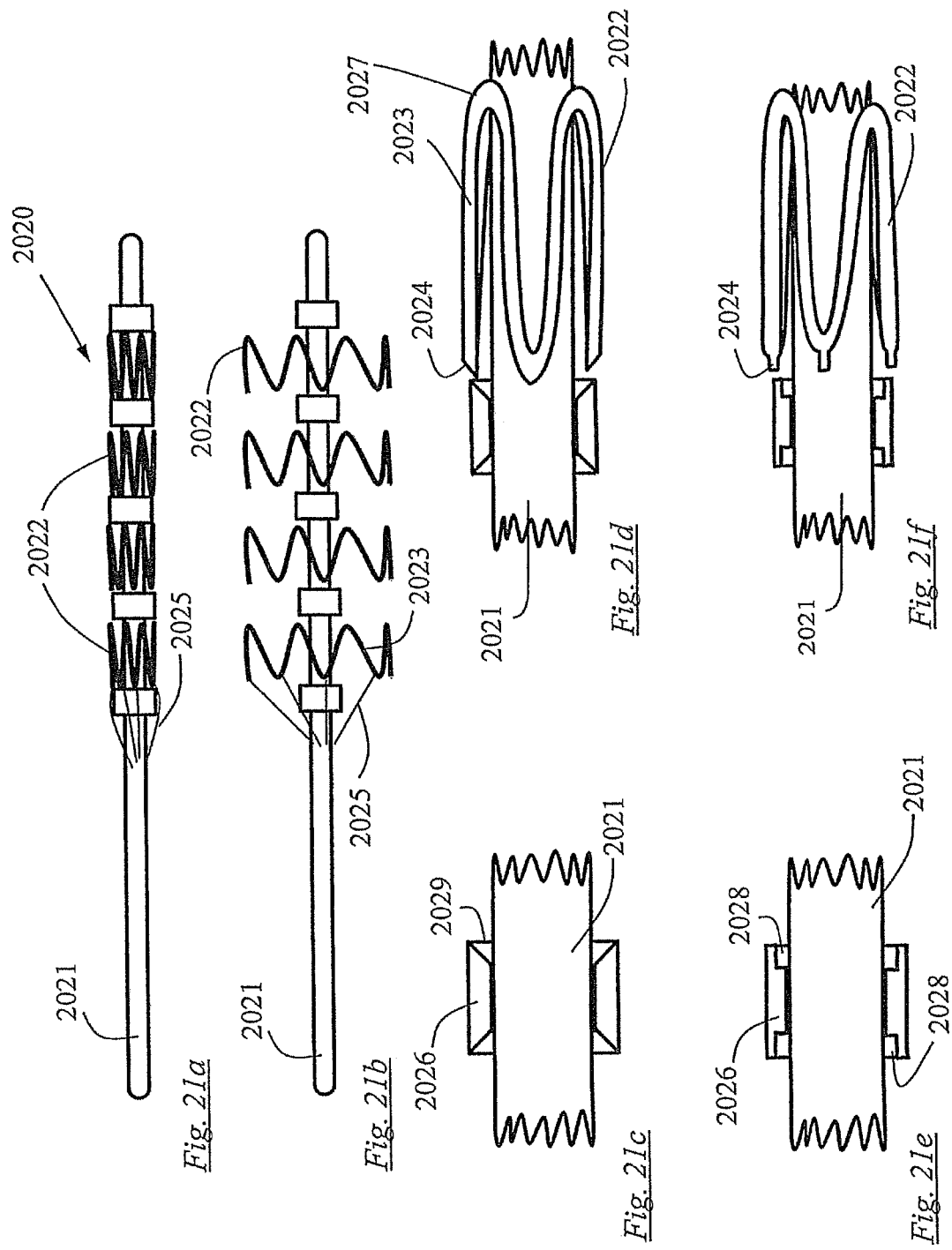

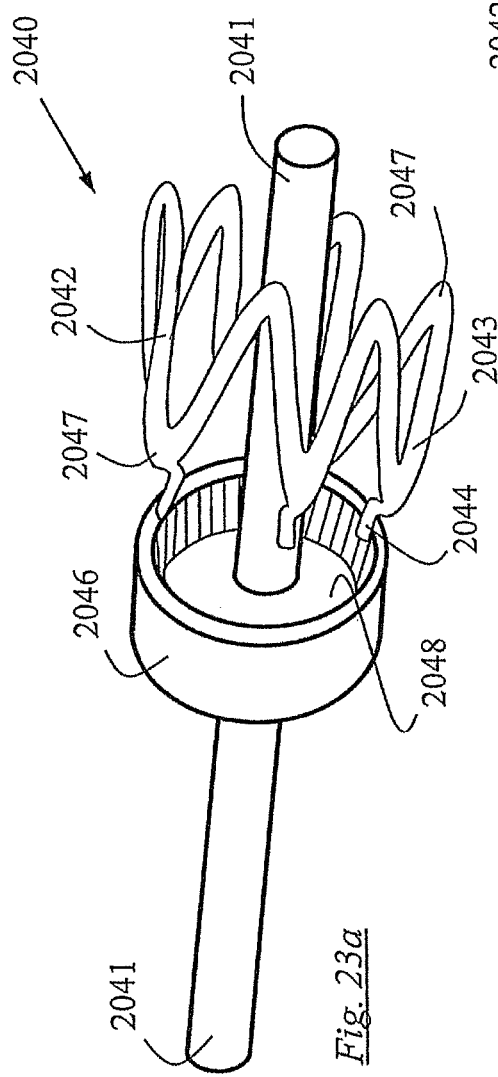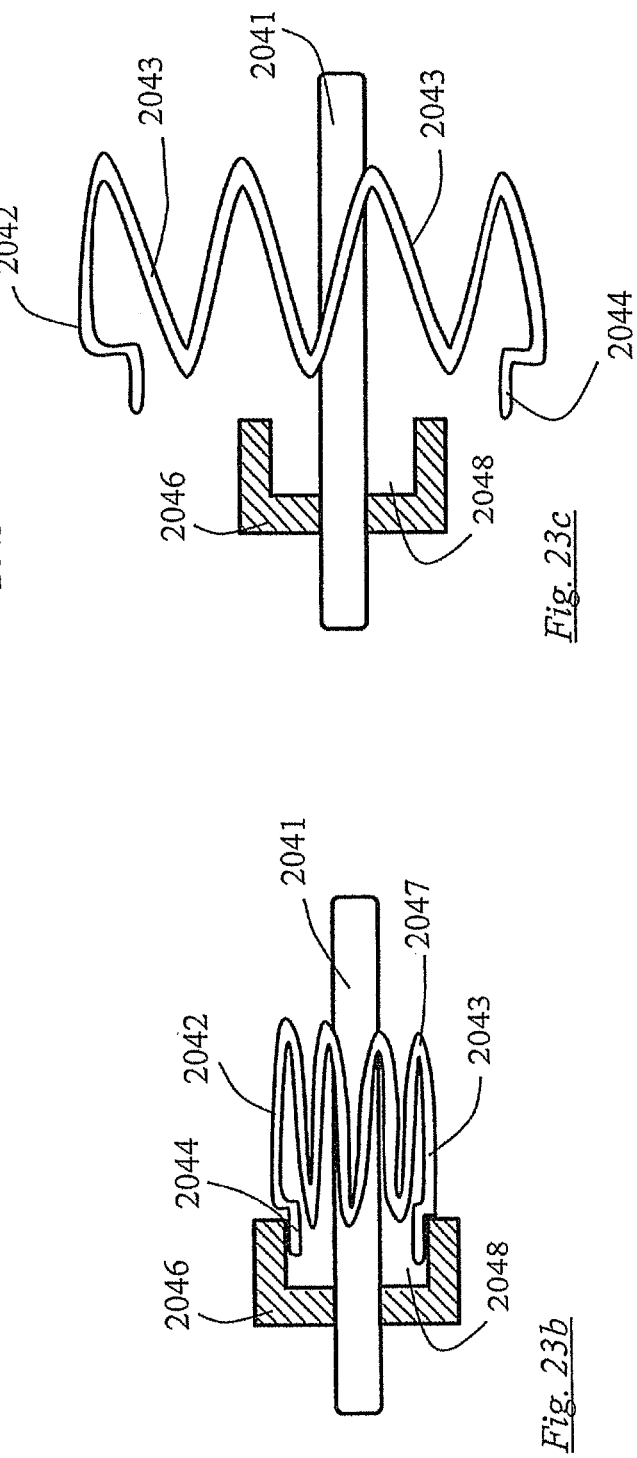

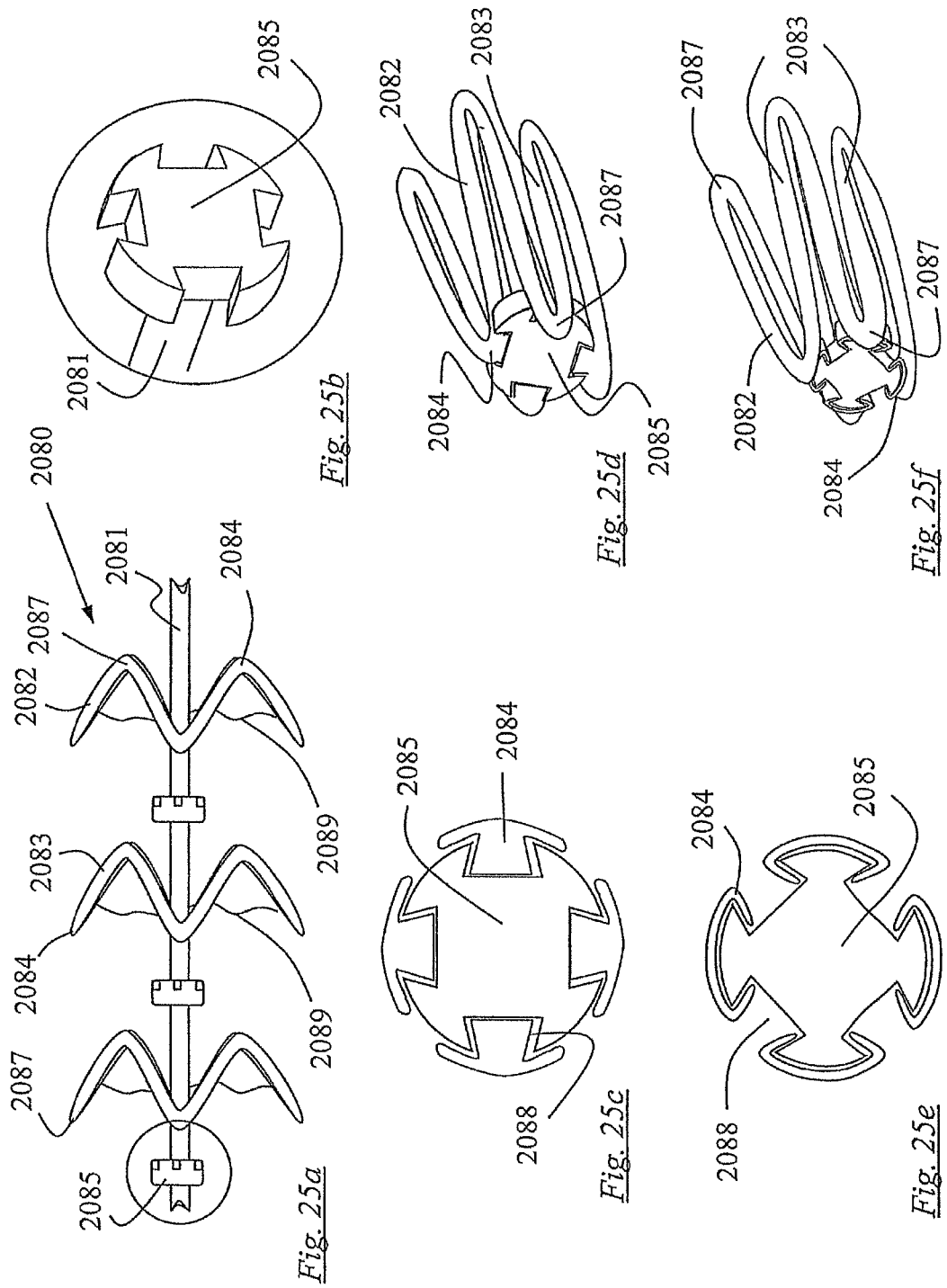

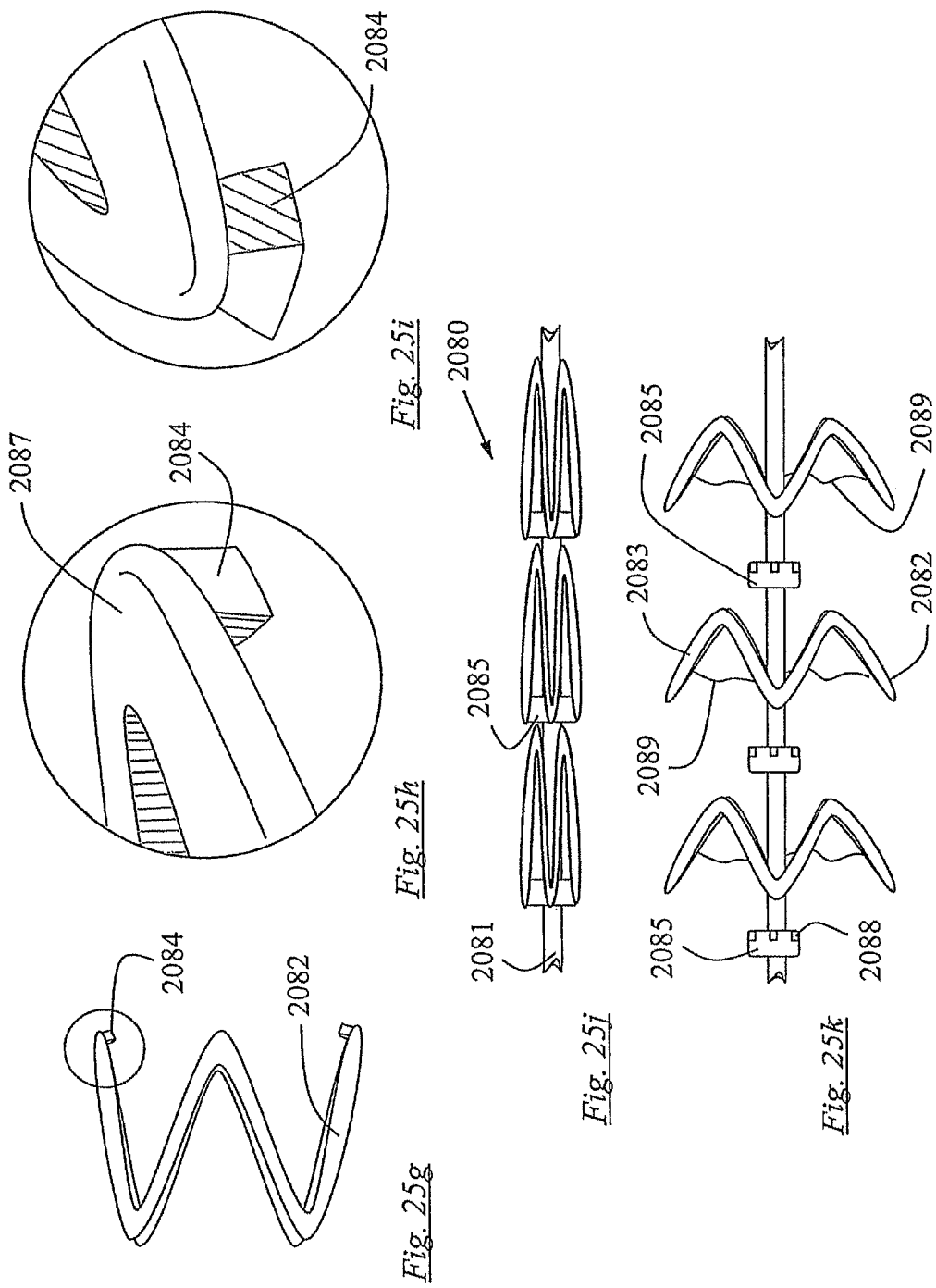

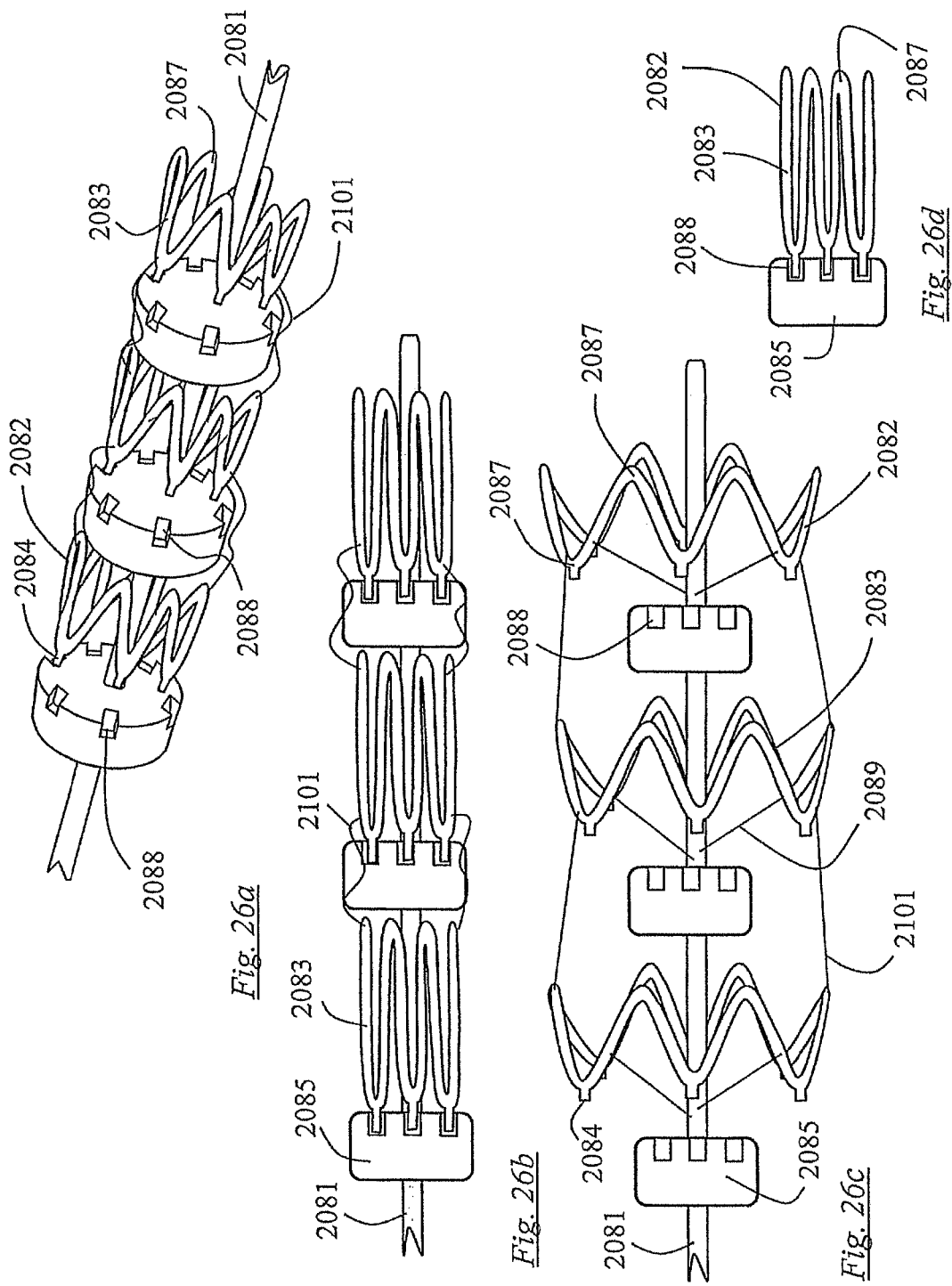

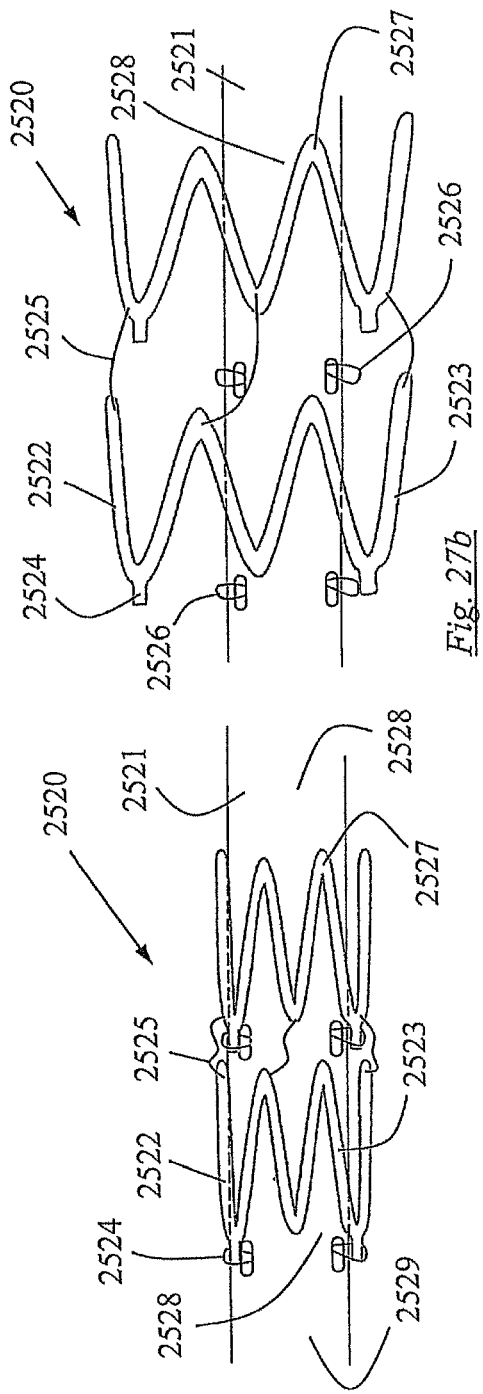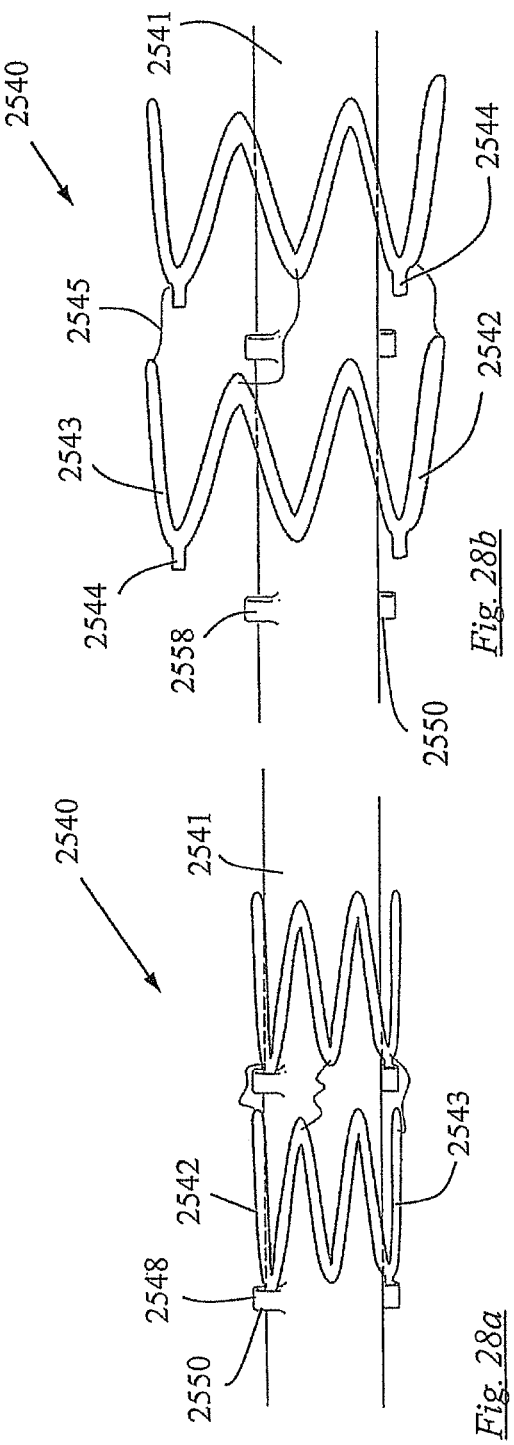

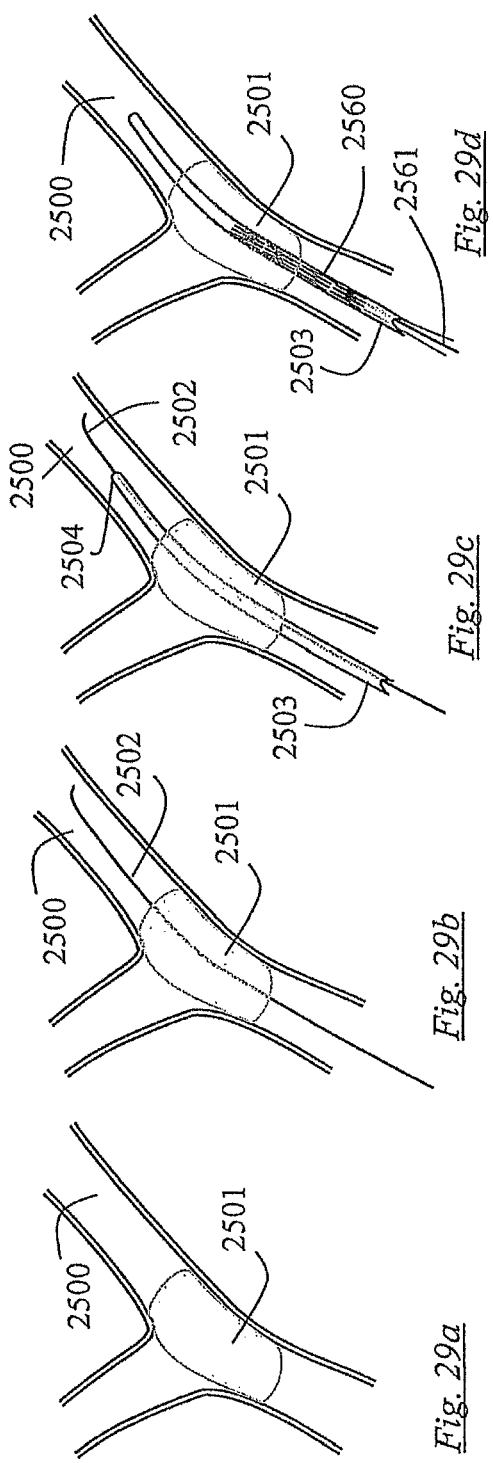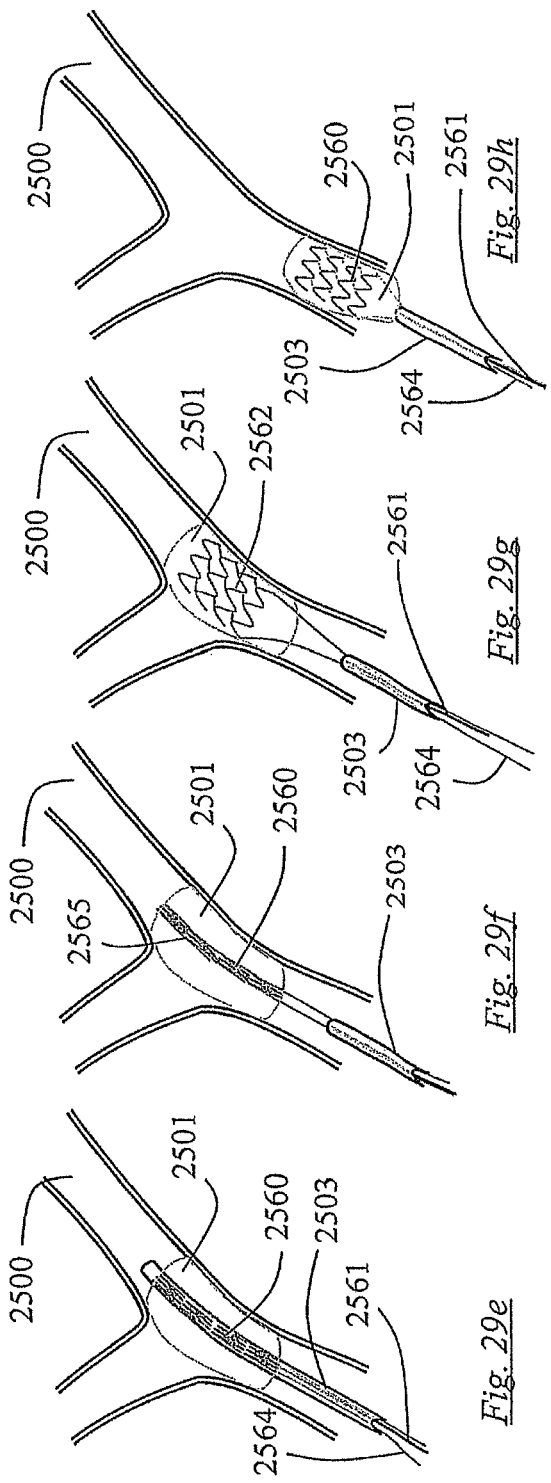

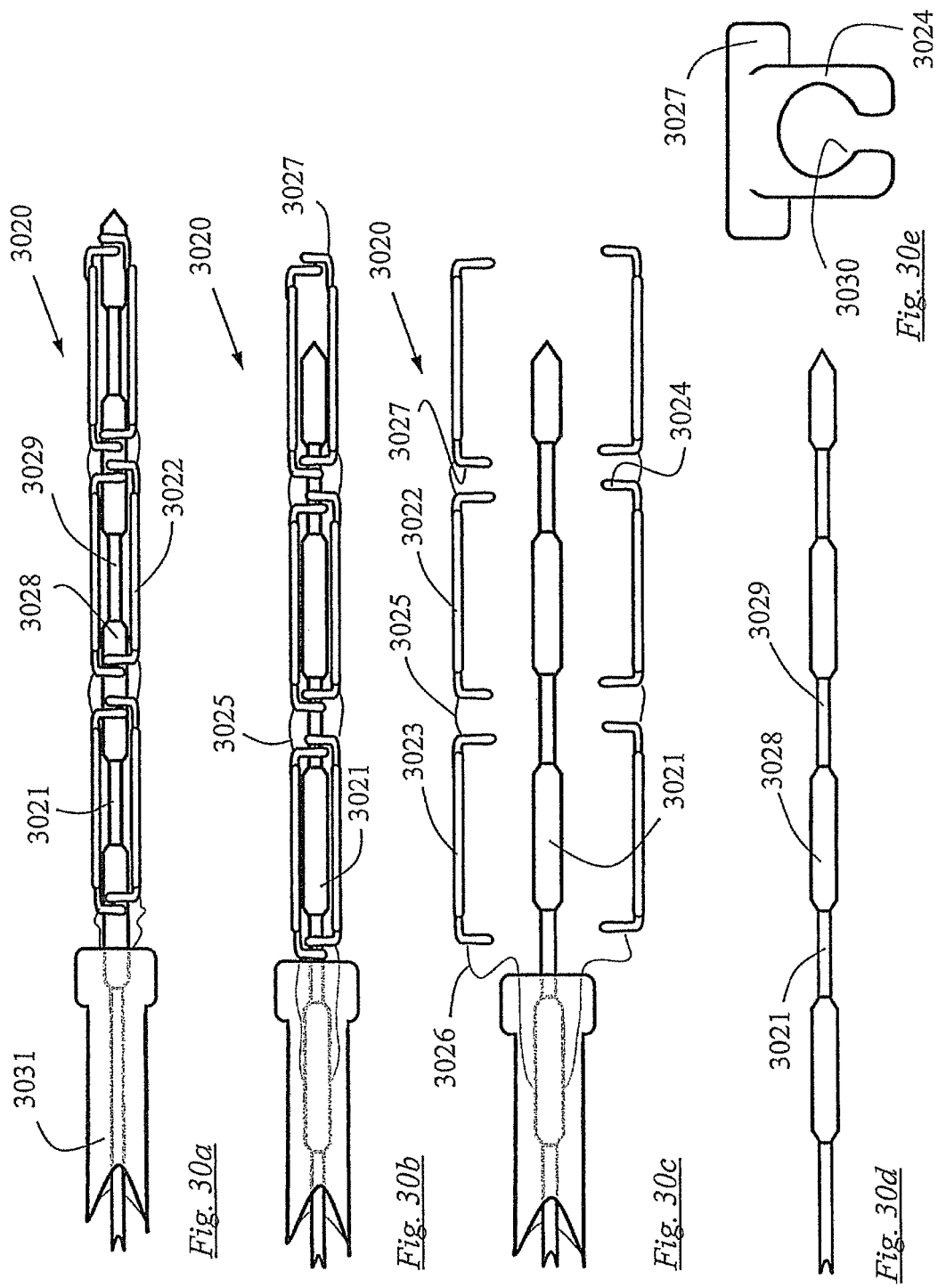

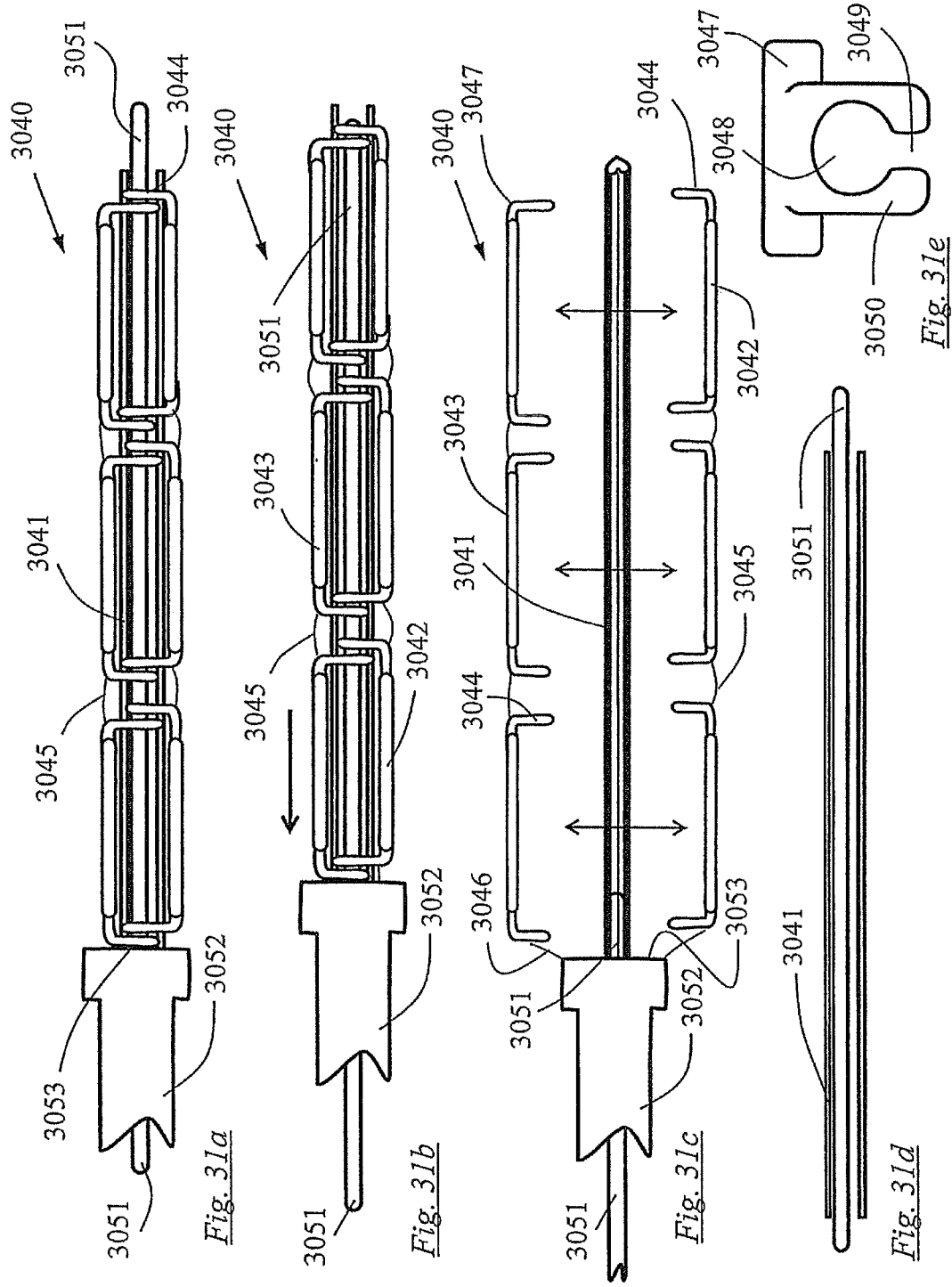

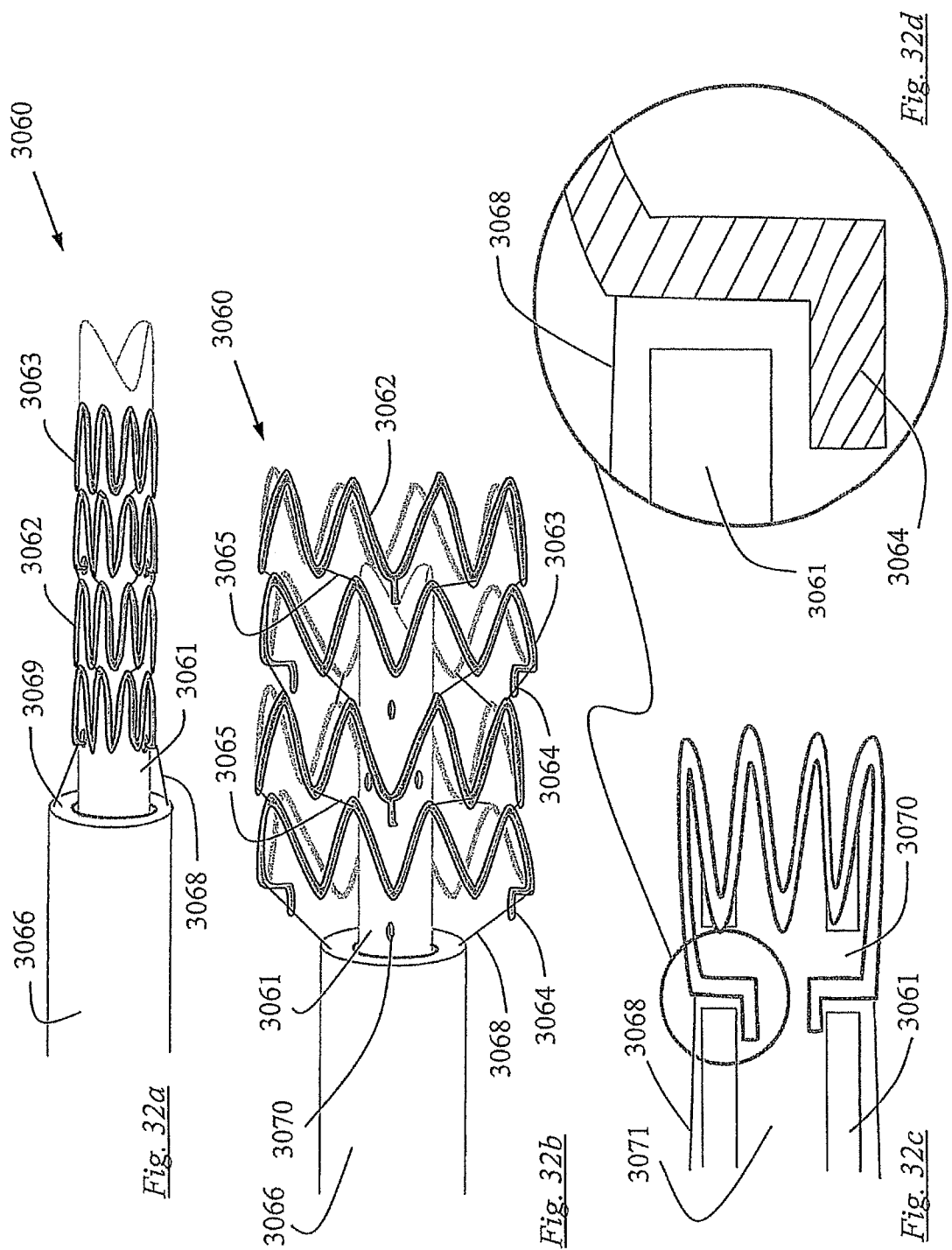

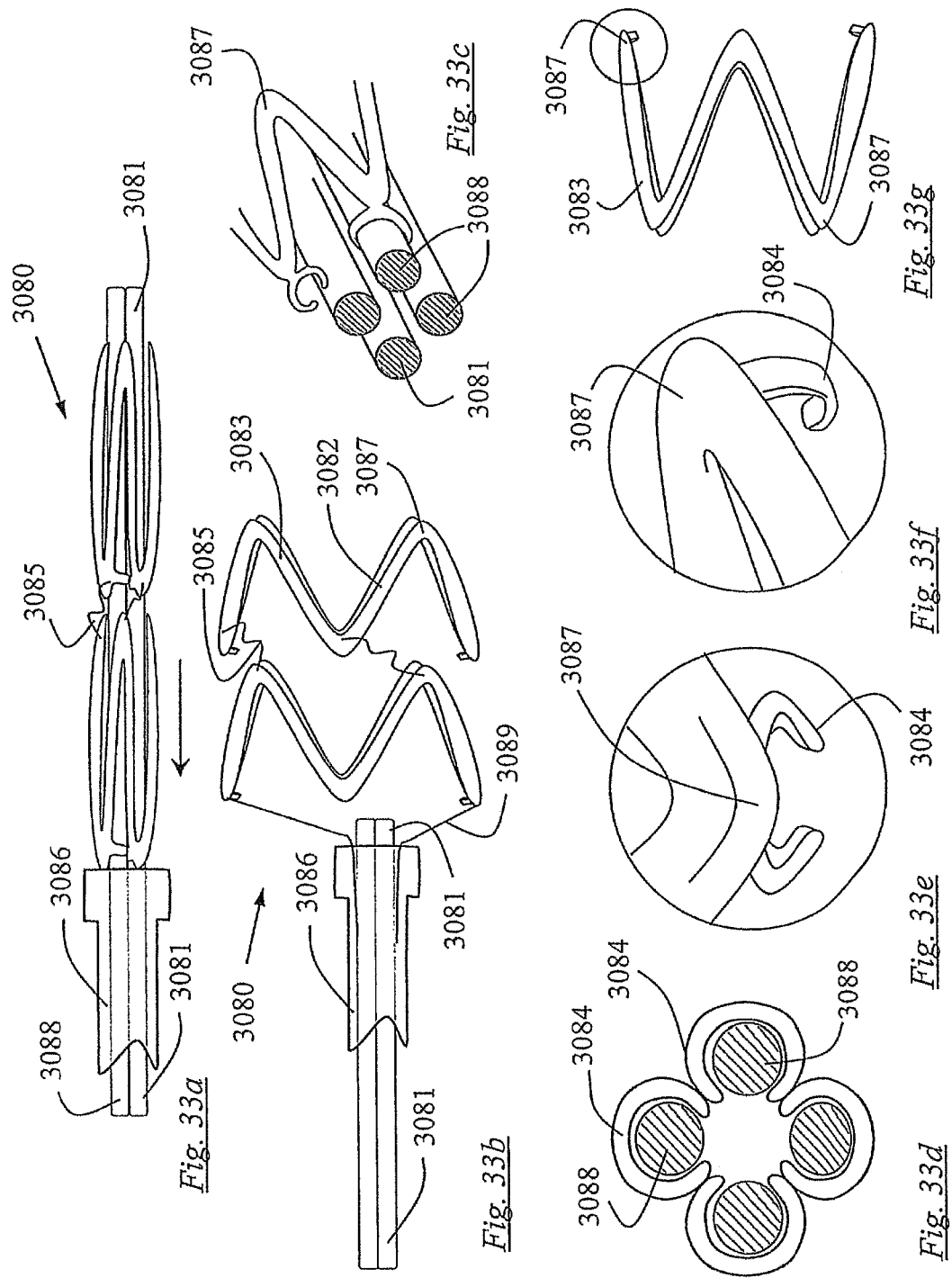

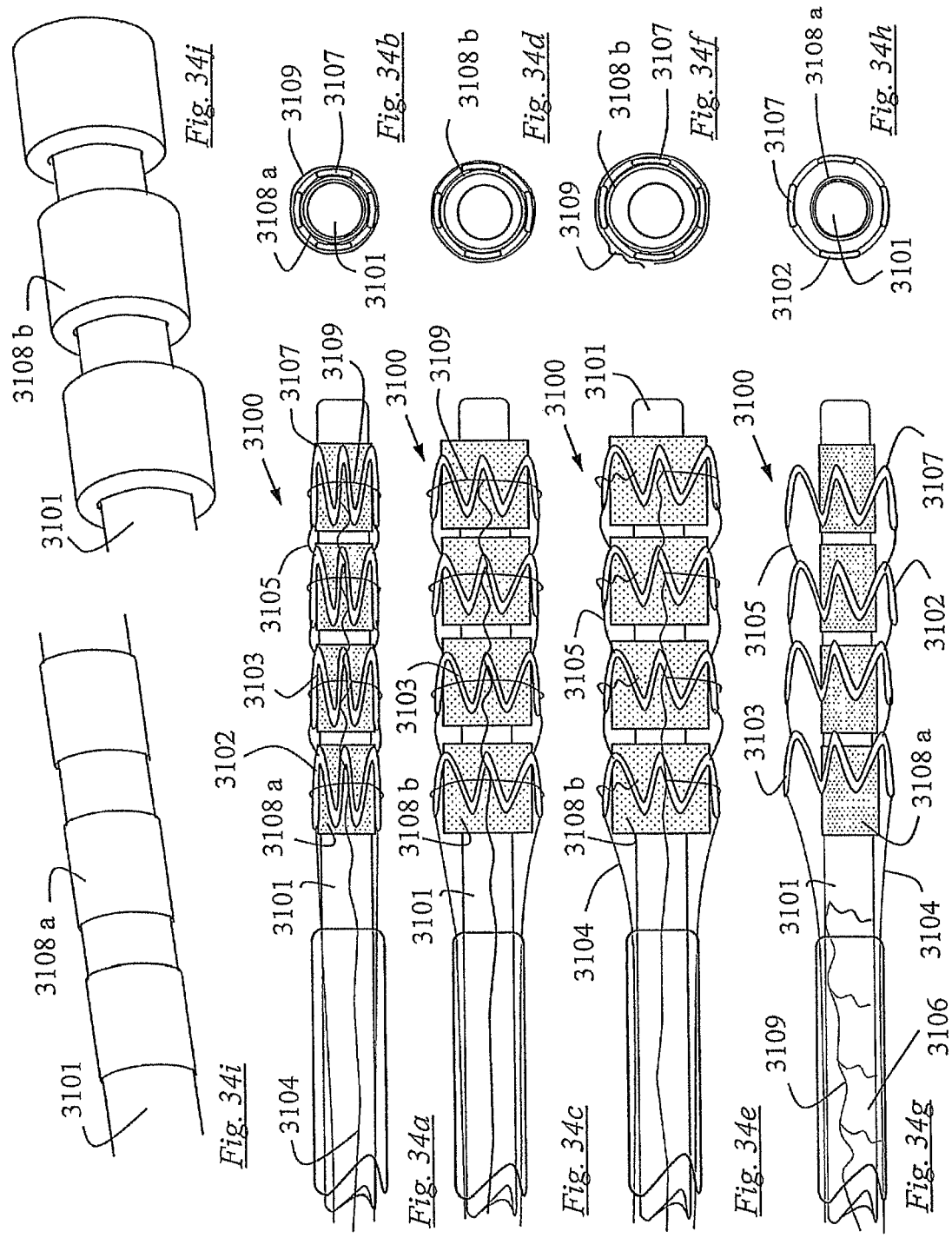

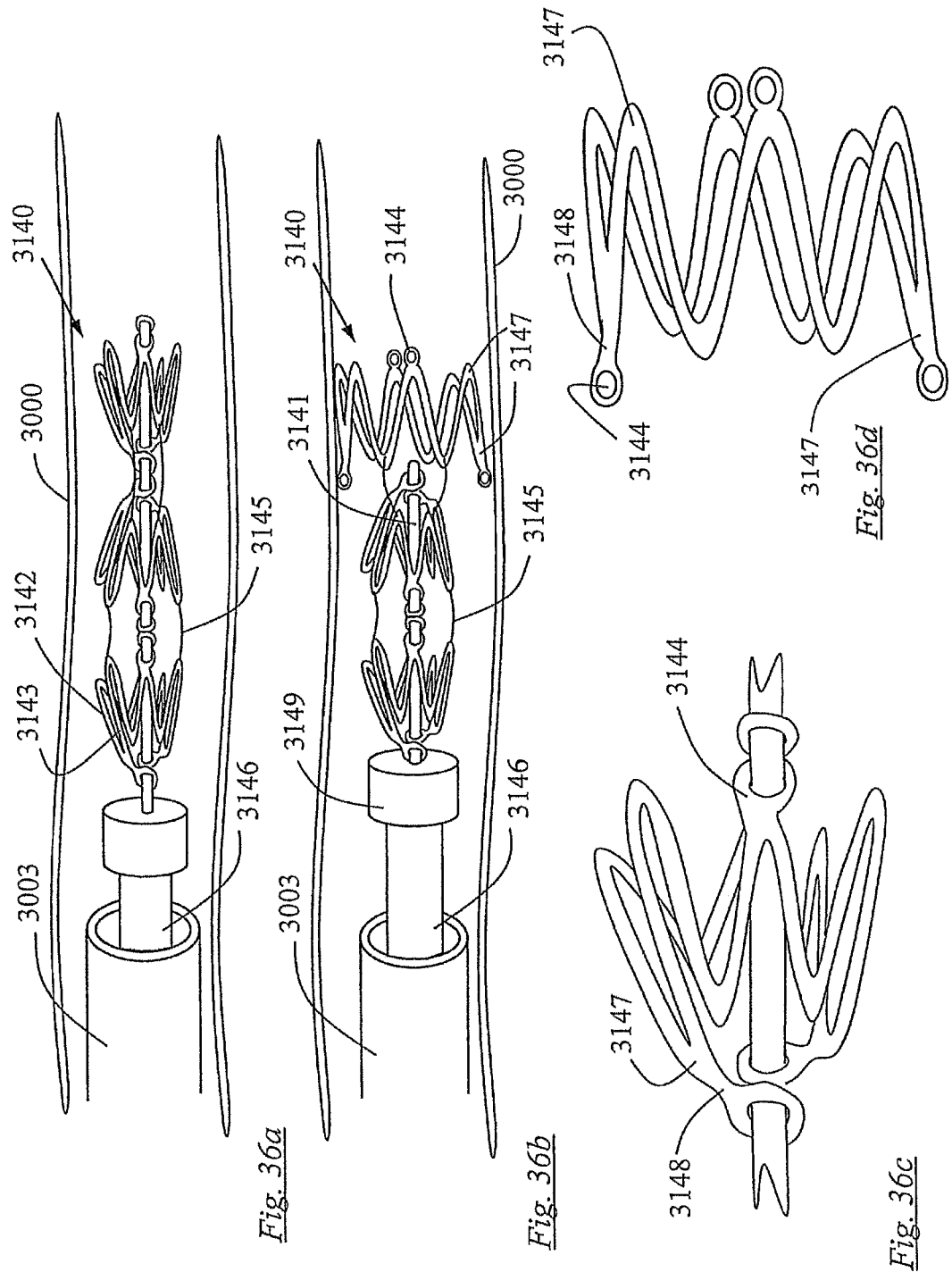

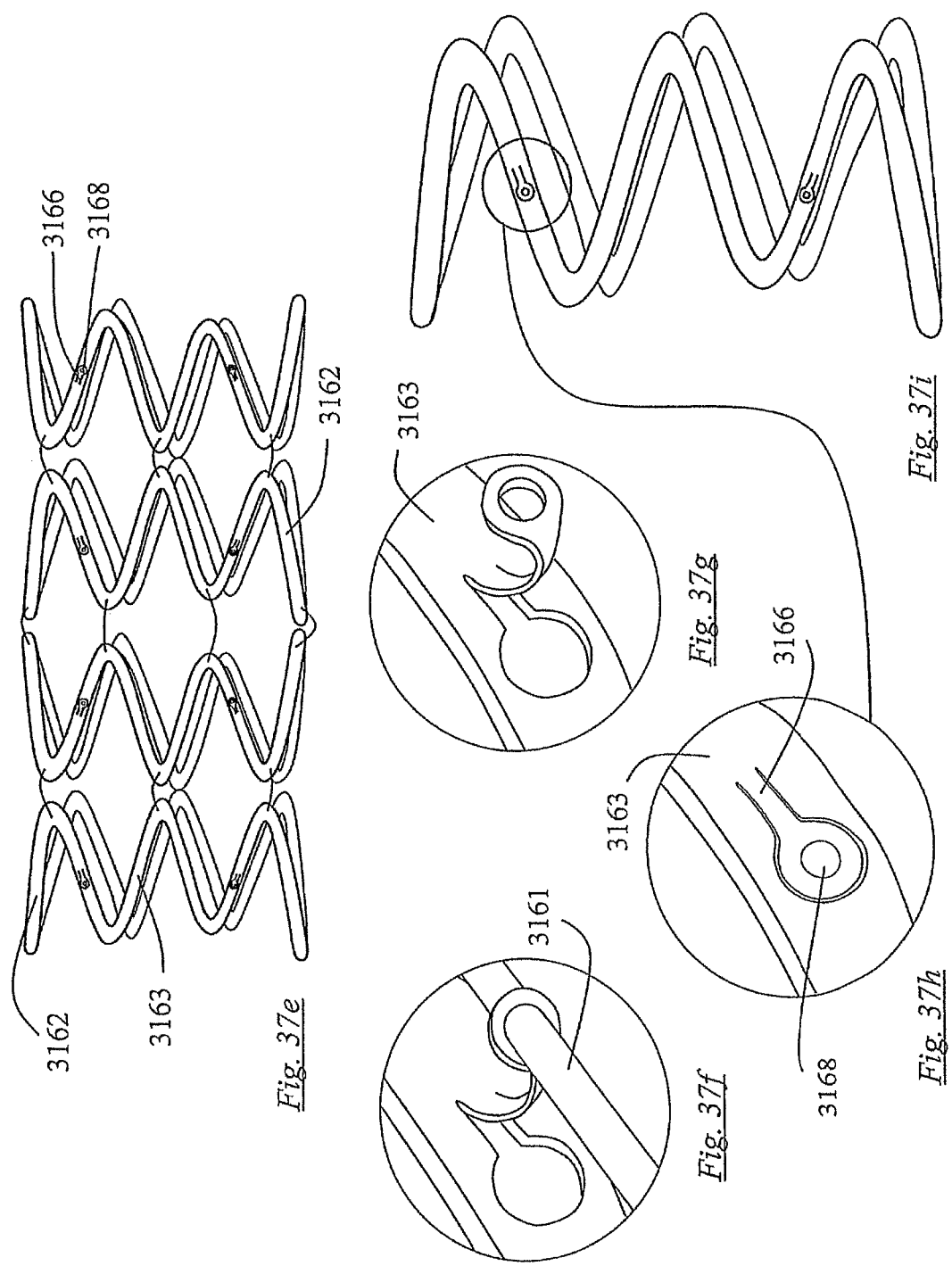

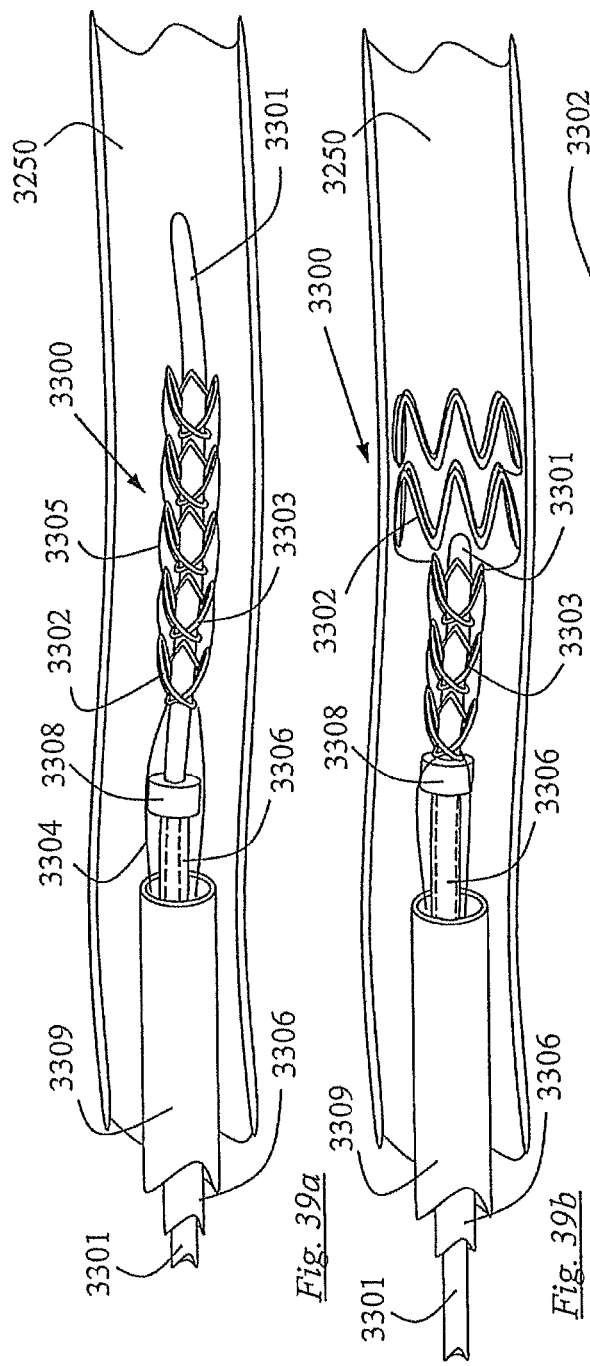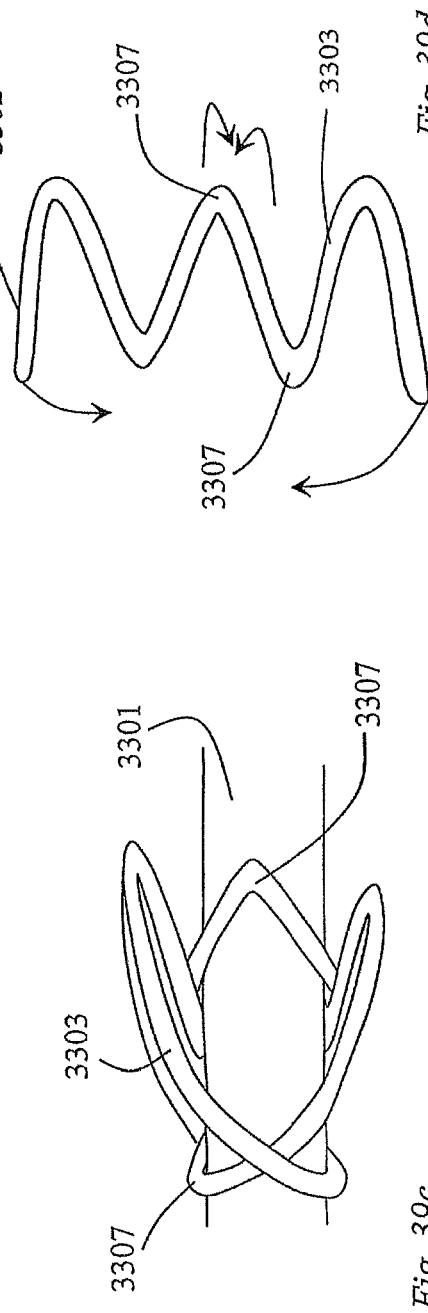

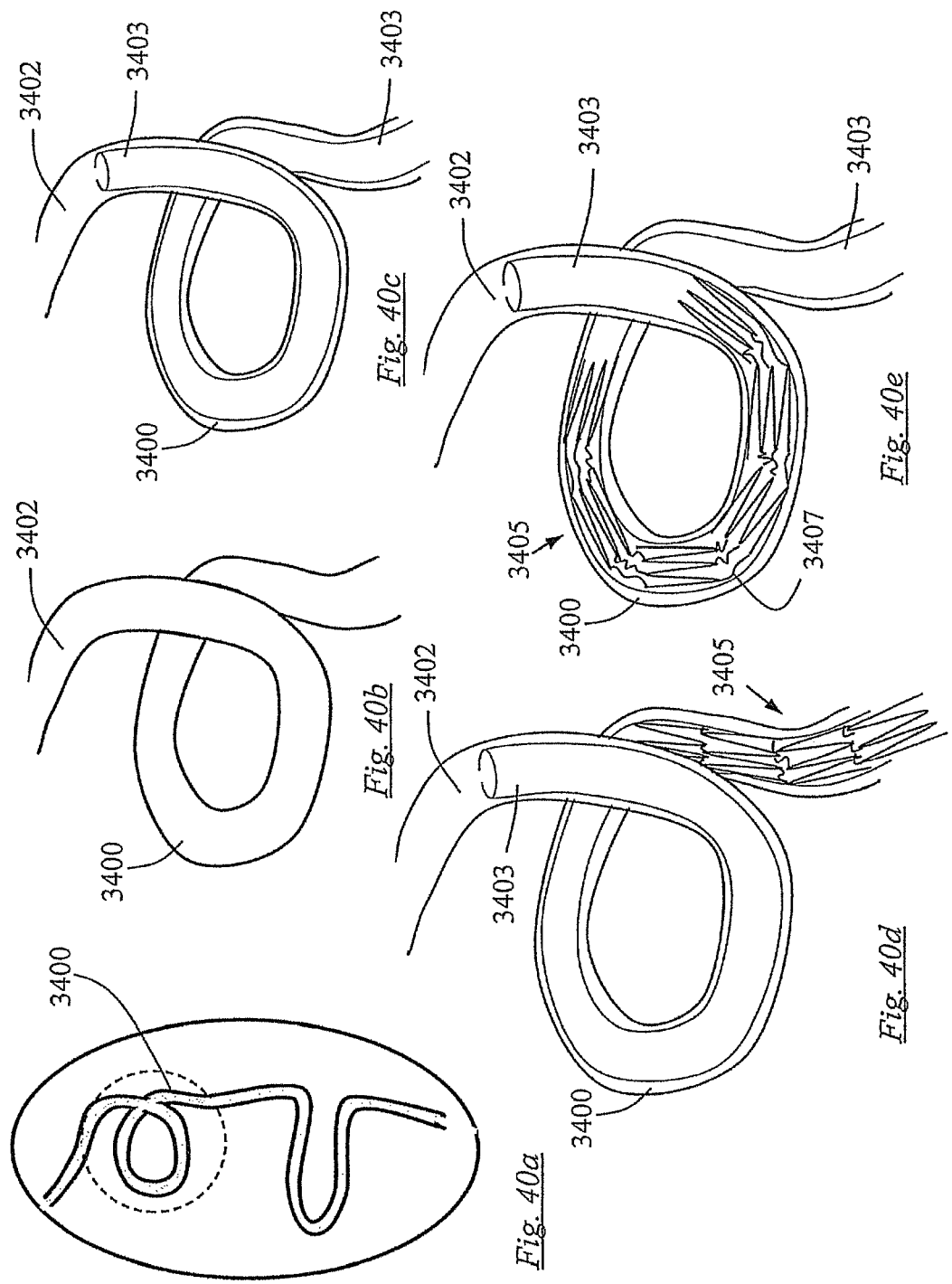

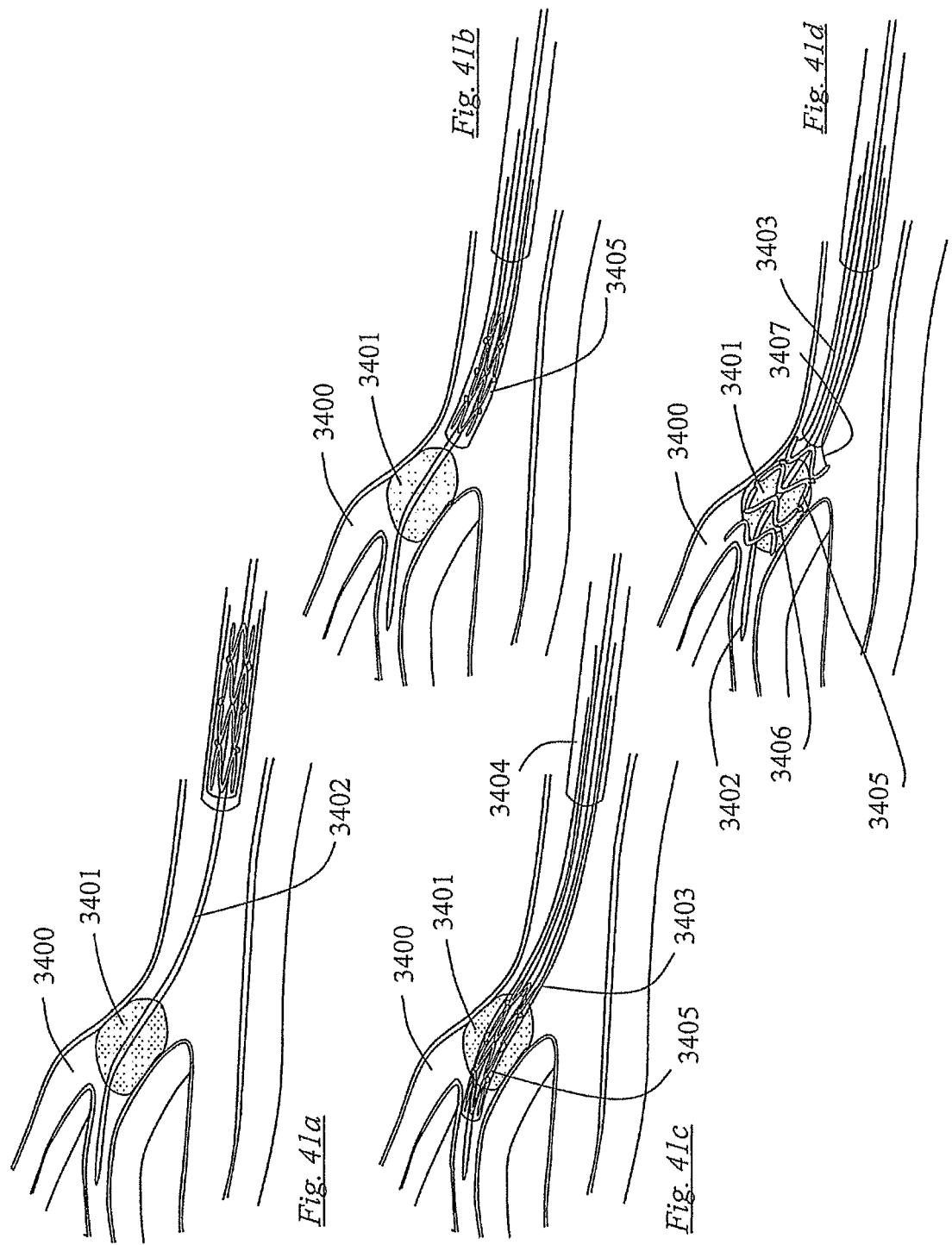

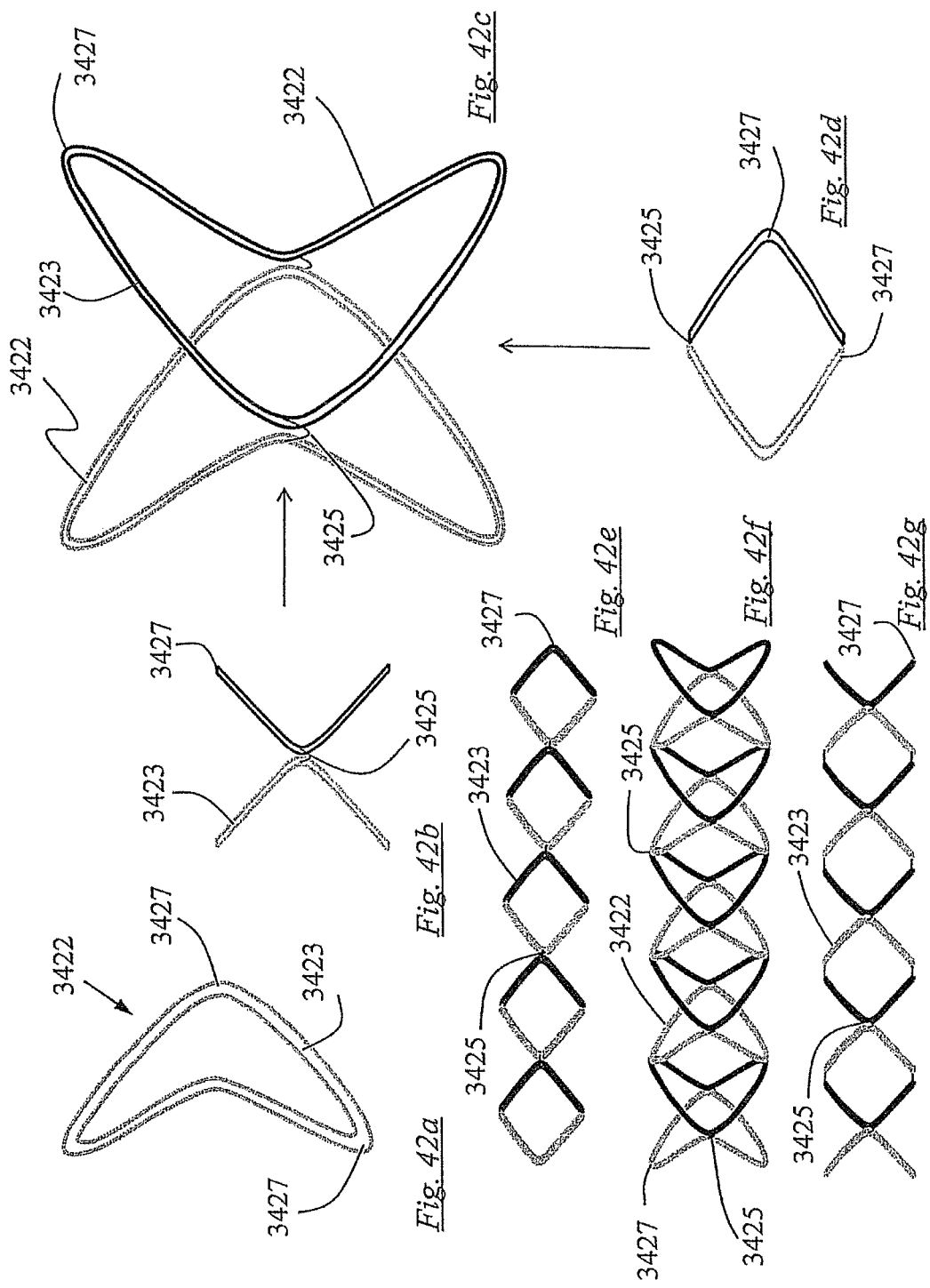

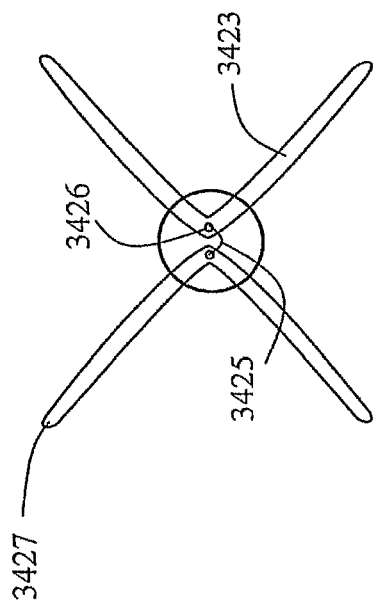
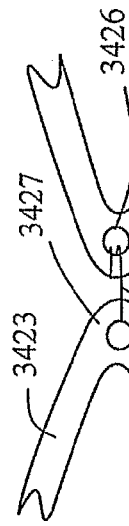
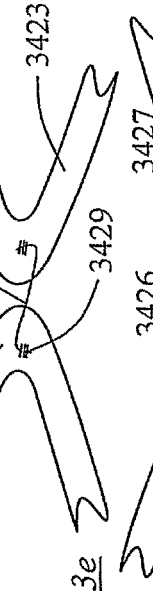
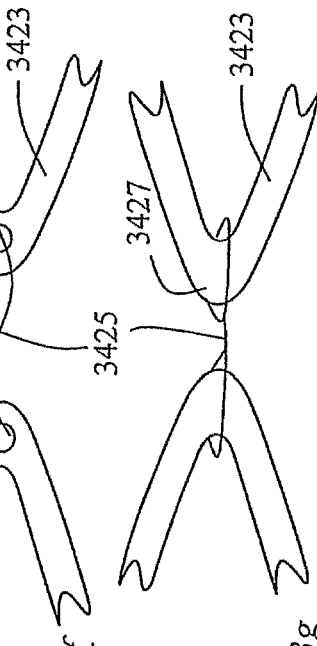
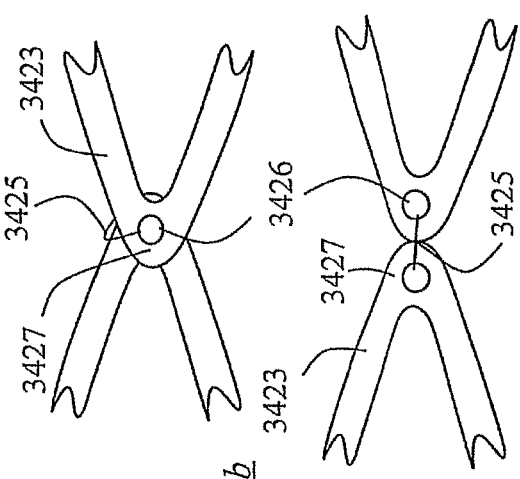
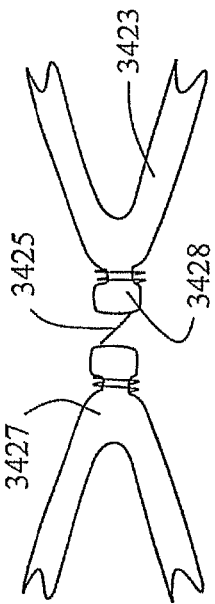
Fig. 43a
Fig. 43b
Fig. 43c
Fig. 43d
Fig. 43e
Fig. 43f
Fig. 43g
Fig. 43h

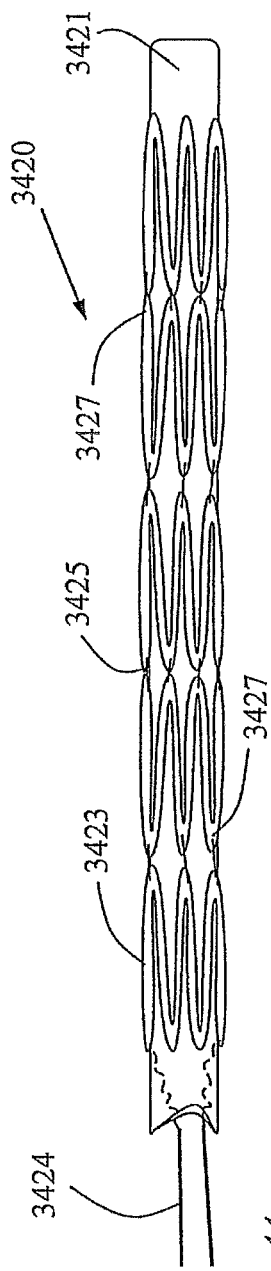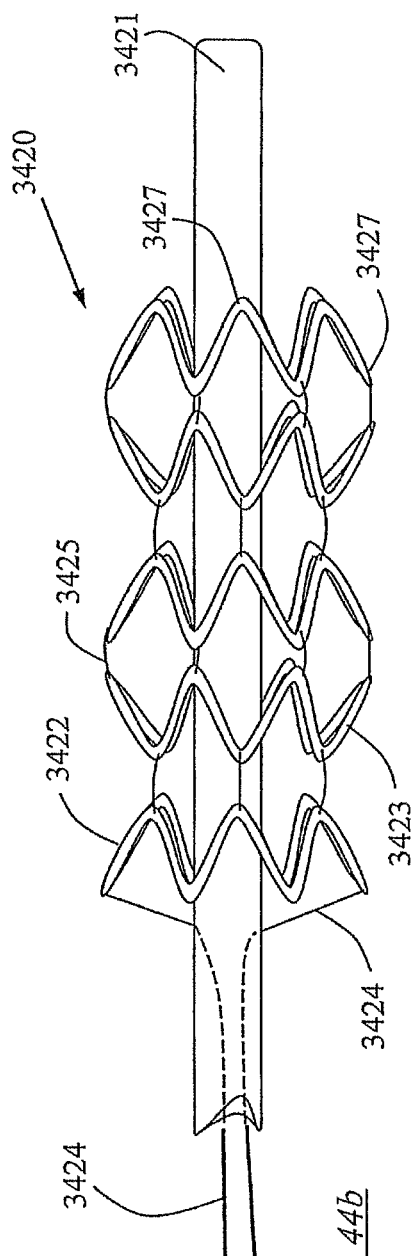
Fig. 44a
Fig. 44b

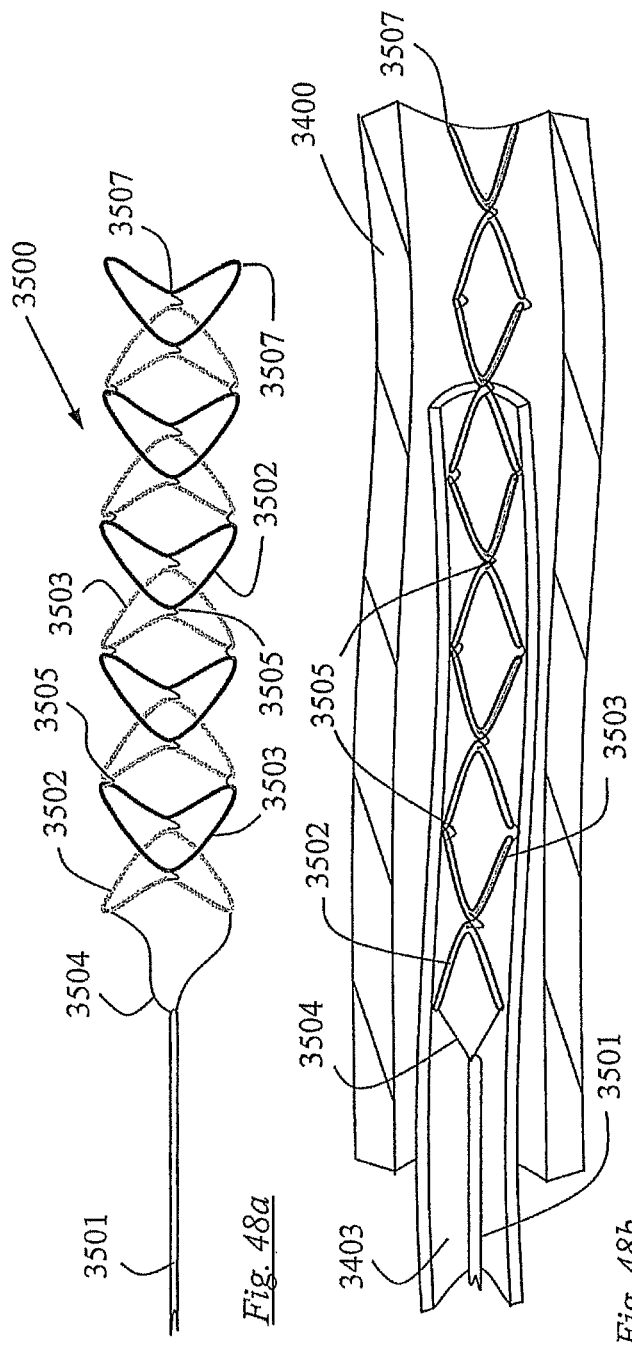

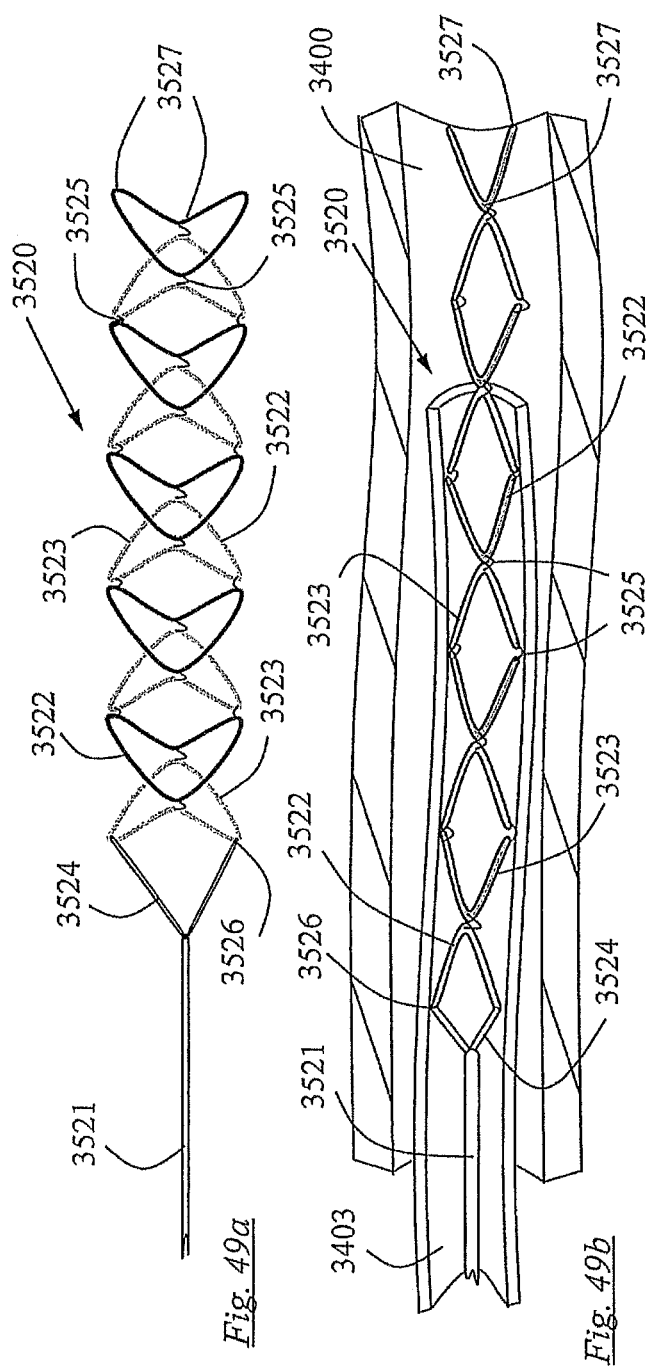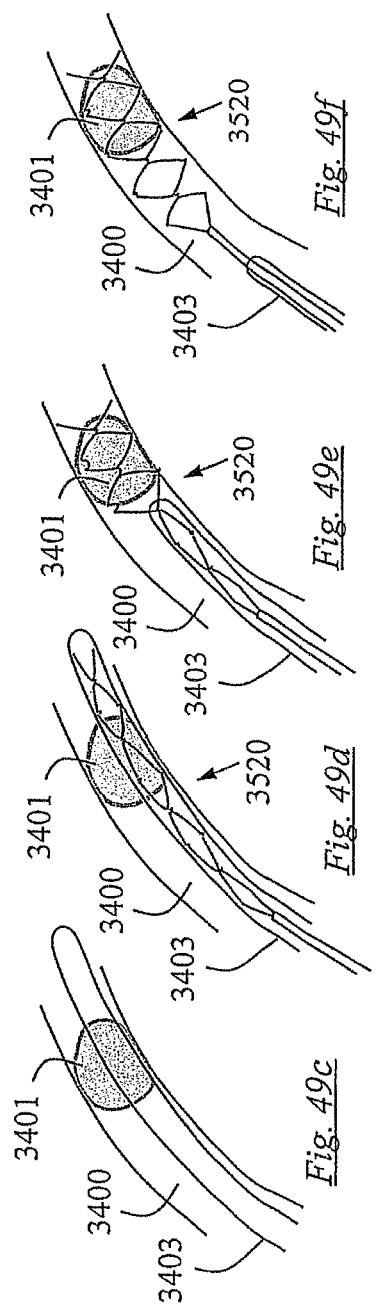

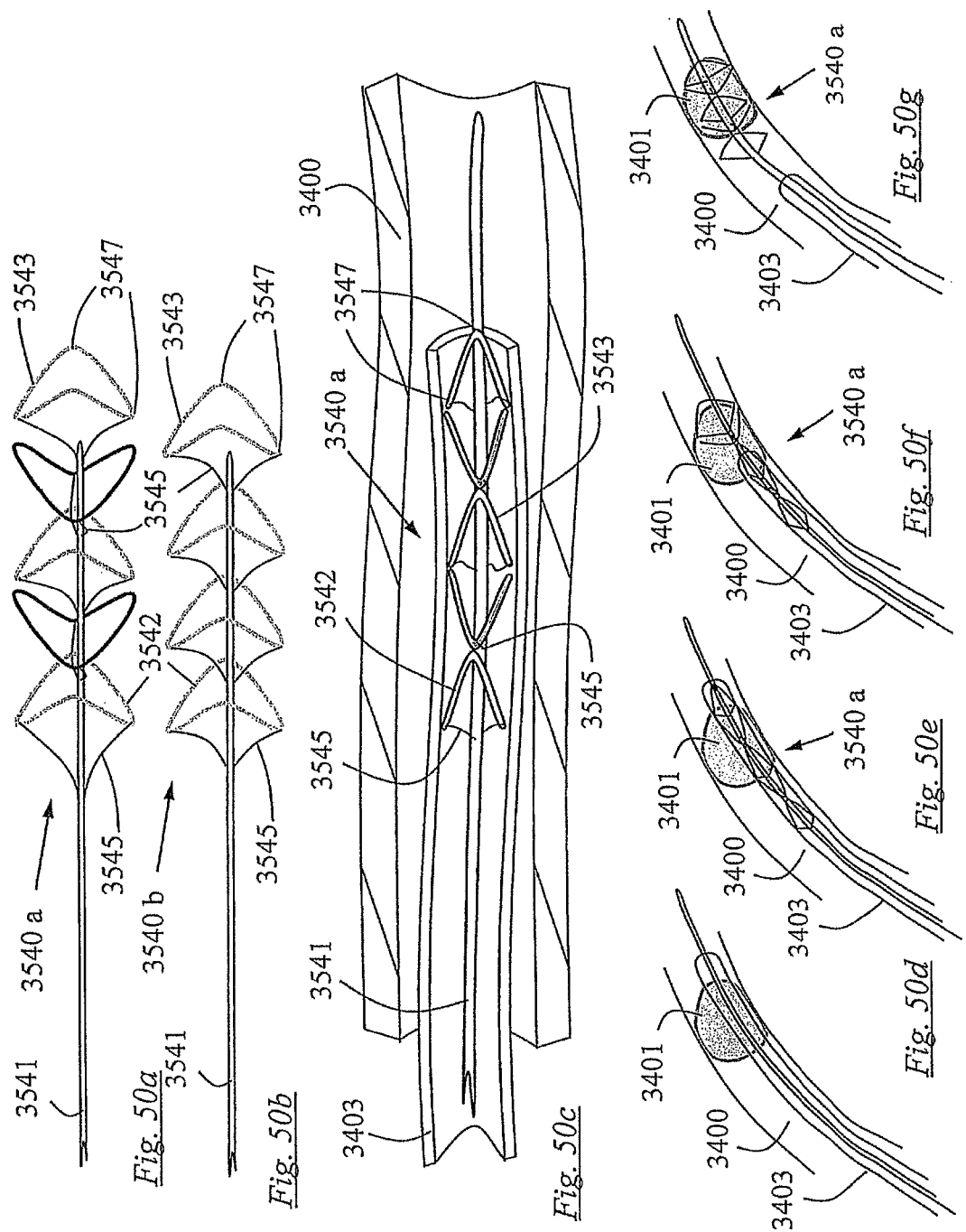

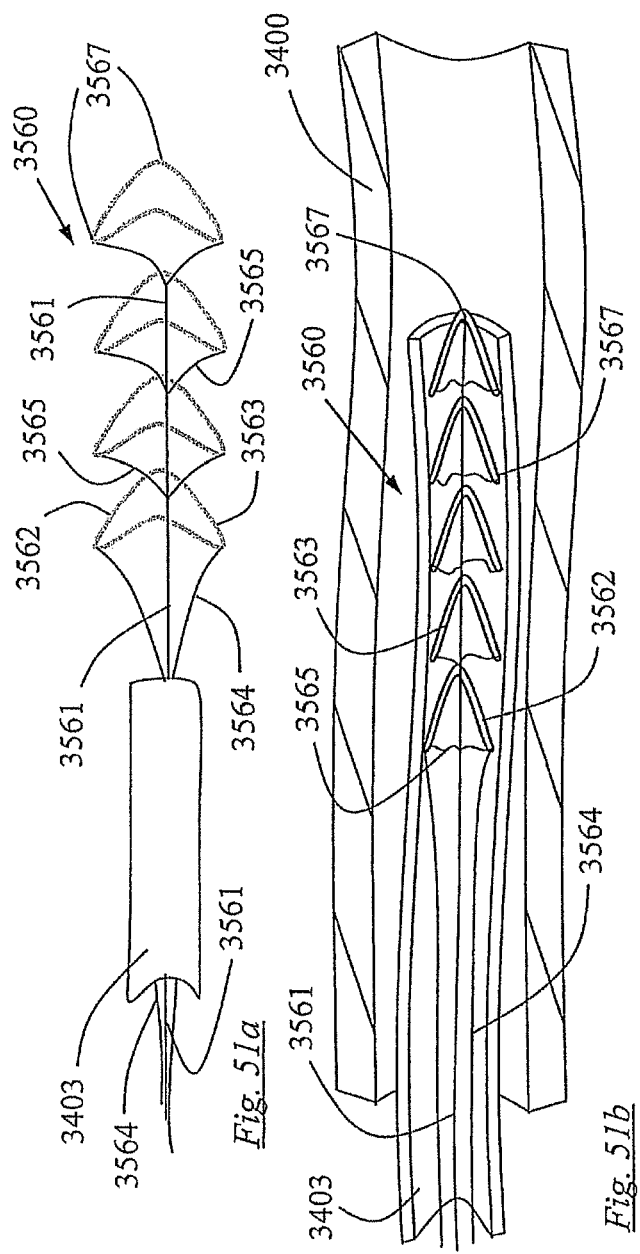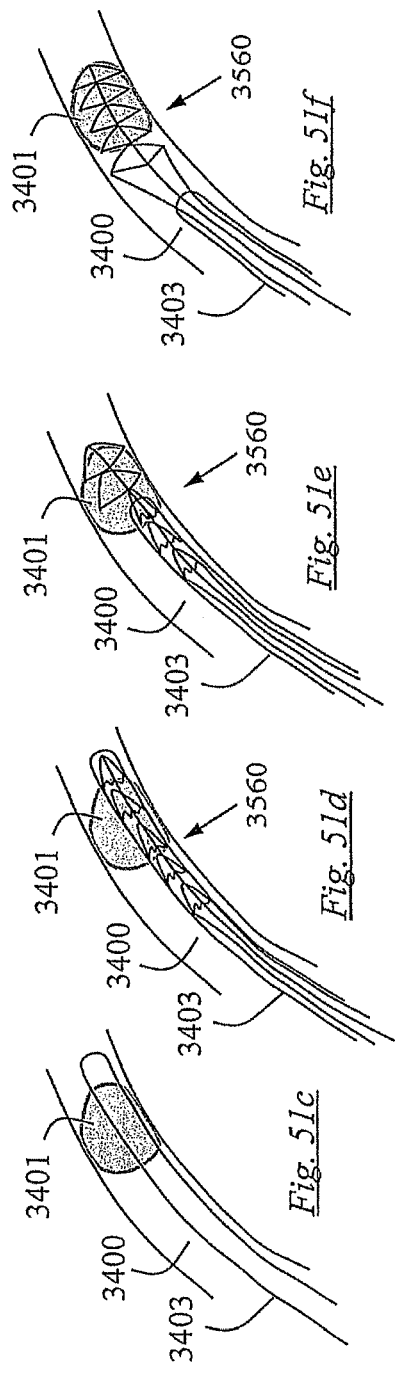

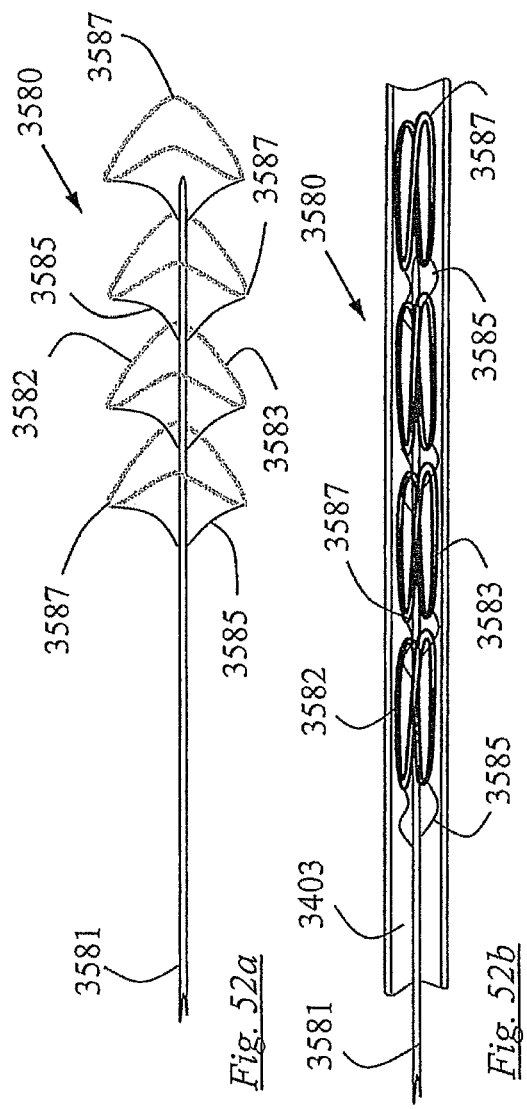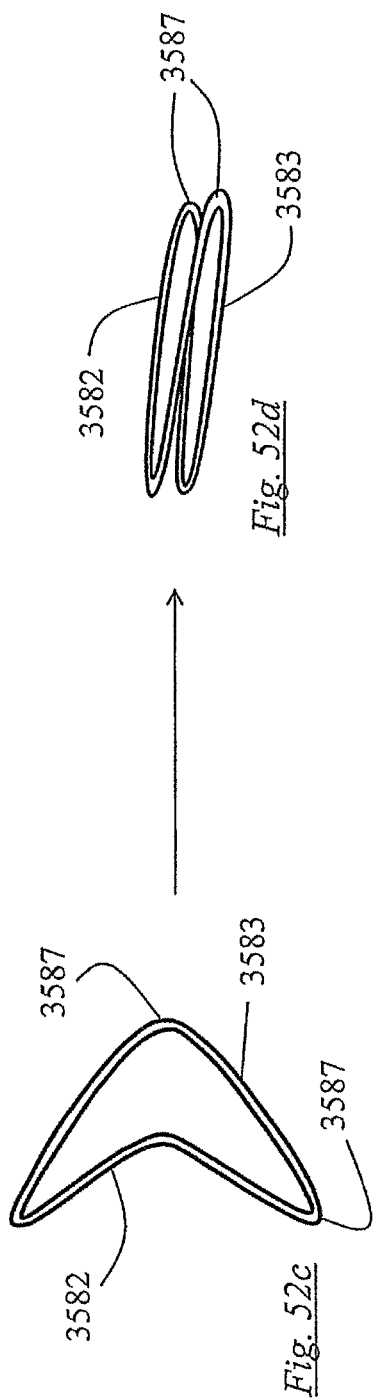

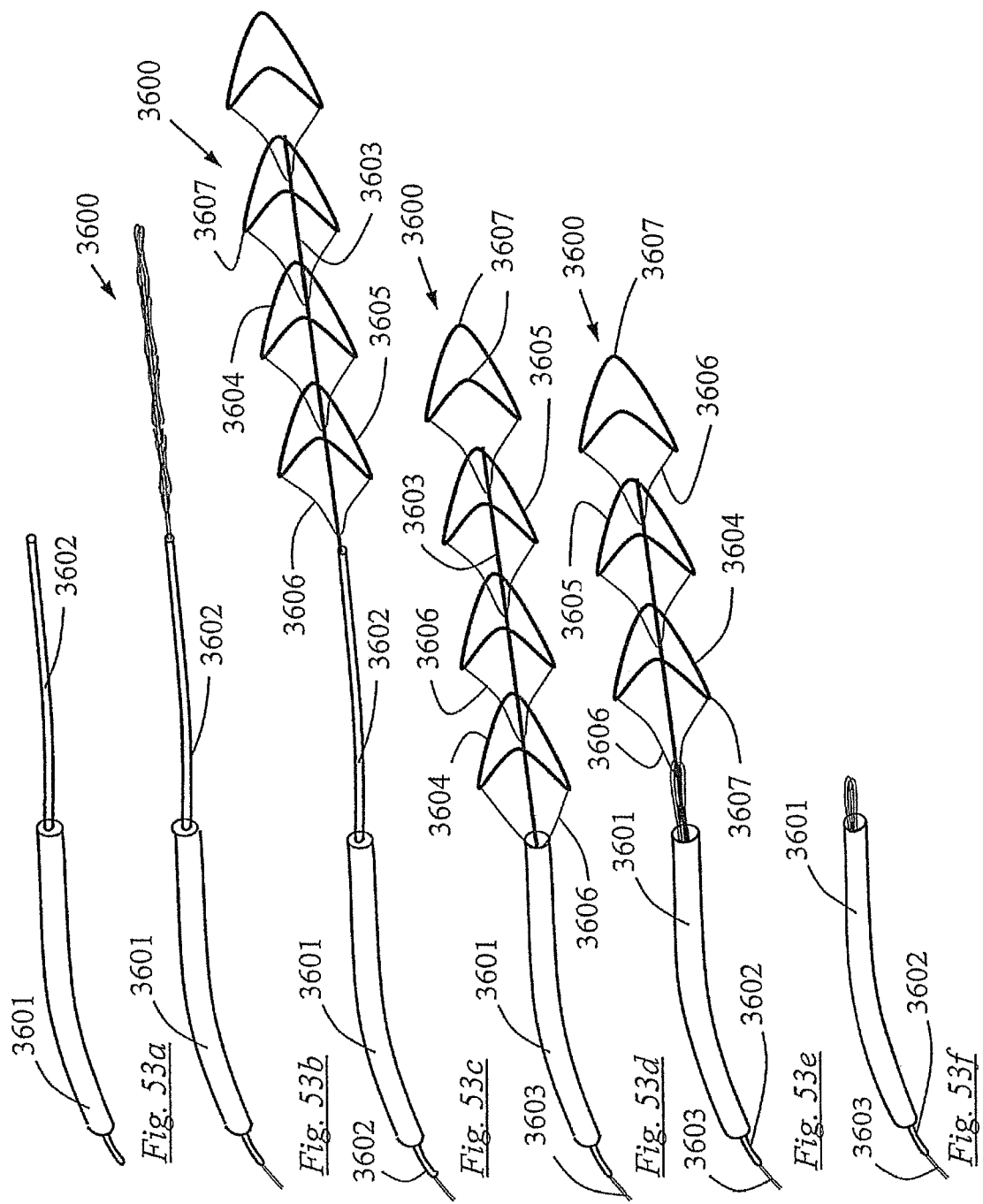

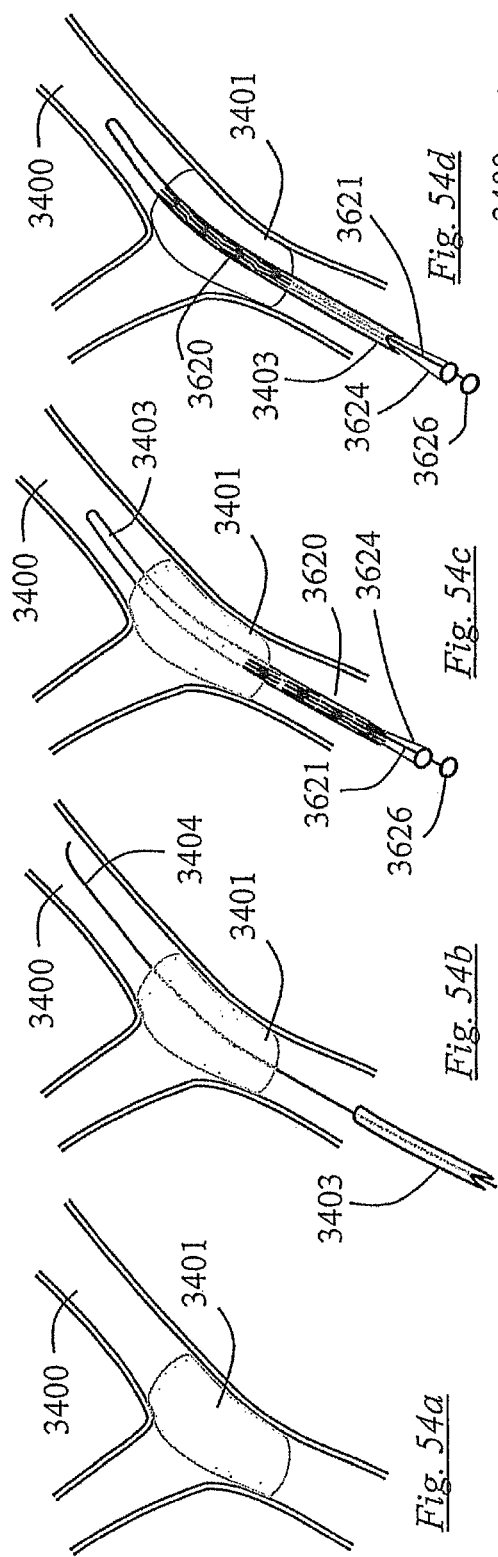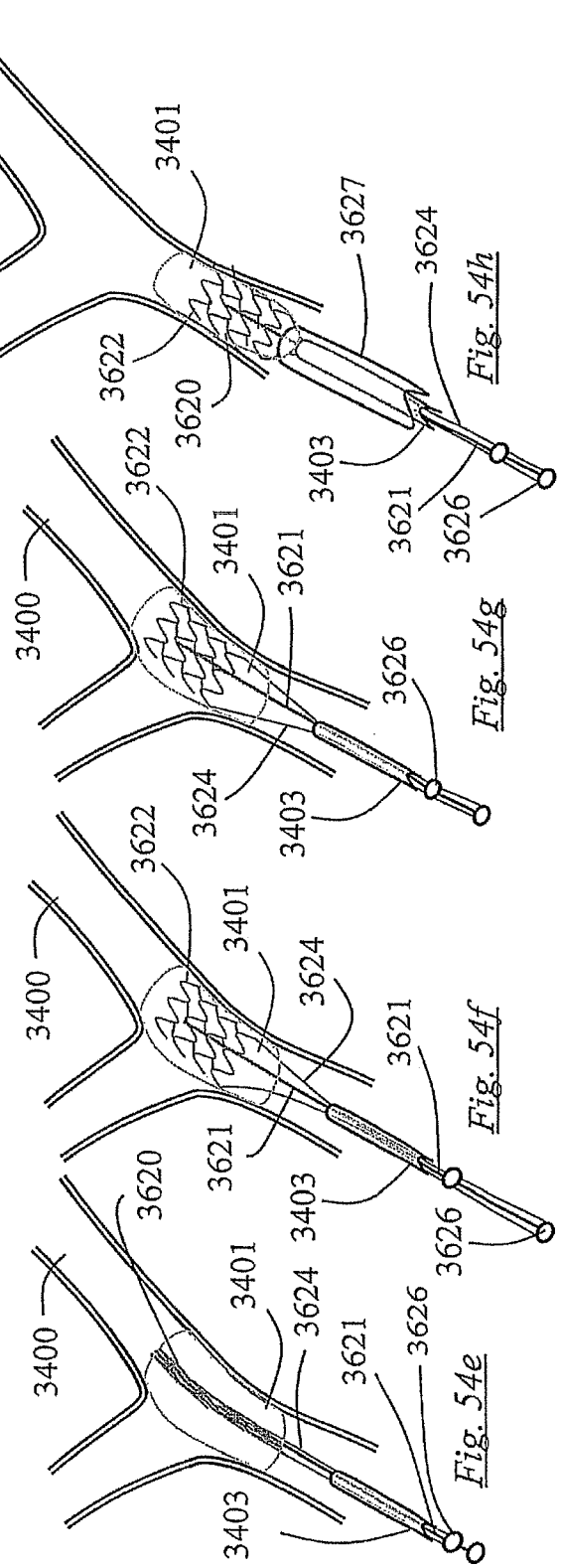

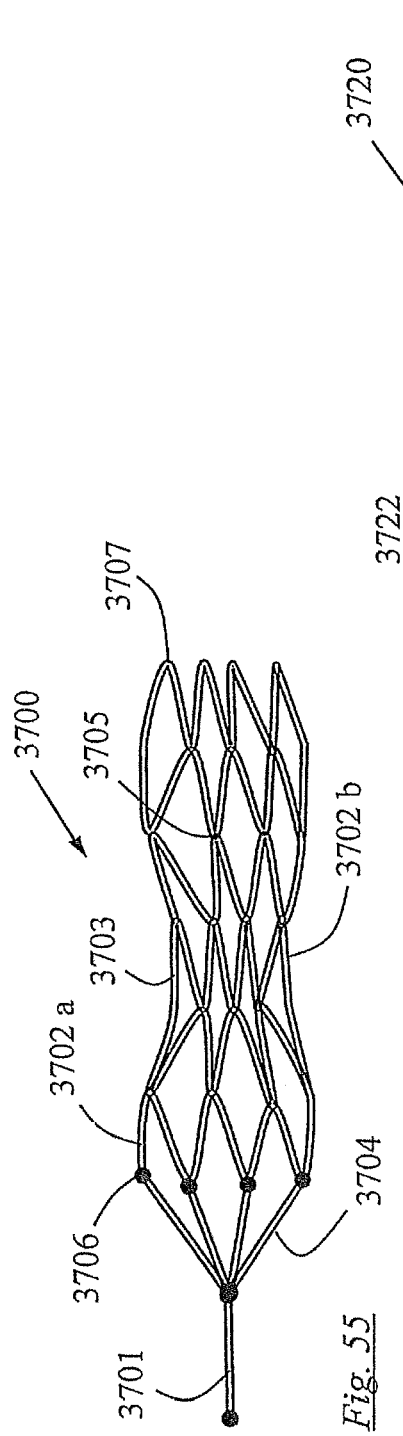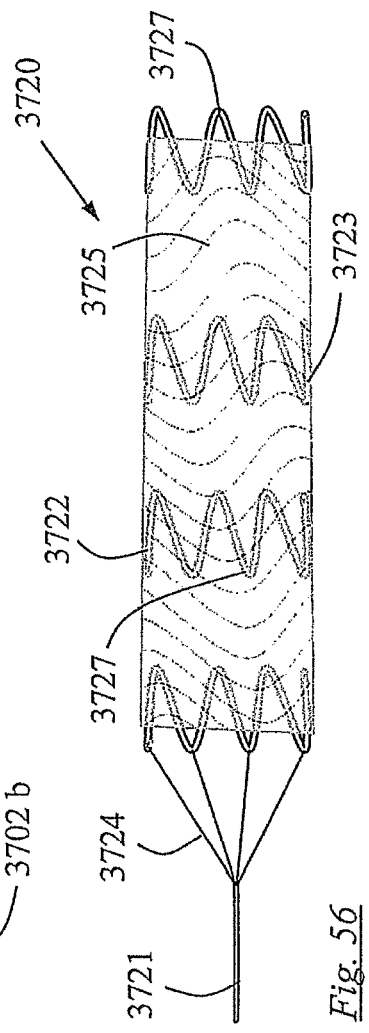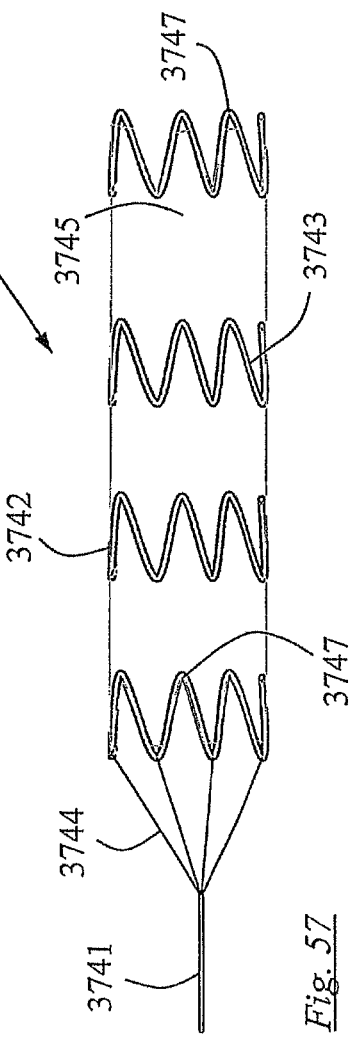
Fig. 55
Fig. 56
Fig. 57

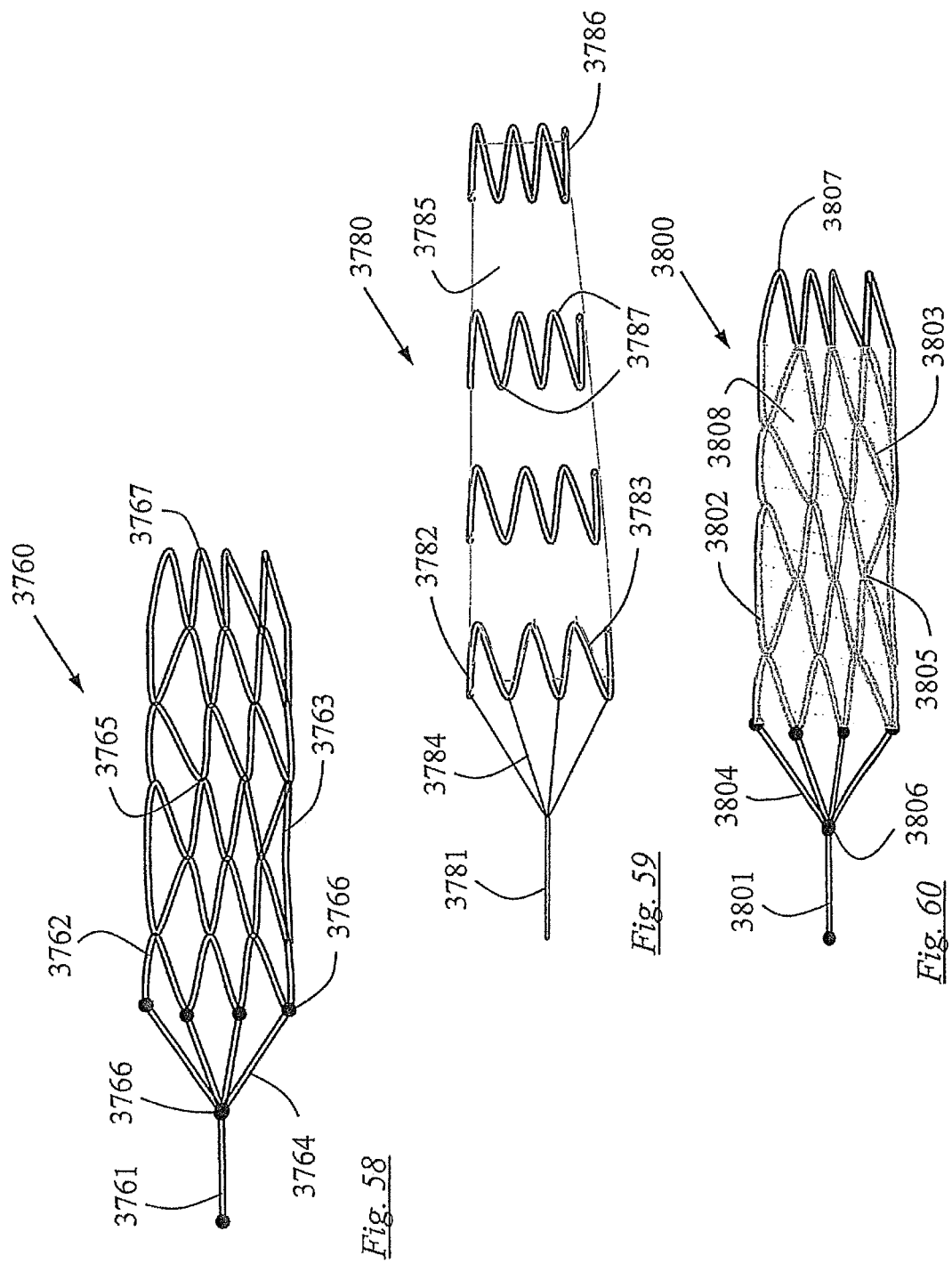

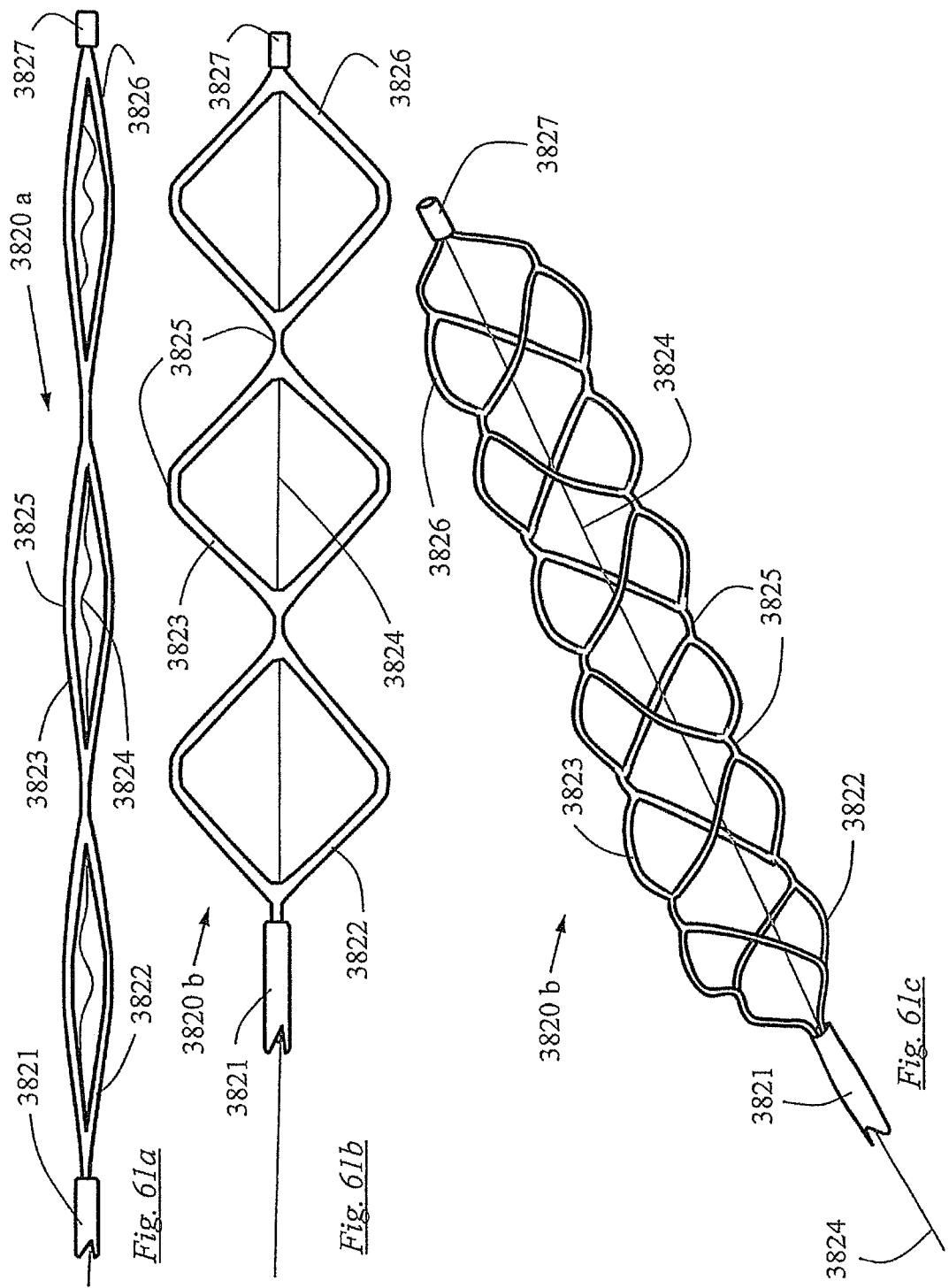

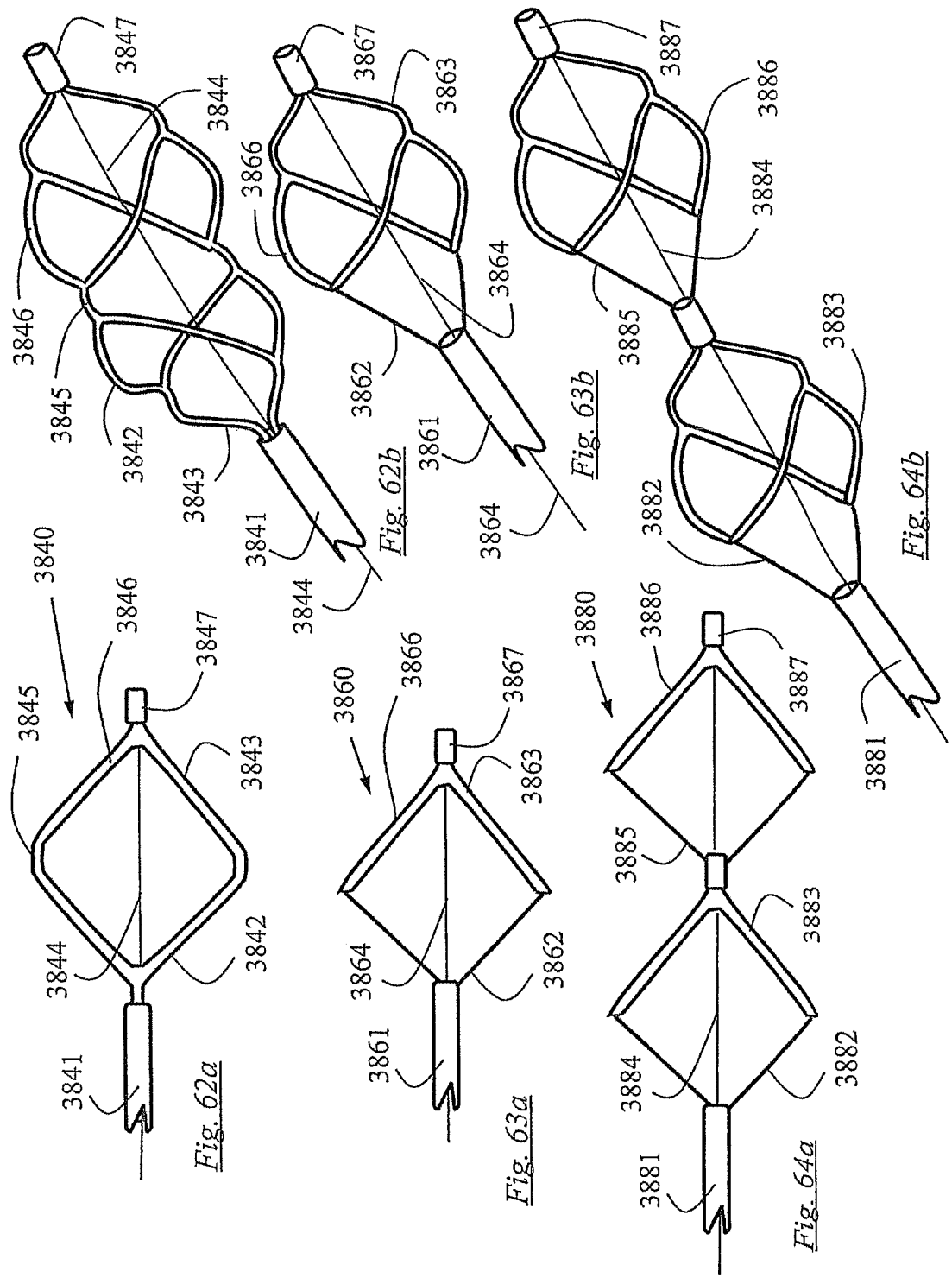

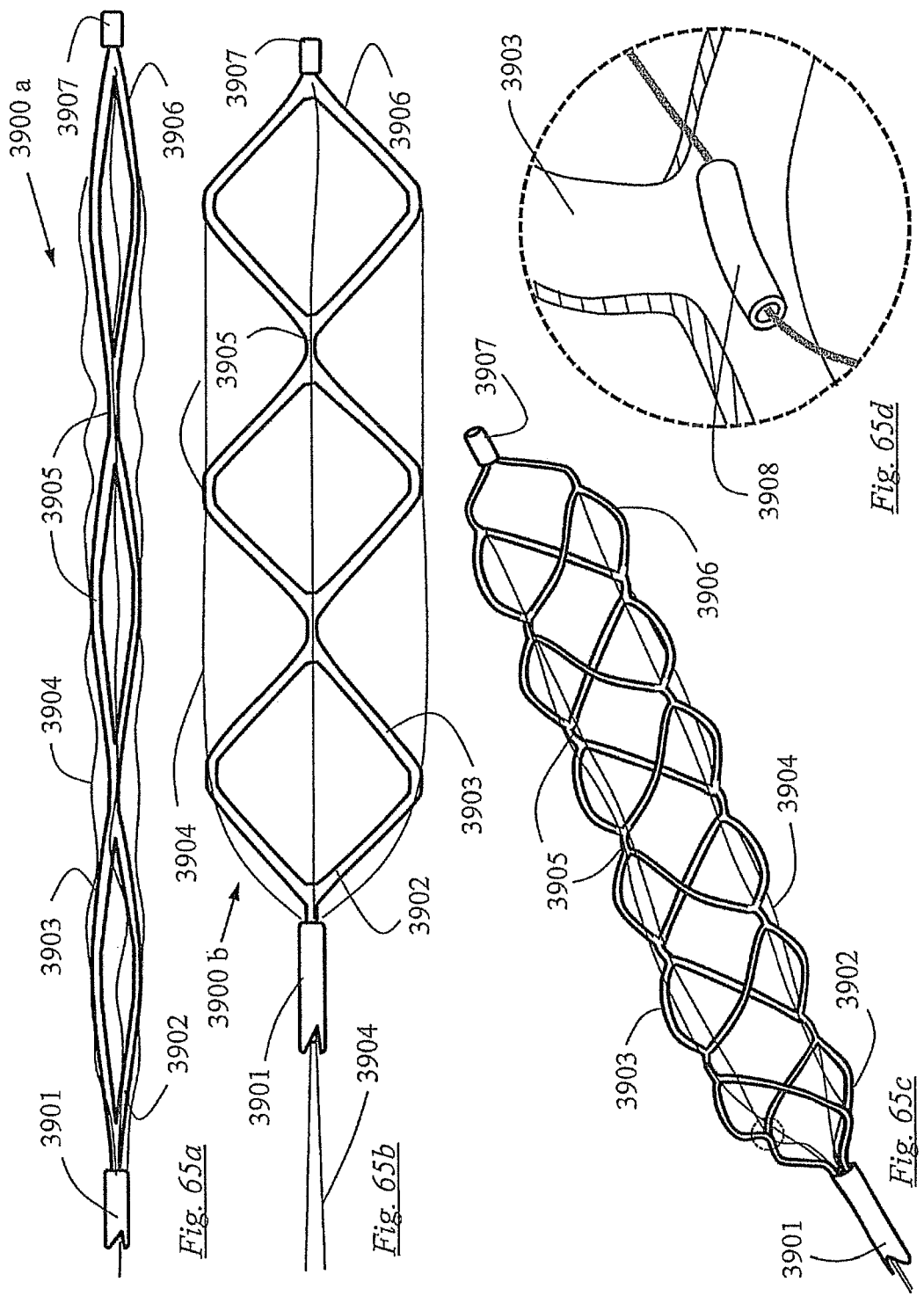

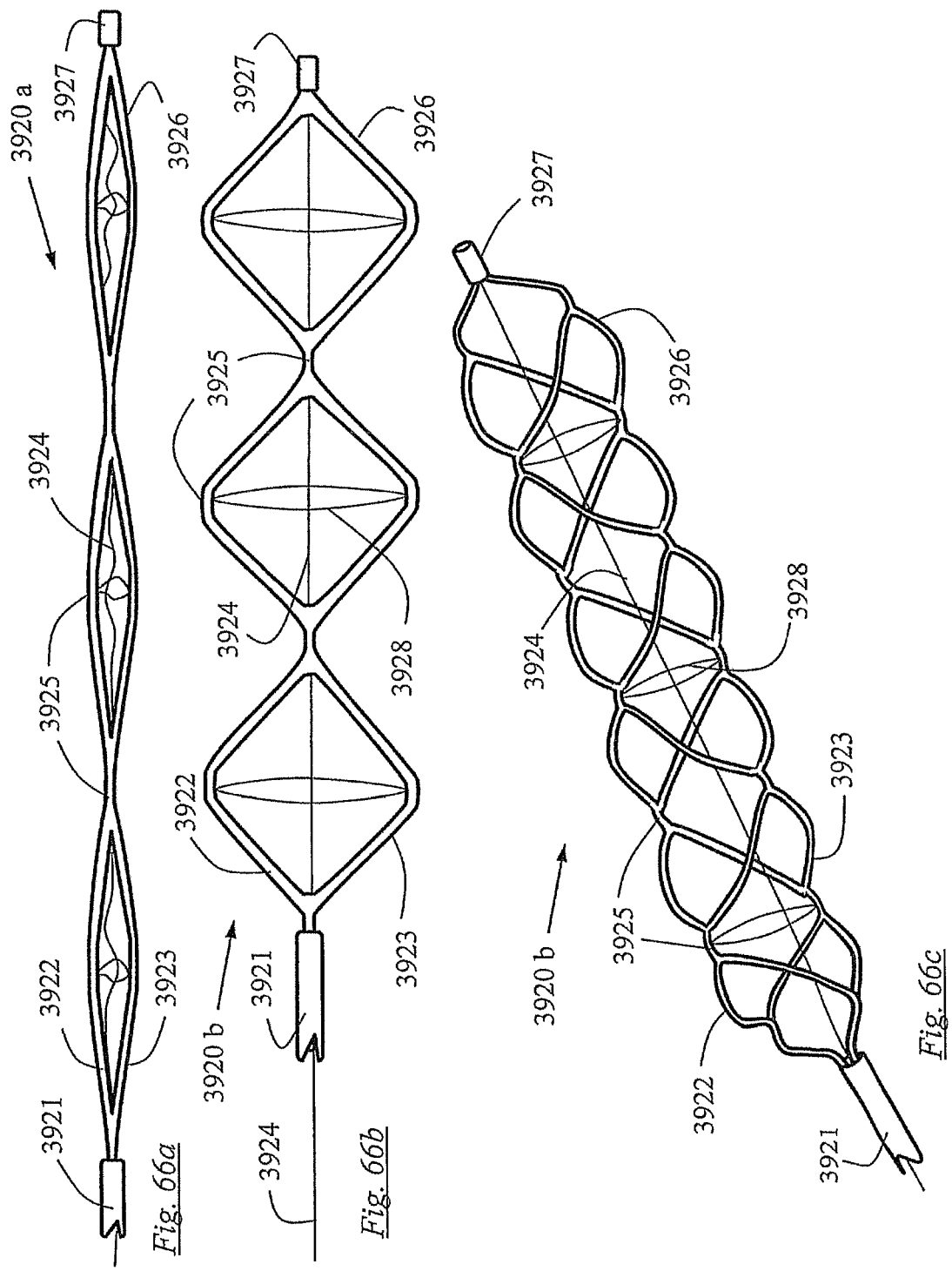

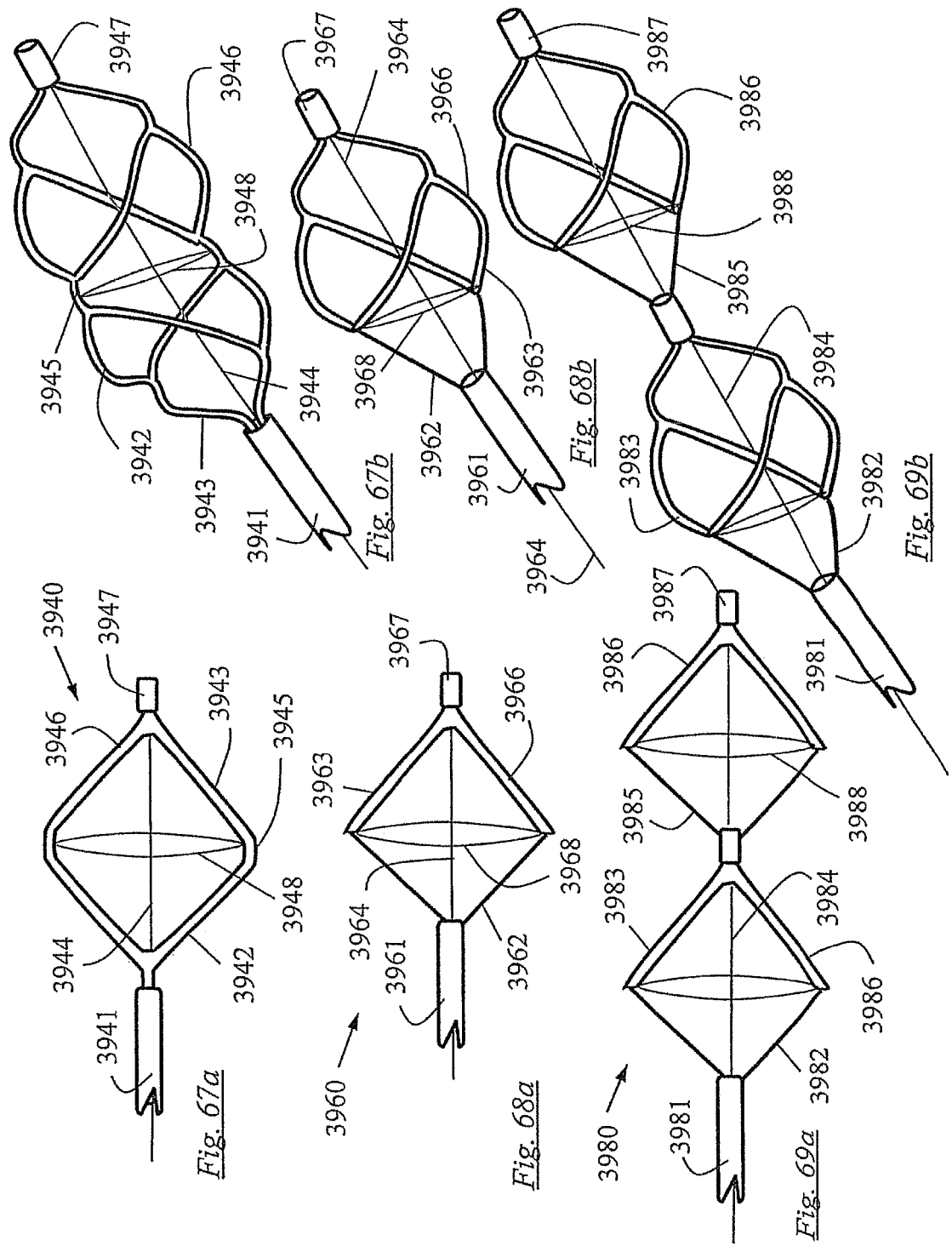

CLOT RETRIEVAL DEVICES

CROSS REFERENCE TO RELATED APPLICATIONS

The present application is a continuation application of U.S. patent application Ser. No. 15/226,389 filed Aug. 2, 2016, which is a continuation application of U.S. patent application Ser. No. 13/829,684 filed Mar. 14, 2013, now U.S. Pat. No. 9,433,429 issued Sep. 6, 2016. The entire contents of which are hereby incorporated by reference.

FIELD OF THE INVENTION

The present invention relates generally to the field of distal mechanical thrombectomy, more particularly, to a self-expandable mechanical clot retrieval device used in the treatment of acute ischemic stroke and pulmonary embolism in a patient. The retrieval device is of extremely small size delivered through an intravascular microcatheter and meticulously designed to remain in a collapsed state while advancing through the microcatheter to remove thrombus or embolus from the blocked arteries.

DISCUSSION OF THE PRIOR ART

Acute ischemic stroke remains one of the major causes of death and disability worldwide. It refers to stroke caused by thrombosis or embolism creating an acute blockage in vasculature that stops flow of blood and deprives the surrounding brain tissue of oxygen. In the absence of oxygen, the brain cells of the immediate area begin to die and release a cascade of toxic chemicals that threaten brain tissue in the surrounding area.

Similarly, pulmonary embolism is a common and potentially fatal condition, creating a sudden blockage in a lung artery caused by any naturally occurring embolus traveling through the arteries of the lung and occluding a small artery that stops the flow of blood and deprives the surrounding lung tissue of oxygen. In the absence of oxygen, the lung tissues in the immediate area succumb to lysis as they are unable to process sufficient oxygen into the blood.

Importantly, both acute ischemic stroke and pulmonary embolism can be avoided and treated by removing the acute blockage and restoring blood flow to the affected area. In recent years, significant advances have been made to prevent ischemic stroke and pulmonary embolism through endovascular procedures involving the use of distal mechanical clot retrieval devices on the end of catheters to manually retract clot and fragments of clot.

Generally, the distal mechanical devices are delivered endovascularly and advanced by guidewire and microcatheter until the device is located distal of the clot where it expands. Thus force is applied to the distal surface of the clot to dislodge it from the artery wall where it is caught and retracted proximally by the retrieval device.

Despite continuous advances made in the art of distal mechanical thrombectomy, there is still much room for improvement in effectively removing acute blockage particularly in engaging and retracting thrombus or embolus from extremely small vasculature. The present invention is an efficient and meticulous approach to improve upon the distal mechanical thrombectomy.

SUMMARY OF THE INVENTION

Various aspects of the present invention concern a self-expandable mechanical clot retrieval device that effectively and reliably removes thrombus or embolus from blocked vasculature. It is designed variously to dislodge, engage and retract blood clot from extremely small and tortuous vasculature. The retrieval device comprises an elongate member and a plurality of ring elements. The ring elements may comprise a plurality of struts and crowns interconnected by a tether formed at a distal end of the elongate member or may be a separate component attached thereto. In one aspect, at least one tether connects each ring element to the elongate member to restrain the ring element in a collapsed configuration during delivery of the retrieval device through an intravascular microcatheter. The tether connecting the ring element to the elongate member disengages when the retrieval device is positioned at the occluded site and the microcatheter is retracted to allow the self-expandable ring elements to reach an expanded configuration. Preferably, the self-expandable ring elements are formed of shape memory material such as Nitinol.

Additional aspects of the present invention concern methods of using the mechanical clot retrieval device described in the previous paragraph. It is used in the treatment of acute ischemic stroke and pulmonary embolism in a patient. The method of removing the blood clot from a blocked artery includes advancing a self-expandable mechanical clot retrieval device having an elongate member and a plurality of self-expandable ring elements arranged at a distal end of the elongate member through the vasculature to a blockage site in the artery. The retrieval device bypasses the clot and is positioned distal to the clot to allow the self-expandable ring elements to reach an expanded configuration in order to engage the clot within expanded ring elements and is proximally retracted from the artery. The method may include retracting the expanded ring elements proximally into a guide catheter or a microcatheter.

STATEMENT OF THE INVENTION

In a first embodiment of the invention the clot retrieval device comprises an elongate member and a plurality of clot engaging elements at a distal end of the elongate member, the clot engaging elements being self expandable and having a retracted delivery configuration and an expanded deployed configuration; and a biasing element for biasing the clot engaging elements into a retracted delivery configuration against the elongate member; the biasing element being releasable to allow the clot engaging elements to expand into the deployed configuration.

The second embodiment of the invention comprises a method of retrieving a clot comprising the steps of: (1) providing an elongate member and a plurality of clot engaging elements at a distal end of the elongate member, the clot engaging elements having a retracted configuration and an expanded configuration: (2) providing a biasing element for retaining the clot engaging elements in the retracted configuration; (3) advancing a microcatheter across a clot; (4) advancing the elongate member with the clot engaging elements in a retracted configuration through the microcatheter so that at least some of the clot engaging elements are distal of the clot; (5) releasing the biasing so that the clot engaging elements expand to the expanded configuration; (6) engaging the clot engaging elements with a clot; and (7) using the clot engaging elements, drawing the clot into a retrieval element.

A third embodiment of the invention comprises a luminal prosthesis device comprising: an elongate member and a plurality of luminal prosthetic elements at a distal end of the elongate member; the luminal prosthetic elements being self expandable and having a retracted delivery configuration and an expanded deployed configuration; and a biasing element for biasing the luminal prosthetic elements into a retracted delivery configuration against the elongate member; the biasing element being releasable to allow the luminal prosthetic elements to expand into the deployed configuration.

A fourth embodiment of the invention comprises a clot retrieval device comprising: an elongate member and a plurality of clot engaging elements at a distal end of the elongate member, the clot engaging elements being self expandable and having a retracted delivery configuration, a retracted deployed configuration and a fully expanded configurations; and providing a release element for biasing the clot engaging elements in at least one retracted configuration; activation of the release element allowing the clot engaging elements to expand into the fully expanded configuration.

In one variation of this embodiment the diameter of the clot engagement elements in the retracted delivery configuration is smaller than the diameter of the clot engagement elements in the retracted deployed configuration and the diameter of the clot engagement elements in the retracted deployed configuration is smaller than the diameter of the clot engagement elements in the fully expanded configuration.

In another variation of this embodiment a release element is configured to bias the clot engaging elements in a retracted deployed configuration. The release element may be integral with the clot engagement elements. The release element may be integral with elongate member. The release element may be connected to either the clot engagement elements, the elongate member or to both. The release element may comprise; a snap element, a restraining element, a tether, an interlocking element, an overlapping element of the clot engagement element, an abutment element, a connector element, a housing element, a pair of interacting elements, or a limiting element configured to limit at least one degree of expansion movement.

In another variation of this embodiment the clot engagement element comprises a plurality of struts and said release element is configured to limit relative movement between at least a pair of said struts. In another variation of this embodiment the release element is configured to limit relative movement between the clot engagement element and the elongate member. The elongate member may be configured to activate the release element.

In another variation of this embodiment the device comprises an activation element said activation element configured to affect the release of the release element. The activation element may comprise an elongate tube, an elongate member, or a tether.

A fifth embodiment of the invention comprises a clot retrieval device comprising: an elongate member and a first clot engaging element and a second clot engaging element the first clot engaging element distal of the second clot engaging element, the clot engaging elements being self expandable and having a sheathed delivery configuration, a deployed configuration and a fully expanded configurations; and providing at least one release element for biasing the clot engaging elements in the deployed configuration; activation of the at least one release element allowing the clot engaging elements to expand into the fully expanded configuration.

In one variation of this embodiment the sheathed configuration comprises sheathing within the lumen of a microcatheter. In another variation of this embodiment the unsheathing the clot engaging elements allows the clot engaging elements to assume the unsheathed configuration. In another variation of this embodiment the diameter of the clot engaging elements in the deployed configuration is greater than the diameter of the clot engaging elements in the sheathed configuration. In another variation of this embodiment the first clot engagement element assumes the expanded configuration while the second clot engaging element is in the deployed configuration.

A sixth embodiment of the invention comprises a method for retrieval of a clot comprising the steps of: (1) providing a clot retrieval device the clot retrieval device comprising an elongate member and a plurality of clot engaging elements at a distal end of the elongate member, the clot engaging elements having a retracted configuration, a partially expanded configuration and an expanded configuration; (2) providing a biasing element for limiting the expansion of the clot engaging elements; (3) advancing a microcatheter across a clot; (4) advancing the elongate member with the clot engaging elements in a retracted configuration through the microcatheter so that at least some of the clot engaging elements are distal of the clot; (5) retracting the microcatheter so as to unsheathe at least one clot engaging element, (6) activating the biasing element so as to trigger the expansion of at least one of said clot engagement elements to the expanded configuration, (7) retracting the clot retrieval device and the clot into a proximal retrieval element.

In one variation of this embodiment the method comprises the step of retracting the microcatheter also comprises the step of expanding the at least one clot engagement element to the partially expanded configuration. In another variation of this embodiment the step of activating the biasing element comprises the step of applying an activation force to the biasing element.

In another variation of this embodiment the step of activating the biasing element comprises the step of applying a compressive, tensile, twisting or radial force to the biasing element.

In another variation of this embodiment the method comprises the step of providing a plurality of clot engagement elements configured such that in the partially expanded configuration a flow lumen extends through the centre of said clot engagement elements, said lumen being larger than the diameter of the microcatheter and smaller than the diameter of the vessel.

In another variation of this embodiment the method comprises the step of holding the clot retrieval device steadfast in the vessel for a dwell time period the dwell time period comprising at least one minute.

A seventh embodiment of the invention comprises a retrieval device for removing occlusive clot from the vasculature the retrieval device comprising: an elongate member and an expandable body connected to the elongate member, the expandable body comprising a plurality of self-expanding clot engaging elements, each clot engaging element comprising a plurality of struts and a plurality of crowns arranged to form at least one ring, at least one of said plurality of crowns comprising an integral connection to an adjacent ring, a spacing between at least two of said clot engaging elements said spacing comprising a variable spacing in use.

In one variation of this embodiment the at least one integral connection comprises a monolithic connection. The at least one integral connection may comprise a connection to a crown of an adjacent ring of the same clot engaging element. The at least one integral connection may comprise a connection to a crown of a ring of an adjacent engaging element. The at least one integral connection may comprise a connection to the elongate member. In another variation of this embodiment the at least one of said plurality of crowns comprises an unconnected crown.

In another variation of this embodiment the a pair of adjacent crowns of said expandable body comprise a pair of unconnected crown, the first of said pair of adjacent crowns comprising a proximally facing crown and the second of said pair of adjacent crowns comprising a distally facing crown. The first crown of said pair of adjacent crowns may be located on a first clot engaging element and the second crown of said pair of adjacent crowns may be located on a second clot engaging element.

In another variation of this embodiment the clot engaging elements are arranged in series. In another variation of this embodiment the clot engaging elements are arranged in series.

In another variation of this embodiment the clot engagement elements are spaced apart. The spacing between at least two of said clot engaging elements may vary during delivery. The spacing between at least two of said clot engaging elements may vary during engagement with the clot. The spacing between at least two of said clot engaging elements may vary during clot disengagement with the vessel wall. The spacing between at least two of said clot engaging elements may vary during withdrawal of the clot through the vasculature. The spacing between at least two of said clot engaging elements may vary during removal of the clot and device into the lumen of a retrieval catheter. The spacing between at least two of said clot engaging elements may vary across the diameter of the clot engaging elements.

An eighth embodiment of the invention comprises a retrieval device for removing occlusive clot from the vasculature comprising: an elongate member and an expandable body connected to the elongate member, the expandable body comprising an collapsed delivery configuration and an expanded configuration, the expandable body comprising a plurality of self-expanding clot engaging elements, cut from a tube in a monolithic structure, each clot engaging element comprising a plurality of struts and a plurality of crowns arranged to form a ring, at least one pair of adjacent clot engaging elements being spaced apart by a plurality of connector elements, the pair of adjacent clot engaging elements and the plurality of connectors configured to create a plurality of clot engaging cells, the plurality of connectors comprising a plurality of helical strut.

In one variation of this embodiment the plurality of clot engaging cells are configured to scaffold outwardly so as to create a flow lumen through the clot. The plurality of clot engaging cells may be configured to urge clot ingress through the cell openings so that the clot is interlaced with the plurality of engaging cells.

In another variation of this embodiment the helical struts extend circumferentially through an angle of at least 25 degrees. In another variation of this embodiment the helical struts extend circumferentially through an angle of at least 40 degrees. In another variation of this embodiment the helical struts extend circumferentially through an angle of at least 50 degrees. In another variation of this embodiment the helical struts extend axially a distance of at least 500 micrometers. In another variation of this embodiment the helical struts extend axially a distance of at least 750 micrometers. In another variation of this embodiment the helical struts extend axially a distance of at least 900 micrometers.

In another variation of this embodiment the tube from which the expandable body is cut has a diameter larger than the diameter of the expandable body in the collapsed delivery configuration. The tube from which the expandable body is cut may have a diameter equal to or smaller than the expanded diameter of the expandable body.

A ninth embodiment of the invention comprises a mechanical clot retrieval device for use in a blood artery, comprising an elongate member having a distal end and a proximal end, wherein the distal end extends interior of the artery and the proximal end extends exterior of the artery; and a plurality of self-expandable ring elements configured at the distal end of the elongate member, wherein each ring element, comprising a plurality of struts, is interconnected by ring connecting tethers and is delivered through an intravascular microcatheter in a collapsed configuration inside the artery, wherein the ring elements comprise a radial force biasing ring elements toward an expanded configuration, wherein the radial force is absorbed by the elongate member in the collapsed configuration, wherein the microcatheter is retracted proximally allowing the ring elements reach the expanded configuration.

In one variation of this embodiment each strut comprises a crown element. The crown element may comprise an engagement member and a fixed tab. The crown element may comprise an engagement member and an engagement hook. The crown element may comprise an engagement member and a connector. The crown element may comprise an engagement member and an engagement tab. The crown element may engage a neighboring crown element in a snap-fit mechanism.

In another variation of this embodiment the snap-fit mechanism restrains the ring elements in the collapsed configuration. The ring elements in the collapsed configuration may be substantially parallel along the longitudinal axis of the elongate member. In another variation of this embodiment the device comprises a proximal fixed collar configured proximally of the ring elements. In another variation of this embodiment the device further comprises a push tube attached to the proximal fixed collar.

In another variation of this embodiment the device further comprises a distal moveable collar configured distally of the ring elements. In another variation of this embodiment the device comprises a balloon. In another variation of this embodiment the balloon is delivered in a deflated state. In another variation of this embodiment the device further comprises a ball element. In another variation of this embodiment the device further comprises a pair of pull tethers having distal and proximal ends. In another variation of this embodiment the distal ends are connected to the most proximal ring element. In another variation of this embodiment the distal ends are attached to the connector. In another variation of this embodiment the distal ends are attached to the engagement tab.

In another variation of this embodiment the distal ends are attached to the distal movable collar. In another variation of this embodiment the proximal ends extend exterior of the artery. The proximal ends may be manually pulled proximally to disengage the snap-fit mechanism. The proximal ends may be attached to the elongate member. In another variation of this embodiment the balloon is inflated to disengage the snap-fit mechanism. In another variation of this embodiment the ball element is manually retracted proximally to disengage the snap-fit mechanism.

A tenth embodiment of the invention comprises a mechanical clot retrieval device for use in an artery, comprising an elongate member having a distal end and a proximal end, wherein the distal end extends interior of the artery and the proximal end extends exterior of the artery;

and a plurality of self-expandable ring elements configured at the distal end of the elongate member, wherein each ring element, comprising a plurality of struts, is attached to the elongate member by connecting tethers and is delivered through an intravascular microcatheter in a collapsed configuration, wherein the ring elements comprise a radial force biasing the ring elements toward an expanded configuration, wherein the radial force is absorbed by the elongate member in the collapsed configuration, wherein the microcatheter is retracted proximally allowing the ring elements to reach the expanded configuration.

In one variation of this embodiment each strut comprises a crown element. In another variation of this embodiment the proximally facing crown element is a ring proximal crown and distally facing crown element is a ring distal crown. The ring proximal crown may be attached to the elongate member by connecting tethers. The crown element may be engaged with the elongate member in a snap-fit mechanism. The snap-fit mechanism restrains the ring elements in the collapsed configuration. The elongate member is manually retracted to disengage the snap-fit mechanism. In another variation of this embodiment the elongate member is attached to at least one ring element in the expanded configuration.

A eleventh embodiment of the invention comprises a mechanical clot retrieval device for use in an artery, comprising an elongate member having a distal end and a proximal end, wherein the distal end extends interior of the artery and the proximal end extends exterior of the artery; and a plurality of self-expandable ring elements configured at the distal end of the elongate member, wherein each ring element comprising a plurality of struts is interconnected by ring connecting tethers and is delivered through an intravascular microcatheter in a collapsed configuration, wherein the ring elements comprise a radial force biasing the ring elements toward an expanded configuration, wherein the microcatheter is retracted allowing the ring elements to reach the expanded configuration.

In one variation of this embodiment each strut comprises a crown element. The crown element may be attached to the elongate member by a bonding agent. The bonding agent restrains the ring elements in the collapsed configuration. The bonding agent may be dissolved in vivo allowing the ring elements reach the expanded configuration. The radial force may be absorbed by the bonding agent.

In another variation of this embodiment the crown element is attached to the elongate member by a resorbable covering. The re-absorbable covering restrains the ring elements in the collapsed configuration. The re-absorbable covering may be dissolved in vivo allowing the ring elements to reach the expanded configuration. The radial force may be absorbed by the re-absorbable covering. In another variation of this embodiment the device comprises a pair of pull tethers having distal and proximal ends. The distal ends of said tethers are attached to most the proximal ring element. The proximal ends of said tethers extend exterior of the artery.

An twelfth embodiment of the invention comprises a mechanical clot retrieval device for use in vasculature, comprising an elongate member having a distal end, a proximal end and a plurality of radial pins, wherein the distal end extends interior of the artery and the proximal end extends exterior of the artery; and a plurality of self-expandable ring elements configured at the distal end of the elongate member, wherein each ring element, comprising a plurality of struts, is advanced through an intravascular microcatheter in a collapsed configuration, wherein the ring elements comprise a radial force biasing the ring elements toward an expanded configuration, wherein the radial force is absorbed by radial pins in the collapsed configuration, wherein the microcatheter is retracted allowing the ring elements to reach the expanded configuration.

In one variation of this embodiment the radial pin has an engagement member. In another variation of this embodiment each strut comprises a crown element. The crown element may comprise a plurality of eyelets. In another variation of this embodiment the distally facing eyelet engages with the radial pin. The distally facing eyelet may fasten the ring elements to the elongate member.

In another variation of this embodiment the proximally facing eyelet engages with the radial pins in a snap-fit mechanism. In another variation of this embodiment the snap-fit mechanism restrains the ring elements in the collapsed configuration. In another variation of this embodiment the engagement member is dissolved in vivo to disengage the snap-fit mechanism. In another variation of this embodiment the engagement member is dissolved in vivo allowing the ring elements to reach the expanded configuration.

An thirteenth embodiment of the invention comprises a mechanical clot retrieval device for use in vasculature, comprising an elongate member having a distal end, a proximal end, an outer tube having a plurality of slots and a retractable inner core wire, wherein the distal end extends interior of the artery and the proximal end extends exterior of the artery; a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements comprise a radial force biasing the ring elements toward an expanded configuration, wherein the radial force is absorbed by the inner core wire in the collapsed configuration, wherein the microcatheter is retracted proximally allowing the ring elements to reach the expanded configuration.

In one variation of this embodiment each strut comprises a crown element having an eyelet. In another variation of this embodiment a tether is advanced out of the slot to loop through the eyelet and folds back into the slot to loop around the retractable inner core wire. The tether may engage the ring elements with the elongate member in a tether-loop mechanism. In another variation of this embodiment the tether-loop mechanism restrains the ring elements in the collapsed configuration.

In another variation of this embodiment the retractable inner core wire is manually retracted proximally to disengage the tether-loop mechanism. The retractable inner core wire may be advanced out of each slot to loop through each eyelet and folds back into the slot to loop inside the outer tube. The retractable inner core wire may engage the ring elements with the elongate member in a tether-loop mechanism.

In another variation of this embodiment the tether-loop mechanism restrains the ring elements in the collapsed configuration. In another variation of this embodiment the retractable inner core wire is manually retracted proximally to disengage the tether-loop mechanism.

An fourteenth embodiment of the invention comprises a mechanical clot retrieval device for use in vasculature, comprising an elongate member having a distal end, a proximal end and a tube lumen having a plurality of slots, wherein the distal end extends interior of the artery and the proximal end extends exterior of the artery; and a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements comprise a radial force biasing the ring elements toward an expanded configuration, wherein the microcatheter is retracted proximally allowing the ring elements to reach the expanded configuration.

In one variation of this embodiment each strut comprises a crown element having an eyelet. In another variation of this embodiment the device further comprises a plurality of tethers, having distal ends that extend interior of the tube lumen and proximal ends that extend exterior of the artery. Each tether may be advanced through a slot to loop around the eyelet and folded back into the slot attached to the distal end of the elongate member. Each tether may engage the ring elements with the elongate member in a tether-loop mechanism. The tether-loop mechanism may restrain the ring elements in the collapsed configuration. Each tether may be broken to disengage the snap-fit mechanism allowing ring elements to reach the expanded configuration.

An fifteenth embodiment of the invention comprises a mechanical clot retrieval device for use in a blood artery, comprising an elongate member having a distal end and a proximal end, wherein the distal end extends interior of the artery and the proximal end extends exterior of the artery; a proximal collar attached to an abutment tube; and a plurality of self-expandable ring elements configured at the distal end of the elongate member, wherein each ring element, comprising a plurality of struts, is attached to the elongate member by connecting tethers and is advanced through an intravascular microcatheter in a collapsed configuration, wherein the ring elements comprise a radial force biasing the ring elements toward an expanded configuration, wherein the microcatheter is retracted allowing the ring elements to reach the expanded configuration.

In one variation of this embodiment each strut comprises a crown element. In another variation of this embodiment the device further comprises a plurality of tethers. Each tether may be looped around the ring element and is attached to the elongate member.

Each tether may engage the ring elements with the elongate member in a tether-loop mechanism. The radial force may be absorbed by the tether-loop mechanism. The tether-loop mechanism may restrain the ring elements in the collapsed configuration. In another variation of this embodiment the elongate member may be manually retracted proximally to disengage the tether-loop mechanism.

A sixteenth embodiment of the invention comprises a mechanical clot retrieval device for use in vasculature, comprising an elongate member having a distal end and a proximal end, wherein the distal end extends interior of the artery and the proximal end extends exterior of the artery; a plurality of collars configured at the distal end of the elongate member; and a plurality of self-expandable ring elements configured at the distal end of the elongate member, wherein each ring element is configured between two collars, wherein each ring element, comprising a plurality of struts, is interconnected by ring connecting tethers and is delivered through an intravascular microcatheter in a collapsed configuration, wherein the ring elements comprise a radial force biasing the ring elements toward an expanded configuration, wherein the radial force is absorbed by the collars in the collapsed configuration, wherein the microcatheter is retracted allowing the ring elements reach the expanded configuration.

In one variation of this embodiment the collar is bevel shaped or the collar is recess shaped or the collar is a shaped engagement collar or the collar has a plurality of holes or the collar has a plurality of dove tail grooves.

In one variation of this embodiment each strut comprises a crown element. In one variation of this embodiment the crown element has a tab extending axially and radially inward. The crown element may have a pin extending axially and radially inward. The crown element may have a shaped tab extending axially and radially inward and the tab may be bevel shaped. The tab may be square shaped. The tab may engage with the collar in a collar mechanism.

In another variation of this embodiment the collar mechanism engages the ring elements with the elongate member. The collar mechanism may restrain the ring elements in the collapsed configuration. In another variation of this embodiment the elongate member is manually retracted proximally to disengage the collar mechanism.

In another variation of this embodiment the pin engages with the hole in a collar mechanism. In another variation of this embodiment the collar mechanism engages the ring elements with the elongate member. In another variation of this embodiment the collar mechanism restrains the ring elements in the collapsed configuration. In another variation of this embodiment the elongate member is manually retracted proximally to disengage the collar mechanism.

In another variation of this embodiment the shaped tab engages with the dove tail groove in a collar mechanism. In another variation of this embodiment the collar mechanism engages the ring elements with the elongate member. In another variation of this embodiment the collar mechanism restrains the ring elements in the collapsed configuration. In another variation of this embodiment the elongate member is manually retracted proximally to disengage the collar mechanism.

A seventeenth embodiment of the invention comprises a mechanical clot retrieval device for use in vasculature, comprising an elongate member having a distal end and a proximal end, wherein the distal end extends interior of the artery and the proximal end extends exterior of the artery; a proximal collar; and a self-expandable ring element configured at the distal end of the elongate member, wherein the ring element, comprising a plurality of struts, is delivered through an intravascular microcatheter in a collapsed configuration, wherein the ring element comprises a radial force biasing the ring element towards an expanded configuration, wherein the radial force is absorbed by the proximal collar in the collapsed configuration, wherein the microcatheter is retracted allowing the ring element to reach the expanded configuration.

In one variation of this embodiment each strut comprises a crown element having a tab extending axially and radially inward. In another variation of this embodiment the tab engages with the proximal collar in a collar mechanism. In another variation of this embodiment the collar mechanism engages the ring element with the elongate member. In another variation of this embodiment the collar mechanism restrains the ring element in the collapsed configuration. In another variation of this embodiment the elongate member is manually retracted proximally to disengage the collar mechanism.

A eighteenth embodiment of the invention comprises a mechanical clot retrieval device for use in vasculature, comprising an elongate member having a distal end, a proximal end and inner lumen having a plurality of openings, wherein the distal end extends interior of the artery and the proximal end extends exterior of the artery; and a plurality of self-expandable ring elements configured at the distal end of the elongate member, wherein each ring element, comprising a plurality of struts, is interconnected by ring connecting tethers and is delivered through an intravascular catheter in a collapsed configuration, wherein the ring elements comprise a radial force biasing the ring elements toward an expanded configuration, wherein the microcatheter is retracted allowing the ring elements reach the expanded configuration.

In one variation of this embodiment each strut comprises a crown element and an engagement tab. In one variation of this embodiment the device further comprises a plurality of tethers having proximal ends extend exterior of the inner lumen. In one variation of this embodiment each tether is advanced out of each opening and is wrapped around the engagement tab in an eyelet mechanism. In one variation of this embodiment the eyelet mechanism engages the ring elements with the elongate member. In one variation of this embodiment the eyelet mechanism restrains the ring elements in the collapsed configuration.

In one variation of this embodiment the radial force is absorbed by the eyelet mechanism. In one variation of this embodiment the tethers are manually pulled proximally to disengage the eyelet mechanism.

A nineteenth embodiment of the invention comprises a mechanical clot retrieval device for use in a blood artery, comprising an elongate member having a distal end, a proximal end and a plurality of raised tabs, wherein the distal end extends interior of the artery and the proximal end extends exterior of the artery; and a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements comprise a radial force biasing the ring elements towards an expanded configuration, wherein the radial force is absorbed by the raised tabs in the collapsed configuration, wherein the microcatheter is retracted allowing the ring elements to reach the expanded configuration.

The variations described in association with each of the embodiments 1 through to 19 can be applied to the 20.sup.th through to the 36.sup.th embodiments (below) and are hereby incorporate as variations to each of the 20.sup.th through to the 36.sup.th embodiments.

A twentieth embodiment of the invention comprises a mechanical clot retrieval device for use in vasculature, comprising an elongate member having a distal end, a proximal end, a plurality of engagement diameters and a plurality of disengagement diameters, wherein the distal end extends interior of the artery and the proximal end extends exterior of the artery; a proximal abutment tube; and a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements comprise a radial force biasing the ring elements toward an expanded configuration, wherein the radial force is absorbed by engagement diameters in the collapsed configuration, wherein the microcatheter is retracted allowing the ring elements to reach the expanded configuration. Each strut may comprise a crown element having a C-shaped engagement tab extending radially inward. The C-shaped engagement tab engages with the engagement diameter to restrain the ring elements along the elongate member. The C-shaped engagement tab engages with the engagement diameter to restrain the ring element in the collapsed configuration. In one variation of this embodiment proximal axial movement of the elongate member disengages the ring element at the disengagement diameter.

A twenty first embodiment of the invention comprises a mechanical clot retrieval device for use in vasculature, comprising an elongate member having a distal end, a proximal end and an inner wire, wherein the distal end extends interior of the artery and the proximal end extends exterior of the artery; a proximal abutment tube; and a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements comprise a radial force biasing the ring elements toward an expanded configuration, wherein the radial force is absorbed by the elongate member in the collapsed configuration, wherein the microcatheter is retracted allowing the ring elements to reach the expanded configuration.

A twenty second embodiment of the invention comprises a mechanical clot retrieval device for use in vasculature, comprising: an elongate member having a distal end, a proximal end and an inner lumen with a plurality of slots, wherein the distal end extends interior of the artery and the proximal end extends exterior of the artery; a proximal collar; and a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements comprise a radial force biasing the ring elements toward an expanded configuration, wherein the radial force is absorbed by slots in the collapsed configuration, wherein the microcatheter is retracted allowing the ring elements to reach the expanded configuration.

A twenty third embodiment of the invention comprises a mechanical clot retrieval device for use in vasculature, comprising: an elongate member having a distal end, a proximal end and a plurality of monofilaments, wherein the distal end extends interior of the artery and the proximal end extends exterior of the artery; a proximal collar; and a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements comprise a radial force biasing the ring elements in an expanded configuration, wherein the radial force is absorbed by monofilaments in the collapsed configuration, wherein the microcatheter is retracted allowing the ring elements to reach the expanded configuration.

A twenty fourth embodiment of the invention comprises a mechanical clot retrieval device for use in vasculature, comprising: an elongate member having a distal end, a proximal end and a plurality of inactivated cuffs configured at the distal end of the elongate member, wherein the distal end extends interior of the artery and the proximal end extends exterior of the artery; a tube; and a plurality of self-expandable ring elements configured over the inactivated cuffs, wherein each ring element, comprising a plurality of struts, is interconnected by ring connecting tethers and is delivered through an intravascular microcatheter in a collapsed configuration, wherein the ring elements comprise a radial force biasing the ring elements towards an expanded configuration, wherein the microcatheter is retracted allowing the ring elements to reach the expanded configuration.

A twenty fifth embodiment of the invention comprises a mechanical clot retrieval device for use in vasculature, comprising an elongate member having a distal end and a proximal end, wherein the distal end extends interior of the artery and the proximal end extends exterior of the artery; a proximal collar; a bumper tube; and a plurality of self-expandable ring elements configured at the distal end of the elongate member, wherein each ring element, comprising a plurality of struts, is interconnected by ring connecting tethers and is delivered through an intravascular microcatheter in a collapsed configuration; wherein the ring elements comprise a radial force biasing the ring elements toward an expanded configuration, wherein the microcatheter is retracted allowing the ring elements to reach the expanded configuration.

A twenty sixth embodiment of the invention comprises a mechanical clot retrieval device for use vasculature, comprising: an elongate member having a distal end, a proximal end and a plurality of restraining loops configured at the distal end of the elongate member, wherein the distal end extends interior of the artery and the proximal end extends exterior of the artery; and a plurality of self-expandable ring elements configured at the distal end of the elongate member, wherein each ring element, comprising a plurality of struts, is connected to the restraining loop by connecting tethers, wherein the ring elements have a radial force biasing the ring elements toward an expanded configuration, wherein the radial force is absorbed by the restraining loops in a collapsed configuration.

A twenty seventh embodiment of the invention comprises a mechanical clot retrieval device for use in vasculature, comprising: an elongate member having a distal end and a proximal end, wherein the distal end extends interior of the artery and the proximal end that extends exterior of the artery; a bumper tube; a proximal collar; and a plurality of self-expandable ring elements configured at the distal end of the elongate member, wherein each ring element comprising a plurality of struts is interconnected by ring connecting tethers, wherein the ring elements comprise a radial force biasing the ring elements toward an expanded configuration, wherein the radial force is absorbed by the elongate member in a collapsed configuration.

A twenty eighth embodiment of the invention comprises a mechanical clot retrieval device for use in a tortuous vessel, comprising an elongate member having a distal end and a proximal end, wherein the distal end extends interior of the vessel and the proximal end extends exterior of the vessel; and a plurality of self-expandable ring elements configured at the distal end of the elongate member, wherein each ring element, comprising a plurality of struts, is interconnected by ring connecting tethers and is delivered through an intravascular microcatheter in a collapsed configuration, wherein the ring elements have a radial force biasing the ring elements toward an expanded configuration, wherein the radial force is absorbed by the microcatheter in the collapsed configuration, wherein the microcatheter is retracted allowing the ring elements to reach the expanded configuration.

A twenty ninth embodiment of the invention comprises a mechanical clot retrieval device for use in a tortuous vessel, comprising an elongate member having a distal end and a proximal end, wherein the distal end extends interior of the vessel and the proximal end extends exterior of the vessel; a plurality of self-expandable ring elements having a first diameter and a second diameter, wherein each ring element, comprising a plurality of struts, is interconnected by ring connecting tethers and is delivered through an intravascular microcatheter in a collapsed configuration; and a control strut having distal end attached to most proximal ring element and proximal end attached to the elongate member by adhesive bonds, wherein the ring elements have a radial force biasing the ring elements toward an expanded configuration, wherein the radial force is absorbed by the microcatheter in the collapsed configuration, wherein the microcatheter is retracted proximally allowing the ring elements to reach the expanded configuration.

A thirtieth embodiment of the invention comprises a mechanical clot retrieval device for use in a tortuous vessel, comprising an elongate member having a distal end and a proximal end, wherein the distal end extends interior of the vessel and the proximal end extends exterior of the vessel; and a plurality of self-expandable ring elements, wherein each ring element, comprising a plurality of struts, is interconnected by ring connecting tethers and is delivered through an intravascular microcatheter in a collapsed configuration; and wherein the ring elements have a radial force biasing the ring elements towards an expanded configuration, wherein the radial force is absorbed by the microcatheter in the collapsed configuration, wherein the microcatheter is retracted proximally allowing the ring elements reach the expanded configuration.

A thirty first embodiment of the invention comprises a mechanical clot retrieval device for use in a tortuous vessel, comprising: an elongate member having a distal end and a proximal end, wherein the distal end extends interior of the vessel and the proximal end extends exterior of the vessel; a plurality of self-expandable ring elements configured at the distal end of the elongate member, wherein each ring element comprises a plurality of struts and is delivered through an intravascular microcatheter in a collapsed configuration; and a plurality of ring connecting tethers having distal and proximal ends, wherein the distal ends are connected to the ring element and the proximal ends are attached to the elongate member, wherein the ring elements have a radial force biasing the ring elements towards an expanded configuration, wherein the radial force is absorbed by the microcatheter in the collapsed configuration, wherein the microcatheter is retracted allowing the ring elements to reach the expanded configuration.

A thirty second embodiment of the invention comprises a mechanical clot retrieval device for use in vasculature, comprising an activation tether having a distal end and a proximal end, wherein the distal end extends interior of the artery and the proximal end extends exterior of the artery; a distal collar, wherein the distal end of the activation tether is attached to the distal collar; and a plurality of self-expandable ring elements configured at the distal end of the activation tether, wherein each ring element, comprising a plurality of struts, is interconnected by bridges and is delivered through a microcatheter in a collapsed configuration, wherein the ring elements have a radial force biasing the ring elements towards an expanded configuration, wherein the radial force is absorbed by the microcatheter in the collapsed configuration, wherein the microcatheter is retracted allowing the ring elements reach the expanded configuration.

A thirty third embodiment of the invention comprises a mechanical clot retrieval device for use in vasculature, comprising an activation tether having a distal end and a proximal end, wherein the distal end extends interior of the artery and the proximal end extends exterior of the artery; a distal collar, wherein the distal end of the activation tether is attached to the distal collar; and a self-expandable ring element configured at the distal end of the activation tether, wherein the ring element comprises a plurality of struts and is delivered through a microcatheter in a collapsed configuration, wherein the ring element has a radial force biasing the ring element toward the expanded configuration, wherein the radial force is absorbed by the microcatheter in the collapsed configuration, wherein the microcatheter is retracted allowing the ring element to reach the expanded configuration.

A thirty fourth embodiment of the invention comprises a mechanical clot retrieval device for use in vasculature, comprising an activation tether having a distal end and a proximal end, wherein the distal end extends interior of the artery and the proximal end extends exterior of the artery; a distal collar, wherein the distal end of the activation tether is attached the distal collar; a self-expandable ring element configured at the distal end of the activation tether, wherein the ring element comprises a plurality of struts and is delivered through a microcatheter in a collapsed configuration; and a pair of removal tethers having distal ends attached to the ring element and proximal ends that extend exterior of the artery, wherein the ring element has a radial force biasing the ring element towards an expanded configuration, wherein the radial force is absorbed by the microcatheter in the collapsed configuration, wherein the microcatheter is retracted allowing the ring element to reach the expanded configuration.

A thirty fifth embodiment of the invention comprises a mechanical clot retrieval device for use in vasculature, comprising an activation tether having a distal end and a proximal end, wherein the distal end extends interior of the artery and the proximal end extends exterior of the artery; a couple of collars; a couple of ring elements configured at the distal end of the activation tether, wherein each ring element comprising a plurality of struts and is delivered through a microcatheter in a collapsed configuration; and a pair of removal tethers having distal ends attached to the ring element and proximal ends attached to the collar, wherein the ring elements have a radial force biasing the ring elements toward an expanded configuration, wherein the radial force is absorbed by the microcatheter in the collapsed configuration, wherein the microcatheter is retracted allowing the ring elements to reach the expanded configuration.

A thirty sixth embodiment of the invention comprises a mechanical clot retrieval device for use in vasculature, comprising a pair of activation tethers having distal ends extending interior of the artery and proximal ends extending exterior of the artery; a distal collar, wherein distal ends of the activation tether are attached to the distal collar; and a plurality of self-expandable ring elements configured at distal ends of the activation tethers, wherein the each ring element, comprising a plurality of struts, is interconnected by bridges and is delivered through an intravascular microcatheter in a collapsed configuration, wherein the ring elements have a radial force biasing the ring elements towards an expanded configuration, wherein the radial force is absorbed by the microcatheter in the collapsed configuration, wherein the microcatheter is retracted allowing the ring elements to reach the expanded configuration.

The mechanical clot retrieval device in any of the preceding embodiments may comprise a ring element made of shape memory material. The mechanical clot retrieval device in any of the preceding embodiments may comprise a ring element is made of Nitinol. The mechanical clot retrieval device in any of the preceding embodiments may comprise a retrieval device that is made of shape memory material. The mechanical clot retrieval device in any of the preceding embodiments may comprise a retrieval device that is partly made of shape memory material.

BRIEF DESCRIPTION OF THE DRAWINGS

The invention will be more clearly understood from the following description of some embodiments thereof, given by way of example with reference to the accompanying drawings, in which:

FIG. 1a is a diagram illustrating a typical occlusive clot in a cerebral artery;

FIG. 1b is an enlarged view of a detail of FIG. 1a;

FIGS. 2a-2h are diagrams illustrating the insertion of a guidewire and the deployment of a clot retrieval device of the invention;

FIGS. 3a-3e illustrate a clot retrieval device according to one embodiment of the invention;

FIGS. 4a-4d illustrate steps involved in using the device of FIGS. 3a-3d;

FIGS. 5a-5e illustrate another clot retrieval device of the invention;

FIGS. 6a-6f illustrate a further clot retrieval device of the invention;

FIGS. 7a-7e illustrate another clot retrieval device of the invention;

FIGS. 8a-8d illustrate a further clot retrieval device of the invention;

FIGS. 9a-9d illustrate another clot retrieval device of the invention;

FIGS. 11a-11h illustrate another clot retrieval device of the invention;

FIGS. 12a-12c illustrate a further clot retrieval device of the invention;

FIGS. 13a-13f illustrate another clot retrieval device of the invention;

FIGS. 14a-14c illustrate a further clot retrieval device of the invention;

FIGS. 15a-15c illustrate a method for using a clot retrieval device of the invention;

FIGS. 16a-16d illustrate another method for using a clot retrieval device of the invention;

FIGS. 17a-17d illustrate a further clot retrieval device of the invention;

FIGS. 18a-18d illustrate another clot retrieval device of the invention;

FIGS. 19a-19d illustrate a further clot retrieval device of the invention;

FIGS. 20a-20b illustrate another clot retrieval device of the invention;

FIGS. 21a-21f illustrate a further clot retrieval device of the invention;

FIGS. 23a-23c illustrate a mechanism used in a clot retrieval device of the invention;

FIGS. 25a-25k illustrate another clot retrieval device of the invention;

FIGS. 26a-26d illustrate a further clot retrieval device of the invention;

FIGS. 27a-27b illustrate another clot retrieval device of the invention;

FIGS. 28a-28b illustrate a further clot retrieval device of the invention;

FIGS. 29a-29h illustrate a method for using a clot retrieval device of the invention;

FIGS. 30a-30e illustrate another clot retrieval device of the invention;

FIGS. 31a-31e illustrate a further clot retrieval device of the invention;

FIGS. 32a-32d illustrate another clot retrieval device of the invention;

FIGS. 33a-33g illustrate a further clot retrieval device of the invention;

FIGS. 34a-34j illustrate another clot retrieval device of the invention;

FIGS. 36a-36d illustrate another clot retrieval device of the invention;

FIGS. 37a-37i illustrate a further clot retrieval device of the invention;

FIGS. 39a-39d illustrate a further clot retrieval device of the invention;

FIGS. 40a-40e illustrate a method for using a clot retrieval device of the invention;

FIGS. 41a-41d illustrate another method for using a clot retrieval device of the invention;

FIGS. 42a-42g illustrate a further clot retrieval device of the invention;

FIGS. 43a-43h illustrate another clot retrieval device of the invention;

FIGS. 44a-44b illustrate a further clot retrieval device of the invention;

FIGS. 48a-48f illustrate a further clot retrieval device of the invention;

FIGS. 49a-49f illustrate another clot retrieval device of the invention;

FIGS. 50a-50g illustrate a further clot retrieval device of the invention;

FIGS. 51a-51f illustrate another clot retrieval device of the invention;

FIGS. 52a-52d illustrate a further clot retrieval device of the invention;

FIGS. 53a-53f illustrate a method for using a clot retrieval device of the invention;

FIGS. 54a-54h illustrate another method for using a clot retrieval device of the invention;

FIG. 55 illustrates another clot retrieval device of the invention;

FIG. 56 illustrates a further clot retrieval device of the invention;

FIG. 57 illustrates another clot retrieval device of the invention;

FIG. 58 illustrates a further clot retrieval device of the invention;

FIG. 59 illustrates a further clot retrieval device of the invention;

FIG. 60 illustrates another clot retrieval device of the invention;

FIGS. 61a-61c illustrate a further clot retrieval device of the invention;

FIGS. 62a-62b illustrate another clot retrieval device of the invention;

FIGS. 63a-63b illustrate a further clot retrieval device of the invention;

FIGS. 64a-64b illustrate another clot retrieval device of the invention;

FIGS. 65a-65d illustrate a further clot retrieval device of the invention;

FIGS. 66a-66c illustrate another clot retrieval device of the invention;

FIGS. 67a-67b illustrate a further clot retrieval device of the invention;

FIGS. 68a-68b illustrate another clot retrieval device of the invention;

FIGS. 69a-69b illustrate a further clot retrieval device of the invention; and

DETAILED DESCRIPTION OF PREFERRED EMBODIMENTS

Figure 10A:
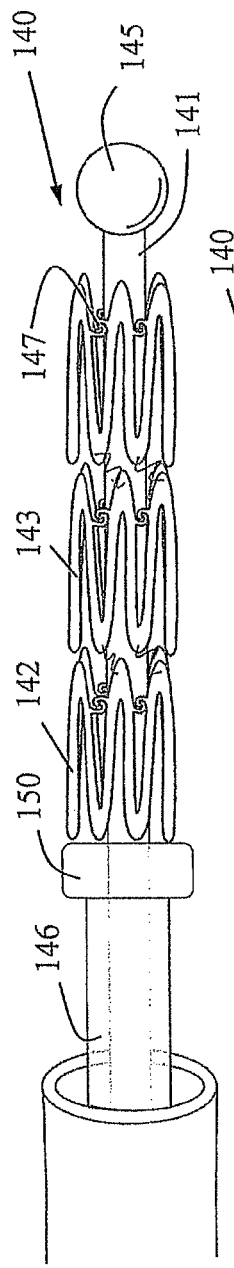
FIGS. 10a-10d illustrate a further clot retrieval device of the invention.
Figure 10B:
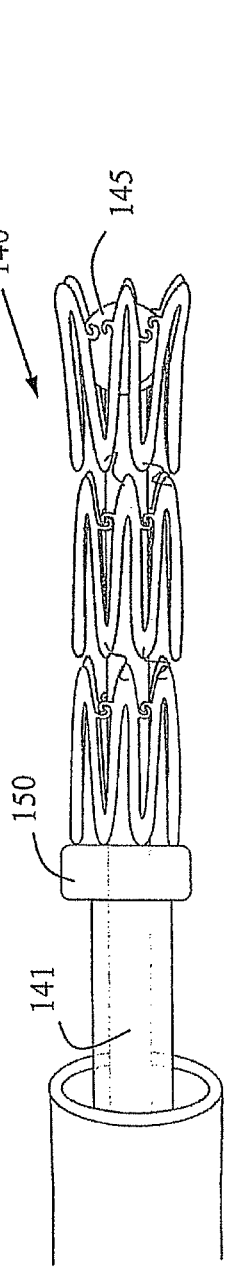
Figure 10C:
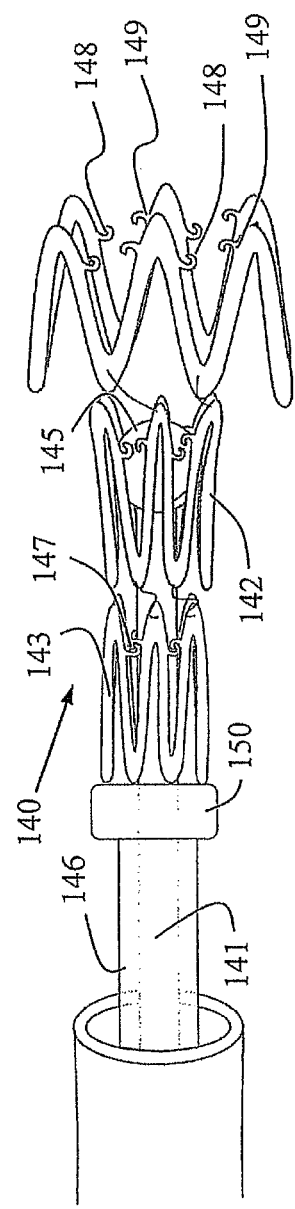
Figure 10D:
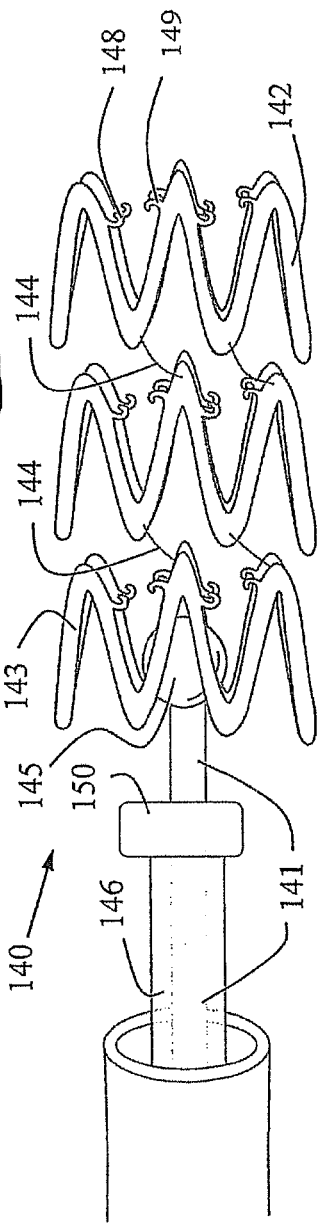
Figures 22A, 22B, 22C, 22D:
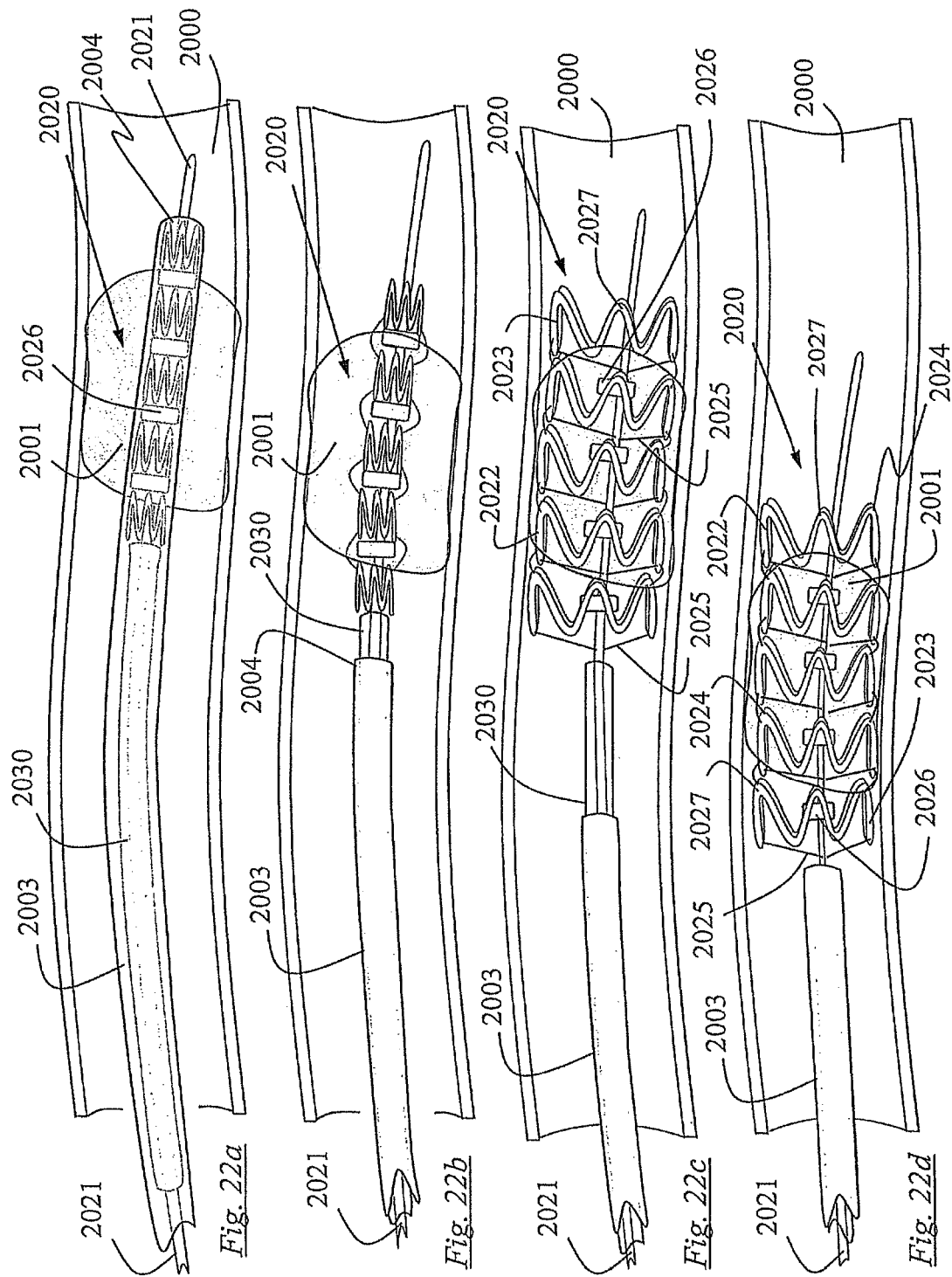
FIGS. 22a-22d illustrate a method for using a clot retrieval device of the invention.

Specific embodiments of the present invention are now described in detail with reference to the figures, wherein similar reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

The following detailed description is merely exemplary in nature and is not intended to limit the invention or the application and uses of the invention. Although the description of the invention is in the context of treatment of blood arteries such as the carotid and lung arteries, the invention may also be used in any other vessels where it is deemed useful.

As shown generally in FIGS. 1a-1b and 2a-2h, an obstructive clot 2 is occluding a cerebral artery 1 and a guidewire 3 is inserted into the artery 1 using conventionally known techniques. The guidewire 3 is advanced across the clot 2 and then a microcatheter 4 is advanced over the guidewire 3 to a location distal to the clot 2. The mechanical clot retrieval device 10 of the present invention is advanced through the microcatheter 4 and across the clot 2. The retrieval device 10 has an elongate member 11 having a distal end that extends interior of the artery and a proximal end that extends exterior of the artery, and a plurality of ring elements 12 configured at the distal end of the elongate member. The ring elements 12 are self-expandable from a collapsed configuration to an expanded configuration and comprise a radial force that biases the ring elements 12 toward the expanded configuration. In the collapsed configuration, the radial force is absorbed by the elongate member 11. When the retrieval device 10 is advanced through the microcatheter 4, the ring elements are in the collapsed configuration substantially parallel to the longitudinal axis of the elongate member 11. Each ring element 12 comprising a plurality of struts 13 is made of self expanding material such as nitinol and is interconnected by ring connecting tethers 14. The microcatheter 4 is retracted after the retrieval device 10 is positioned within or distal of the clot 2 to allow ring elements 12 to deploy and expand. When the ring elements 12 deploy and expand, the struts 13 engage or capture the clot 2 in the ring elements 12 and the retrieval device 10 is retracted proximally out of the artery 1.

FIGS. 3a-3d illustrates one of the preferred embodiments of a mechanical clot retrieval device 20 of the present invention. The retrieval device 20 has an elongate member 21 having a distal end that extends interior of the artery and a proximal end that extends exterior of the artery, and a plurality of ring elements 22 configured at the distal end of the elongate member 21. The ring elements 22 are self-expandable from a collapsed configuration to an expanded configuration and comprise a radial force that biases the ring elements 22 toward the expanded configuration. In the collapsed configuration, the radial force is absorbed by the elongate member 21. Each ring element 22 comprising a plurality of struts 23 is made of shape memory material Nitinol and is interconnected by ring connecting tethers 24. Each strut 23 has a crown element 27 with an engagement member 29 and a fixed tab 30. The crown element 27 holds the neighboring crown element 27 in a snap-fit mechanism 28 to restrain the ring elements 22 in the collapsed configuration substantially parallel to the longitudinal axis of the elongate member 21. Two pull tethers 25 which have distal ends that are attached to most proximal ring element 22, and proximal ends that extend exterior of the artery for maneuvering and control by the physician, are present. The snap-fit mechanism 28 restrains the retrieval device 20 in the collapsed configuration when advancing through a microcatheter 4.

FIGS. 4a-4d shows a method of using the retrieval device 20 in accordance with the preferred embodiment as shown in FIGS. 3a-3d. A guidewire (not shown) is inserted in the cerebral artery 1 and is advanced distally across an obstructive clot 2. A microcatheter 4 is advanced over the guidewire to a location proximal to the clot and then the retrieval device 20 of the present invention is advanced through the microcatheter 4 to the clot in the collapsed configuration. The retrieval device 20 has an elongate member 21 having a distal end that extends interior of the artery and a proximal end that extends exterior of the artery, and a plurality of ring elements 22 configured at the distal end of an elongate member 21. The ring elements 22 are self-expandable from a collapsed configuration to an expanded configuration and comprise a radial force that biases the ring elements 22 toward the expanded configuration. In the collapsed configuration, the radial force is absorbed by the elongate member 21. When the retrieval device 20 is advanced through the microcatheter 4, the ring elements are in collapsed configuration substantially parallel to the longitudinal axis of the elongate member 21. Each ring element 22 comprises a plurality of struts 23 and is made of shape memory material nitinol and is interconnected by ring connecting tethers 24. The microcatheter 4 is retracted when the retrieval device 20 is positioned within or distal of the clot 2 to allow ring elements 22 to reach the expanded configuration. The pull tethers 25 attached to the retrieval device 20 allow the physician to manually disengage the snap-fit mechanism 28. The ring elements 22 engage or capture the clot 2 from the distal surface of the clot 2 and retract the clot 2 proximally towards the microcatheter 4. The microcatheter 4 is re-advanced to reduce the expanded configuration of the proximal end of the device 20 in order to retrieve it more easily from the artery 1.

FIGS. 5a-5d shows a mechanical clot retrieval device 40 of the present invention which is a slight variant of the embodiment of the retrieval device as shown in FIGS. 3a-3d. The retrieval device 40 has an elongate member 41 having a distal end that extends interior of the artery and a proximal end that extends exterior of the artery, a plurality of ring elements 42 configured at the distal end of the elongate member 41, and a proximal collar 51. The ring elements 42 are self-expandable from a collapsed configuration to an expanded configuration and comprise a radial force that biases the ring elements 42 toward the expanded configuration. In the collapsed configuration, the radial force is absorbed by the elongate member 41. Each ring element 42 comprising a plurality of struts 43 and is made of shape memory material Nitinol and is interconnected by ring connecting tethers 44. Also present are a pair of pull tethers 45, having distal ends which are attached to the most proximal ring element 42 and the proximal ends are attached to the elongate member 41. Each strut 43 has a crown element 47 with an engagement member 49 and an engagement hook 50. Each crown element 47 holds the neighboring crown element 47 in a snap-fit mechanism 48 which restrains the ring elements 42 in the collapsed configuration substantially parallel to the longitudinal axis of the elongate member 41. The snap-fit configuration 48 restrains the retrieval device 40 in the collapsed configuration when advancing through the microcatheter 4.

Another embodiment of the mechanical clot retrieval device of the present invention, which is similar to the one shown in FIGS. 3a-3d, is illustrated in FIGS. 6a-6f. The retrieval device 60 has an elongate member 61 having a distal end that extends interior of the artery and a proximal end that extends exterior of the artery, and a plurality of ring elements 62 configured at the distal end of the elongate member 61. The ring elements 62 are self-expandable from a collapsed configuration to an expanded configuration and comprise a radial force that biases the ring elements 62 toward the expanded configuration. In the collapsed configuration, the radial force is absorbed by the elongate member 61. Each ring element 62, comprising a plurality of struts 63, is made of shape memory material Nitinol and is interconnected by ring connecting tethers 64. Each strut 63 has a crown element 67 with an engagement member 68. Each engagement member 68 holds the neighboring crown element 67 in a snap-fit mechanism which restrains the ring elements 62 in the collapsed configuration substantially parallel to the longitudinal axis of the elongate member 61. A pair of pull tethers 65 are attached, having distal ends which are attached to each connector (not labeled) of the crown element 67, and proximal ends which extend exterior of the artery for manipulation and control by the physician. The snap-fit mechanism restrains the retrieval device 60 in the collapsed configuration as it is advancing through the microcatheter 4. The pull tethers 65 may be used to manually disengage the snap-fit mechanism and allow the retrieval device 60 reach the expanded configuration.

Another embodiment of the mechanical clot retrieval device of the present invention, which is largely similar to the one shown in FIGS. 3a-3d, is illustrated in FIGS. 7a-7f. The retrieval device 80 has an elongate member 81 having a distal end that extends interior of the artery and a proximal end that extends exterior of the artery, and a plurality of ring elements 82 configured at the distal end of the elongate member 81. The ring elements 82 are self-expandable from a collapsed configuration to an expanded configuration and comprise a radial force that biases the ring elements 82 toward the expanded configuration. In the collapsed configuration, the radial force is absorbed by the elongate member 81. Each ring element 82, comprising a plurality of struts 83, is made of shape memory material Nitinol and is interconnected by ring connecting tethers 84. Each strut 83 has a crown element 87 with an engagement member 89 and an engagement tab 88. Each crown element 87 holds the neighboring crown element 87 in a snap-fit mechanism which restrains the ring elements 82 in the collapsed configuration substantially parallel to the longitudinal axis of the elongate member 81. A pair of pull tethers 85 is attached, having distal ends which are attached to each engagement tab 88 of the crown element 87, and proximal ends which extend exterior of the artery for manipulation and control by the physician. The snap-fit mechanism restrains the retrieval device 80 in the collapsed configuration as it is advancing through the microcatheter 4. The pull tethers 85 may be used to manually disengage the snap-fit mechanism and allow the retrieval device 80 to reach the expanded configuration.

Another preferred embodiment of the mechanical clot retrieval device 100 of the present invention is illustrated in FIGS. 8a-8d. The retrieval device 100 includes an elongate member 101 having a distal end that extends interior of the artery and a proximal end that extends exterior of the artery, a plurality of ring elements 102 arranged at the distal end of the elongate member 101, a fixed proximal collar 111 and a distal moveable collar 110. The ring elements 102 are self-expandable from a collapsed configuration to an expanded configuration and comprise a radial force that biases the ring elements 102 toward the expanded configuration. In the collapsed configuration, the radial force is absorbed by the elongate member 101. Each ring element 102 comprising a plurality of struts 103 is made of shape memory material nitinol and is interconnected by ring connecting tethers 104. Each strut 103 has a hook lock 107 with first lock 108 and second lock 109. Each hook lock 107 holds the neighboring hook lock 107 in a snap-fit mechanism to restrain the ring elements 102 in the collapsed configuration substantially parallel to the axis of the elongate member 101. There are pair of pull tethers 105 attached, having distal ends which are attached to the distal collar 110, and proximal ends that extend exterior of the artery for maneuvering and control by the physician. The snap-fit mechanism restrains the retrieval device in the collapsed configuration when advancing through the microcatheter 4. The distal collar 110 is pulled proximally by the pull tether 105 to manually disengage and allow ring elements 102 reach an expanded configuration.

FIGS. 9a-9d shows a mechanical clot retrieval device 120 of the present invention, which is a slight variant of the embodiment of the retrieval device 100 as shown in FIGS. 8a-8d; the only difference is use of a balloon 125 in place of the distal moveable collar 110. The retrieval device 120 has an elongate member having a distal end that extends interior of the artery and a proximal end that extends exterior of the artery, a plurality of ring elements 122 configured at the distal end of the elongate member 121, a proximal collar 126 and a balloon 125. The ring elements 122 are self-expandable from a collapsed configuration to an expanded configuration and have a radial force that biases the ring elements 122 toward the expanded configuration. In the collapsed configuration, the radial force is absorbed by the elongate member 121. Each ring element 122 comprises a plurality of struts 123 and is made of shape memory material nitinol and is interconnected by ring connecting tethers 124. Each strut 123 has a hook lock 127 with a first lock 128 and a second lock 109. Each hook lock 127 holds the neighboring hook lock 127 in a snap-fit mechanism to restrain the ring elements 122 in the collapsed configuration. The balloon 125 is in a collapsed state when the device 20 is advanced through the microcatheter 4. The balloon 125 is inflated to disengage and allow ring elements 122 to reach the expanded configuration.

Another embodiment of a mechanical clot retrieval device 140 of the present invention is largely similar to the one shown in FIGS. 8a-8d, and is shown in FIGS. 10a-10d; with the main difference being the use of a ball element 145 in place of the distal movable collar 110. The retrieval device 140 has an elongate member 141 having a distal end that extends interior of the artery and a proximal end that extends exterior of the artery, a plurality of ring elements 142 configured at the distal end of the elongate member 141, a proximal collar 150 attached to a push tube 146, and a ball element 145. The ring elements 142 are self-expandable from a collapsed configuration to an expanded configuration and feature a radial force that biases the ring elements 142 toward the expanded configuration. In the collapsed configuration, the radial force is absorbed by the elongate member 141. Each ring element 142, comprising a plurality of struts 143, is made of shape memory material nitinol and is interconnected by ring connecting tethers 144. Each strut 143 has a hook lock 147 with a first lock 148 and a second lock 149. Each hook lock 147 holds the neighboring hook lock 147 in a snap-fit mechanism to restrain the device 140 in the collapsed configuration. The ball element 145 is manually pulled proximally through the device 140 to force apart the ring elements 142 which subsequently form the expanded configuration.

FIGS. 11a-11h shows another preferred embodiment of a mechanical clot retrieval device of the present invention. The retrieval device 160 includes an elongate member 161 having a distal end that extends interior of the artery and a proximal end that extends exterior of the artery, and a plurality of ring elements 162 attached to the elongate member 161 by connecting tethers 164 at connection points 165. The ring elements 162 are self-expandable from a collapsed configuration to an expanded configuration and comprise a radial force that biases the ring elements 162 toward the expanded configuration. In the collapsed configuration, the radial force is absorbed by the elongate member 161. Each ring element 162, comprising a plurality of struts 163, is made of shape memory material nitinol. Each strut 163 features a crown element 169, which includes a proximal ring crown 167 and a distal ring crown 166. The connecting tether 164 connects the proximal ring crown 167 with the elongate member 161. The crown element 169 engages with the elongate member 161 in a snap-fit mechanism to restrain the ring elements 162 in the collapsed configuration. The snap-fit mechanism 168 restrains the retrieval device 160 in the collapsed configuration as it advances through a microcatheter 4. The microcatheter 4 is retracted proximally to disengage and allow the ring elements 162 to reach the expanded configuration. The elongate member 161 is manually retracted to disengage the snap-fit mechanism.

Another embodiment of a mechanical clot retrieval device of the present invention is illustrated in FIGS. 12a-12c. A guidewire is inserted inside a cerebral artery 501 using conventional techniques. The guidewire is advanced across an obstructive clot 502 and then an intravascular microcatheter 504 is advanced over the guidewire to a location proximal to the clot 502. The retrieval device 520 has an elongate member having a distal end that extends interior of the artery and a proximal end that extends exterior of the artery, and a plurality of ring elements 522 configured at the distal end 526 of the elongate member 521. The ring elements 522 are self-expandable from a collapsed configuration to an expanded configuration and have a radial force that biases the ring elements 522 towards the expanded configuration. Each ring element 522, comprising a plurality of struts 523, is made of shape memory material nitinol and is interconnected by ring connecting tethers 524. Each strut 523 has a crown element 527 attached to the elongate member 521 by a bonding agent 528 to restrain the ring elements 522 in the collapsed configuration. The radial force is absorbed by the bonding agent 528 to restrain the retrieval device 520 in the collapsed configuration when the device is advancing through the microcatheter 504. The bonding agent 528 is dissolved in vivo to disengage and allow the ring elements 522 to reach the expanded configuration. The device has a pair of pull tethers 525, having distal ends which are attached to most proximal ring element 522 and proximal ends that extend out of the artery for maneuvering and control by the physician.

FIGS. 13a-13f shows a slight variant embodiment of a mechanical clot retrieval device of the present invention, largely similar to the one shown in FIGS. 12a-12c. The difference between the two is the use of a soluble covering 548 in place of the bonding agent 528. The retrieval device 540 has an elongate member, having a distal end that extends interior of the artery and a proximal end that extends exterior of the artery, and a plurality of ring elements 542 configured at the distal end 546 of the elongate member 541. The ring elements 542 are self-expandable from a collapsed configuration to an expanded configuration and comprise a radial force biasing the ring elements 542 towards the expanded configuration. Each ring element 542, comprising a plurality of struts 543, is made of shape memory material nitinol and is interconnected by ring connecting tethers 544. Each strut 543 has a crown element 547 attached to the elongate member 541 by a re-absorbable covering 548 to restrain the ring elements 542 in the collapsed configuration. The radial force is absorbed by the re-absorbable covering 548 to restrain the retrieval device 540 in the collapsed configuration when it is advancing through the microcatheter (not shown). The re-absorbable covering 548 is dissolved in vivo to disengage and allow the ring elements 542 to reach the expanded configuration. The device features a pair of pull tethers 545, having distal ends which are attached to the most proximal ring element 542 and proximal ends that extend out of the artery for maneuvering and control by the physician.

Another preferred embodiment of a mechanical clot retrieval device of the present invention is shown in FIGS. 14a-14c. The retrieval device 1020 includes an elongate member 1021 having a distal end that extends interior of the artery, a proximal end that extends exterior of the artery and a plurality of radial pins 1028, and a plurality of ring elements 1022 configured at the distal end 1026 of the elongate member 1021. The ring elements 1022 are self-expandable from a collapsed configuration to an expanded configuration and comprise a radial force that biases ring elements 1022 towards the expanded configuration. Each ring element 1022, comprising a plurality of struts, is made of shape memory material nitinol and each strut 1023 contains a crown element 1027 with an eyelet 1024. The distal eyelet 1024 engages with the radial pin 1028 by an engagement element 1029 to fasten the ring elements to the elongate member, whereas proximal eyelets 1024 engage with engagement members 1029 of radial pins 1028 in a snap-fit mechanism to restrain the ring elements 1022 in the collapsed configuration. The ring elements 1022 may be connected to the elongate member 1021 by ring connecting tethers (not shown). The snap-fit mechanism restrains the retrieval device 1020 in the collapsed configuration when advancing through the microcatheter (not shown).

FIGS. 15a-15c and 16a-16d show a method for using a mechanical clot retrieval device 1040 in accordance with the preferred embodiment shown in FIGS. 14a-14c. A guidewire 1003 is inserted in a cerebral artery 1001 and is advanced across an obstructive clot 1002. An intravascular microcatheter 1004 is advanced over the guidewire 1003 to a location proximal to the clot 1002 and then a mechanical clot retrieval device 1004 is advanced through the microcatheter 1004 to the clot 1002 in a collapsed configuration. The retrieval device 1004 includes an elongate member 1041 having a distal end that extends interior of the artery, a proximal end that extends exterior of the artery and a plurality of radical pins 1048, and a plurality of ring elements 1042 arranged at the distal end 1046 of the elongate member 1041. The ring elements 1042 are self-expandable from a collapsed configuration to an expanded configuration and comprise a radial force that biases the ring elements 1042 toward the expanded configuration. Each ring element 1042, comprising a plurality of struts 1043, is made of shape memory material nitinol and each strut features a crown element 1047 with an eyelet 1044. The eyelets 1044 engage with the radial pins 1048 to attach the ring elements to the elongate member. The radial force is absorbed by radial pins to restrain the ring elements 1042 in the collapsed configuration. When microcatheter 1004 is retracted the ring elements 1042 are able to expand and disengage eyelets 1044 from pins 1048 and are thus freed to expand towards the fully expanded configuration. The ring elements 1042 engage or capture the clot and the device can then be retracted proximally and removed from the artery. In one embodiment the ring elements are connected to the elongate member 1041 by tether elements 1045 as shown in FIGS. 16c and 16d.

Another preferred embodiment of a mechanical clot retrieval device of the present invention is illustrated in FIGS. 17a-17d. The retrieval device 1520 includes an elongate member 1521 having a distal end that extends interior of the artery, a proximal end that extends exterior of the artery, an outer tube 1530 with a plurality of slots 1532 and a retractable inner core wire 1531 which has a proximal end that extends exterior of the artery, and a plurality of ring elements 1522 configured at the distal end of the elongate member 1521. The ring elements 1522 are self-expandable from a collapsed configuration to an expanded configuration and comprise a radial force that biases the ring elements 1522 toward the expanded configuration. Each ring element 1522 comprising a plurality of struts 1523 is made of shape memory material nitinol and is interconnected by ring connecting tethers 1525. Each strut 1523 has a crown element 1527 with an eyelet 1524. A tether is advanced out of the slot 1532 to loop 1528 through the eyelet 1524 and advanced back in the slot 1532 to loop 1526 around the core wire 1531 to engage each ring element 1522 to the elongate member 1521 in a tether-loop mechanism. The radial force is absorbed by the tether-loop mechanism to restrain the retrieval device 1520 in the collapsed configuration when advancing through a microcatheter (not shown). The core wire 1531 is retracted proximally thus disengaging and allowing each ring element 1522 reach the expanded configuration.

FIGS. 18a-18c depict a mechanical clot retrieval device 1540 of the present invention which is a variant of the retrieval device 1520 as illustrated in FIGS. 17a-17d. FIG. 18d is a view of a cross-section through line 1553 of FIG. 18b. The retrieval device 1540 includes an elongate member 1541 having a distal end that extends interior of the artery, a proximal end that extends exterior of the artery, an outer tube 1550 with a plurality of slots 1552 and a retractable inner core wire 1551 having proximal end 1549 that extends exterior of the artery, and a plurality of ring elements 1542 arranged at the distal end of the elongate member 1541. The ring elements 1542 are self-expandable from a collapsed configuration to an expanded configuration and have a radial force that biases the ring elements 1542 toward the expanded configuration. Each ring element 1542, comprising a plurality of struts 1543, is made of shape memory material nitinol and is interconnected by ring connecting tethers (not shown). Each strut 1543 has a crown element 1547 with an eyelet 1544. The core wire 1551 is advanced out of each slot 1552 to loop 1546 through each eyelet 1544 and advanced back in the slot 1552 to loop inside the outer tube 1550 to engage each ring element 1542 to the elongate member 1541 in a tether-loop mechanism. The radial force is absorbed by the tether-loop mechanism to restrain the retrieval device 1540 in the collapsed configuration when advancing through a microcatheter (not shown). The core wire 1551 is retracted in order to disengage and allow each ring element 1542 reach the expanded configuration.

FIGS. 19a-19d represents a mechanical clot retrieval device of the present invention which is yet another slightly variant embodiment of the retrieval device 1520 as illustrated in FIGS. 17a-17d. The retrieval device 1560 includes an elongate member 1561 having a distal end 1569 that extends interior of the artery, a proximal end that extends exterior of the artery and a tube lumen 1570 with a plurality of slots 1571, and a plurality of ring elements 1562 configured at the distal end of the elongate member 1561. The ring elements 1562 are self-expandable from a collapsed configuration to an expanded configuration and comprise a radial force that biases the ring elements 1562 toward the expanded configuration. Each ring element 1562, comprising a plurality of struts 1563, is made of shape memory material nitinol and is interconnected by ring connecting tethers 1565. Each strut 1563 has a crown element 1568 with an eyelet 1564. A plurality of tethers 1566 is positioned within the lumen 1570 and is advanced out of each slot 1571 to loop 1567 each eyelet 1564 and is attached at a distal end 1569 of the elongate member 1561 to engage each ring element 1562 to the elongate member 1561 in a tether-loop mechanism. The radial force is absorbed by the tether-loop mechanism to restrain the retrieval device 1560 in the collapsed configuration when advancing through a microcatheter (not shown). The tethers 1566 are broken or cut to disengage and allow each ring element 1562 reach an expanded configuration.

FIGS. 20a-20b shows a mechanical clot retrieval device 1580 of the present invention. The retrieval device 1580 includes an elongate member 1581, a distal end 1569 that extends interior of the artery and a proximal end that extends exterior of the artery, a plurality of ring elements 1582 configured at the distal end of the elongate member 1581 and a proximal collar 1589 attached to an abutment tube 1588. The ring elements 1582 are self-expandable from a collapsed configuration to an expanded configuration and feature a radial force that biases the ring elements 1582 toward the expanded configuration. Each ring element 1582, comprising a plurality of struts 1583, is made of shape memory material nitinol and is attached to the elongate member 1581 by connecting tethers 1585. Each strut 1583 has a crown element 1587. A tether is wrapped around each ring element 1582 and is attached to the elongate member 1581 by a tether loop 1584 to engage each ring element 1582 to the elongate member 1581 in a tether-loop mechanism. The radial force is absorbed by the tether-loop mechanism to restrain the retrieval device 1580 in the collapsed configuration when it is advancing through a microcatheter (not shown). The elongate member 1581 is retracted proximally thus sliding the tether loop 1584 off the ring element 1582 and disengaging and therefore allowing each ring element 1582 reach the expanded configuration.

Another preferred embodiment of a mechanical clot retrieval device of the present invention is illustrated in FIGS. 21a-21f. The retrieval device 2020 includes an elongate member 2021 having a distal end that extends interior of the artery and a proximal end that extends exterior of the artery, a plurality of ring elements 2022 configured at the distal end of the elongate member 2021, and a plurality of beveled 2029 or recessed 2028 collars 2026 configured at distal and proximal ends of each ring element 2022. The ring elements 2022 are self-expandable from a collapsed configuration to an expanded configuration and comprise a radial force that biases the ring elements 2022 toward the expanded configuration. In the collapsed configuration, the radial force is absorbed by collars 2026. Each ring element 2022, comprising a plurality of struts 2023, is made of shape memory material nitinol and is interconnected by tethers (not labeled) and attached to the elongate member 2021 by ring connecting tethers 2025. Each strut 2023 includes a crown element 2027 with a tab 2024 extending axially and radially inward and may be bevel or square shape in shape. The tab 2024 engages with the collar 2026 to restrain the ring element 2022 to the elongate member 2021 in a collar mechanism. The collar mechanism restrains the retrieval device 2020 in the collapsed configuration when advancing through a microcatheter (not shown). The elongate member 2021 is retracted proximally to disengage it and allow each ring element 2022 reach the expanded configuration.

FIGS. 22a-22d shows a method for using the device 2020 in accordance with the preferred embodiment shown in FIGS. 21a-21f A guidewire (not shown) is inserted in a cerebral artery 2000 and is advanced across an obstructive clot 2001. An intravascular microcatheter 2003 is advanced over the guidewire to a location proximal to the clot 2001 and then a mechanical clot retrieval device 2020, sheathed within a bumper tube 2030, is advanced through the microcatheter 2003 to the clot 2001 in a collapsed configuration. The microcatheter 2003 is retracted when the retrieval device 2020 is located distal of the clot. It is unsheathed to allow ring elements 2022 to reach the expanded configuration. The elongate member 2021 of the retrieval device 2020 allows the physician to manually disengage the collar mechanism and the ring connecting tether 2025 attached to the elongate member 2021. The ring elements 2022 engage or capture the clot 2001 from the distal surface of the clot 2001 and retract the clot 2001 proximally to the microcatheter 2003.

FIGS. 23a-23c depicts a mechanism used in a mechanical clot retrieval device 2040 for engaging a tab 2044 with a collar 2046 in a slight variant with the preferred embodiment shown in FIGS. 21a-21f. The retrieval device 2040 includes an elongate member 2041 having a distal end that extends interior of the artery and a proximal end that extends exterior of the artery, a ring element 2042 configured at the distal end of the elongate member 2041 and a proximal collar 2046. The ring element 2042 is self-expandable from a collapsed configuration to an extended configuration and has a radial force that biases the ring element 2042 toward the expanded configuration. In the collapsed configuration, the radial force is absorbed by the proximal collar 2046. The ring element 2042, comprising plurality of struts 2043, is made of shape memory material nitinol and each strut 2043 has a crown element 2047 with a tab 2044 extending axially and radially inward. The tab 2044 is shaped to engage with the collar 2046, having a recess to restrain the ring element 2042 to the elongate member 2041 in a collar mechanism. The collar mechanism restrains the retrieval device 2040 in the collapsed configuration when advancing through a microcatheter (not shown). The elongate member 2041 is retracted proximally to disengage it and allow each ring element 2042 reach the expanded configuration.

Figure 24A:
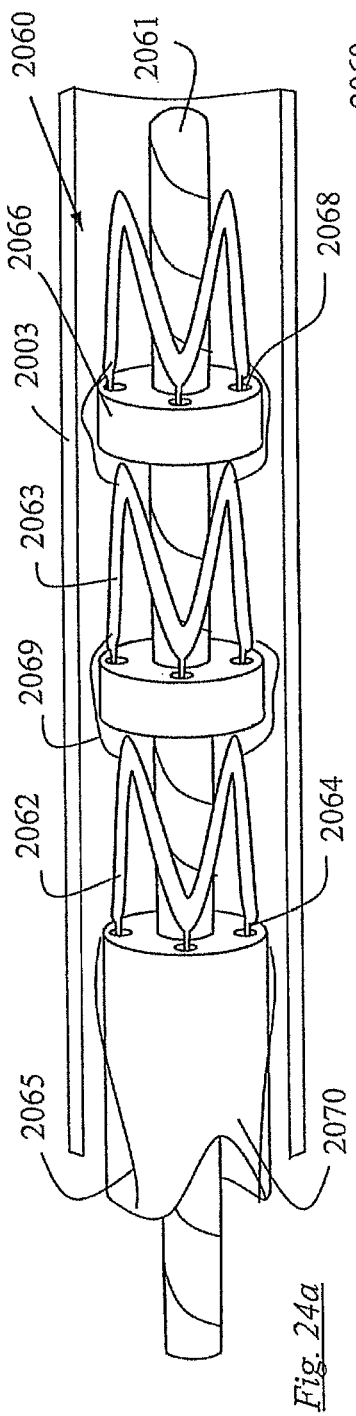
FIGS. 24a-24c illustrate a further clot retrieval device of the invention.
Figure 24B:
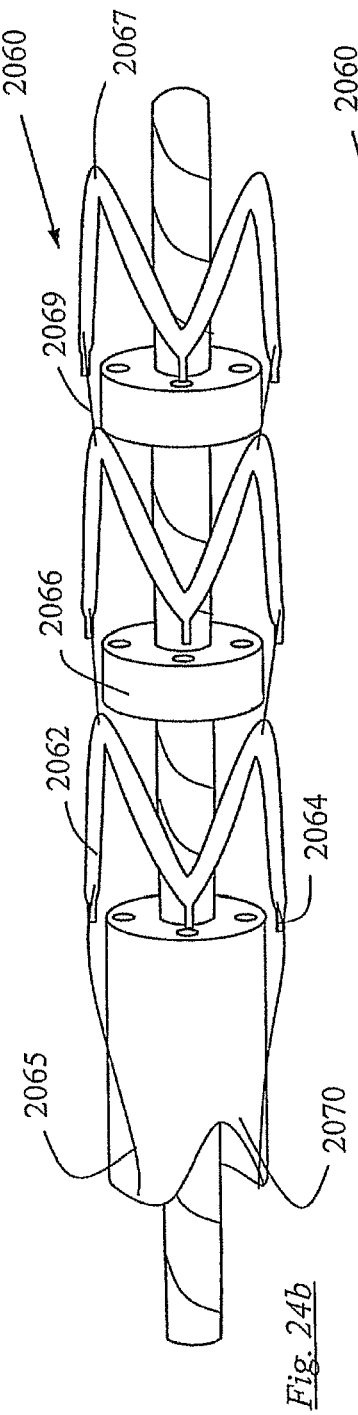
Figure 24C:
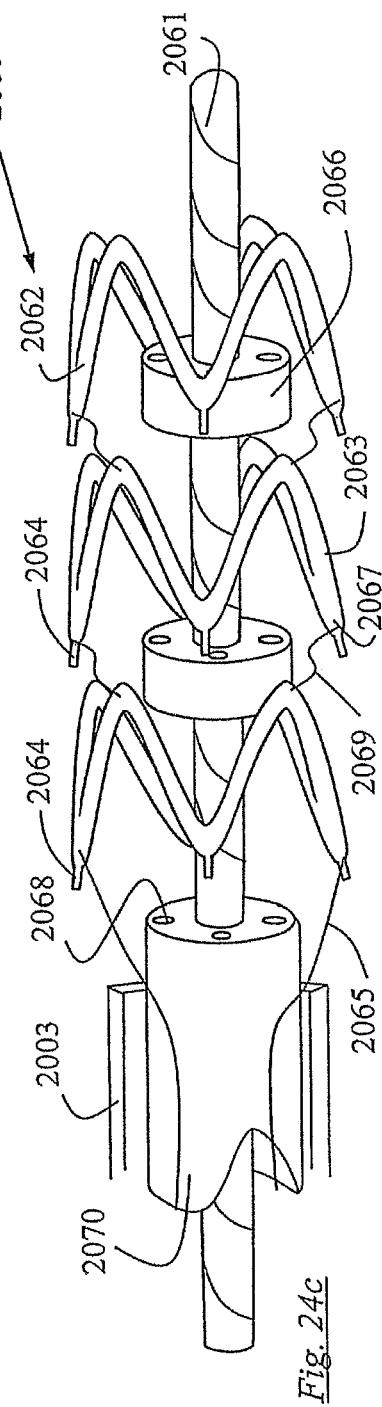

FIGS. 24a-24c shows a mechanical clot retrieval device 2060 of the present invention which is a slightly variant embodiment of the retrieval device 2020 as illustrated in FIGS. 21a-21f The retrieval device 2060 includes an elongate member 2061 having a distal end that extends interior of the artery and a proximal end that extends exterior of the artery, a plurality of ring elements 2062 configured at the distal end of the elongate member 2061, and a plurality of collars 2066 having a plurality of holes 2068 configured proximally of each ring element 2062. The ring members 2062 are self-expandable from a collapsed configuration to an expanded configuration and comprise a radial force that biases the ring elements 2062 toward the expanded configuration. In the collapsed configuration, the radial force is absorbed by collars 2066. Each ring element 2062, comprising a plurality of struts 2063, is made of shape memory material nitinol and is interconnected by ring connecting tethers 2069. Each strut 2063 has a crown element 2067 with a pin 2064 extending axially and radially inward. The pin 2064 engages with the hole 2068 to restrain the ring elements 2062 to the elongate member 2061 in a collar mechanism. The device includes a pair of cables 2065 having distal ends which are attached to the most proximal ring element 2062 and proximal ends that extend exterior of the artery for manipulation and control by the physician. The collar mechanism restrains the retrieval device 2060 in the collapsed configuration when it is advancing through a microcatheter 2003. The cables 2065 are manually pulled proximally to disengage the collar mechanism and allow each ring element 2062 reach the expanded configuration.

FIGS. 25a-25k represents a mechanical clot retrieval device 2080 of the present invention which is another slightly variant embodiment of the retrieval device 2020 as illustrated in FIGS. 21a-21f. The retrieval device 2080 includes elongate member 2081 a distal end that extends interior of the artery and a proximal end that extends exterior of the artery, a plurality of ring elements 2082 configured at the distal end of the elongate member 2081, and a plurality of shaped engagement collars 2085 having a plurality of dove tail grooves 2088 configured proximally of each ring element 2082. The ring elements 2082 are self-expandable from a collapsed configuration to an expanded configuration and comprise a radial force that biases the ring elements 2082 toward the expanded configuration. In the collapsed configuration, the radial force is absorbed by collars 2085. Each ring element 2082, comprising a plurality of struts 2083, is made of shape memory material nitinol and is attached to the elongate member 2081 by tethers 2089. Each strut 2083 has a crown element 2087 with a shaped tab 2084 extending axially and radially inward. The shaped tab 2084 engages with the shaped engagement collar 2085 to restrain the ring element 2082 to the elongate member 2081 in a collar mechanism. The collar mechanism restrains the retrieval device 2080 in the collapsed configuration when it is advancing through a microcatheter (not shown). The elongate member 2081 is manually retracted proximally to disengage it and allow each ring element 2082 reach the expanded configuration.

FIGS. 26a-26c represents a slightly variant embodiment of the retrieval device 2080 as represented in FIGS. 25a-25k, having additional ring connecting tethers 2101 interconnecting each ring element 2082.

Another preferred embodiment of a mechanical clot retrieval device 2520 of the present invention is illustrated in FIGS. 27a-27b. The retrieval device 2520 includes an elongate member 2521 having a distal end that extends interior of the artery, a proximal end that ends interior of the artery and an inner lumen 2529 with a plurality of openings (not labeled), and a plurality of ring elements 2522 configured at the distal end of the elongate member 2521. The ring elements 2522 are self-expandable from a collapsed configuration to an expanded configuration and comprise a radial force that biases ring elements 2522 toward the expanded configuration. Each ring element 2522, comprising a plurality of struts 2523, is interconnected by ring connecting tethers 2525. Each strut 2523 has a crown element 2527 and an engagement tab 2524. A plurality of tether loops 2526 having proximal ends that extend exterior of the lumen 2529 is advanced out of each opening (not opening) to circle the engagement tab 2524 and engage each ring element 2522 to the elongate member 2521 in an eyelet mechanism. The radial force is absorbed by the eyelet mechanism to restrain the retrieval device 2520 in the collapsed configuration when it is advancing through a microcatheter (not shown). The tethers are manually pulled proximally to disengage them and allow each ring element 2522 to reach the expanded configuration.

FIGS. 28a-28b represents a mechanical clot retrieval device 2540 of the present invention which is a slightly variant embodiment of the retrieval device 2520 as illustrated in FIGS. 27a-27b. The retrieval device 2540 includes an elongate member 2541 having a distal end that extends interior of the artery, a proximal end that extends exterior of the artery and a plurality of raised tabs 2548, and a plurality of ring elements 2542 configured at the distal end of the elongate member 2541. The ring elements 2542 are self-expandable from a collapsed configuration to an expanded configuration and comprise a radial force that biases the ring elements 2542 toward the expanded configuration. In the collapsed configuration, the radial force is absorbed by raised tabs 2548. Each ring element 2542, comprising a plurality of struts 2543, is interconnected by ring connecting tethers 2545. Each strut 2543 has a crown element and an engagement tab 2544. The engagement tab 2544 engages with the raised tab 2548 to restrain the ring element 2542 to the elongate member 2541 in an eyelet mechanism. The eyelet mechanism restrains the retrieval device 2540 in the collapsed configuration when it is advancing through a microcatheter (not shown). The elongate member 2541 is manually retracted proximally to disengage it and allow each ring element 2542 to reach the expanded configuration.

FIGS. 29a-29h shows a method for using a mechanical clot retrieval device 2560 in accordance with the preferred embodiment shown in FIGS. 27a-27b and 28a-28b. A guidewire 2502 is inserted in a cerebral artery 2500 and is advanced through an obstructive clot 2501. An intravascular microcatheter 2503 is advanced over the guidewire 2502 to a location distal to the clot 2501 and then the retrieval device 2560 is advanced through the microcatheter 2503 to the clot 2501 in a collapsed configuration. The microcatheter 2503 is retracted when the retrieval device 2560 is positioned distal of the clot 2501 to allow a plurality of ring elements 2562 to reach an expanded configuration. The ring elements 2562, comprising a plurality of struts 2563, are interconnected by ring connecting tethers 2565. A tether 2564 is attached at a distal end of the retrieval device 2560 and its proximal end extends out of the artery. The elongate member 2561 and tether 2564 allows the physician to manually disengage eyelet mechanism. The ring elements 2562 engage or capture the clot 2501 from the distal end of the clot 2501 and retract the clot 2501 proximally to the microcatheter 2504.

Another embodiment of a mechanical clot retrieval device 3020 of the present invention is illustrated in FIGS. 30*a*-30*e*. The retrieval device 3020 includes an elongate member 3021 designed to have a distal end that extends interior of the artery, a proximal end that extends exterior of the artery, a plurality of engagement diameters 3028 and a plurality of disengagement diameters 3029, a plurality of ring elements 3022 configured at the distal end of the elongate member 3021, and a proximal abutment tube 3031. The ring elements 3022 are self-expandable from a collapsed configuration to an expanded configuration and comprise a radial force that biases the ring elements 3022 toward the expanded configuration. In the collapsed configuration, the radial force is absorbed by the engagement diameters. Each ring element 3022 comprising a plurality of struts 3023 is interconnected by ring connecting tethers 3025. Each strut 3023 has a crown element 3027 with a C-shaped engagement tab 3030 extending radially inward. The C-shaped engagement tab 3030 engages with the engagement diameter 3028 to restrain the ring element 3022 to the elongate member 3021 in the collapsed configuration when it is advanced through a microcatheter (not shown). The device features a pair of control tethers 3026 having distal ends which are attached to the crown element 3027 of the most proximal ring element 3022. The axial movement of the elongate member 3021 disengages each ring element 3022 at the disengagement diameter 3029 and allows each ring element 3022 to reach the expanded configuration.

FIGS. 31*a*-31*e* shows a mechanical clot retrieval device 3040 of the present invention which is a slightly variant embodiment of the retrieval device 3020 as illustrated in FIGS. 30*a*-30*e*. The retrieval device 3040 includes an elongate member 3041 having a distal end that extends interior of the artery, a proximal end that extends exterior of the artery and an inner wire 3051, a plurality of ring elements 3042 arranged at a distal end of the elongate member 3041, and a proximal abutment tube 3052. The ring elements 3042 are self-expandable from a collapsed configuration to an expanded configuration and comprise a radial force that biases the ring elements 3042 toward the expanded configuration. In the collapsed configuration, the radial force is absorbed by the elongate member having inner wire 3051. Each ring element 3042 comprising a plurality of struts 3042 is interconnected by ring connecting tethers 3045. Each strut 3043 has a crown element 3047 with a C-shaped engagement tab 3050 extending radially inward. The C-shaped engagement tab 3050 engages with the elongate member 3041. The inner wire 3051 restrains the retrieval device 3040 in the collapsed configuration when it is advanced through a microcatheter (not shown). The device features a pair of control tethers 3046 having distal ends which are attached to the crown element 3047 of the most proximal ring element 3042 and proximal ends which are attached to the abutment tube 3052. The withdrawal of the inner wire 3051 disengages it and allows each ring element 3042 reach the expanded configuration.

FIGS. 32*a*-32*d* illustrates the mechanical clot retrieval device 3060 of the present invention. The retrieval device 3060 includes an elongate member 3061 having a distal end that extends interior of the artery, a proximal end that extends exterior of the artery and an inner lumen 3071 with a plurality of slots 3070, a plurality of ring elements 3062 configured at the distal end of the elongate member 3061, and a proximal collar 3066. The ring elements 3062 are self-expandable from a collapsed configuration to an expanded configuration and comprise a radial force that biases the ring elements 3062 toward the expanded configuration. In the collapsed configuration, the radial force is absorbed by slots 3070. Each ring element 3062, comprising a plurality of struts 3063, is interconnected by ring connecting tethers 3065. Each strut 3063 has a crown element 3067 with a stepped engagement tab 3064 extending longitudinally and radially. The engagement tab 3064 engages with the slot 3070 to restrain the ring elements 3062 to the elongate member 3061 and to restrain the retrieval device 3060 in the collapsed configuration when it is advanced through a microcatheter (not shown). A pair of control tethers 3068 is attached from the crown element 3067 of the most proximal ring element 3062, to the proximal collar 3066. The proximal collar 3066 is manually pulled proximally to disengage it and allow the ring elements 3062 to reach an expanded configuration.

FIGS. 33*a*-33*g* represents another embodiment of a mechanical clot retrieval device of the present invention. The retrieval device 3080 includes an elongate member 3081 having a distal end that extends interior of the artery, a proximal end that extends exterior of the artery and a plurality of monofilaments 3088, a plurality of ring elements 3082 configured at the distal end of the elongate member 3081, and a proximal collar 3086. The ring elements 3082 are self-expandable from a collapsed configuration to an expanded configuration and comprise a radial force biasing the ring elements 3082 toward the expanded configuration. In the collapsed configuration, the radial force is absorbed by the monofilaments. Each ring element 3082 comprising a plurality of struts 3083 is interconnected by ring connecting tethers 3085. Each strut 3082 has a crown element 3087 with a C-shaped engagement tab 3084. The C-shaped engagement tab 3084 engages with the monofilament 3088 to restrain the ring element 3082 to the elongate member 3081 in a snap-fit mechanism. The snap-fit mechanism restrains the retrieval device 3080 in the collapsed configuration when it is advancing through a microcatheter (not shown). The device contains a pair of control tethers 3089 having distal ends which are attached to the crown element 3087 of the most proximal ring element 3082 and proximal ends which are attached to the collar 3086. The elongate member 3081 is manually retracted to disengage it and allow each ring element 3082 reach the expanded configuration.

Another embodiment of a mechanical clot retrieval device of the present invention is shown in FIGS. 34*a*-34*j*. The retrieval device 3100 includes an elongate member 3101 having a distal end that extends interior of the artery, a proximal end that extends exterior of the artery and a plurality of inactivated cuffs 3108*a* configured at the distal end of the elongate member 3101, a plurality of ring elements 3102 configured over the cuff 3108*a*, and a tube 3106. Each cuff 3108*a* is made of electro-active polymer which swells to an activated state 3108*b* when current is applied. The ring elements 3102 are self-expandable from a collapsed configuration to an expanded configuration and comprise a radial force biasing the ring elements 3102 toward the expanded configuration. Each ring element 3102 comprising a plurality of struts 3103 is interconnected by ring connecting tethers 3105. Each strut has a crown element 3107. A pair of control tethers 3104 are attached to the crown element 3107 of the most proximal ring element 3102, having proximal ends that extend out of the artery. A ring restraining tether 3109 is wrapped around each ring element 3102 restraining it to the elongate member 3101 in the collapsed configuration when it is advanced through a microcatheter (not shown). In the collapsed configuration, the radial force is absorbed by the ring restraining tethers 3109. The current is applied through the restraining tether 3109 to allow each cuff 3108a to reach activated state 3108b and then they are manually pulled proximally to disengage them and allow each ring element 3102 reach the expanded configuration.

Figures 35A, 35B:
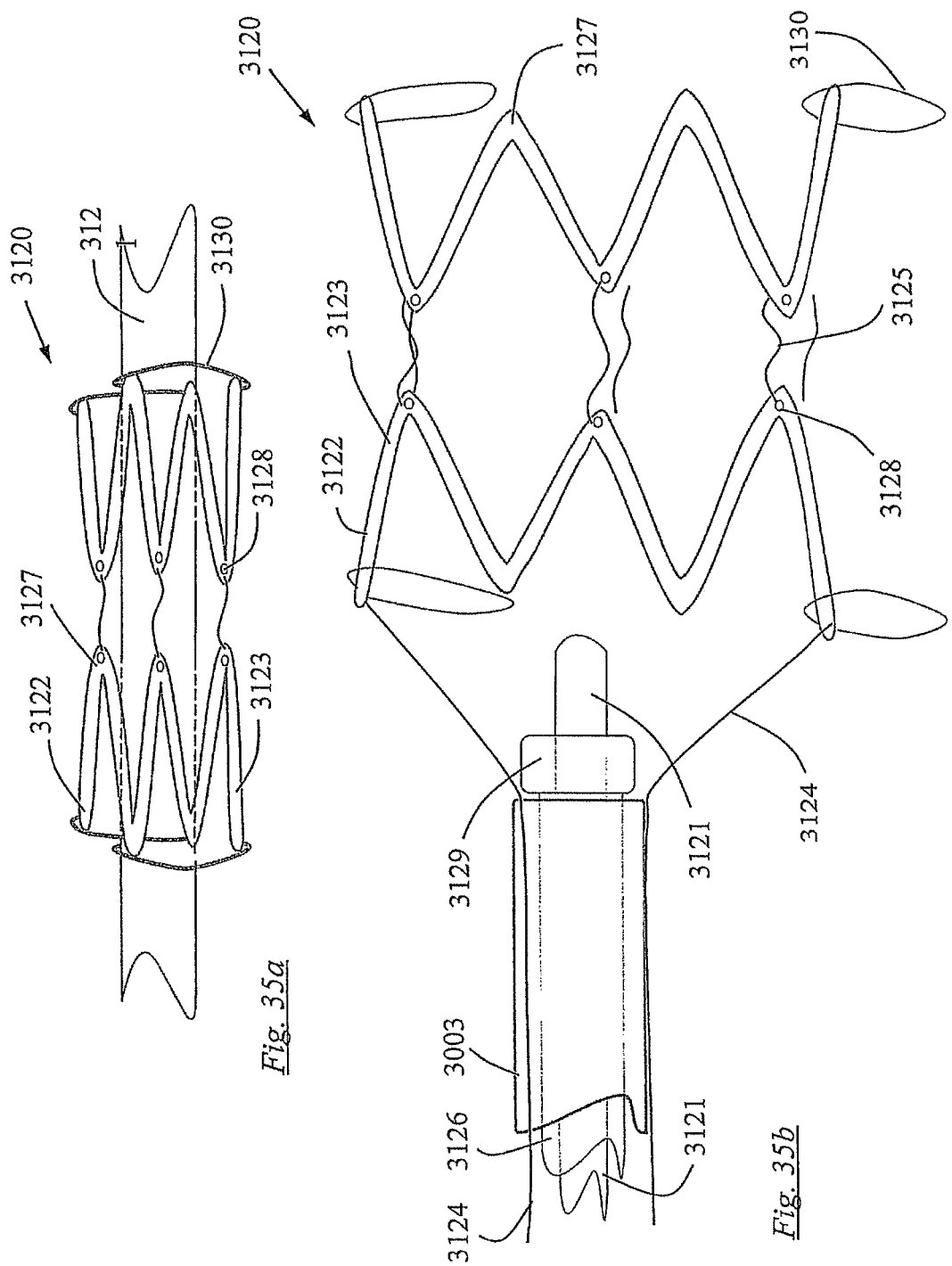
FIGS. 35a-35b illustrate a further clot retrieval device of the invention.
Figures 37A, 37B, 37C, 37D:
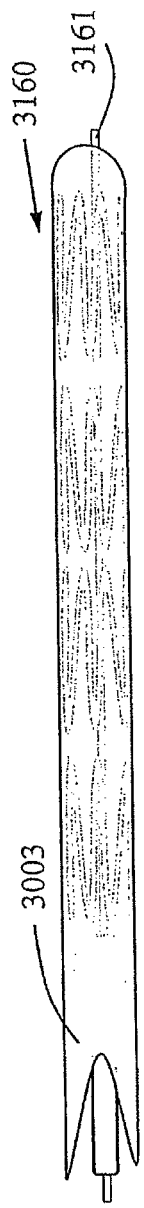
Figure 38A:
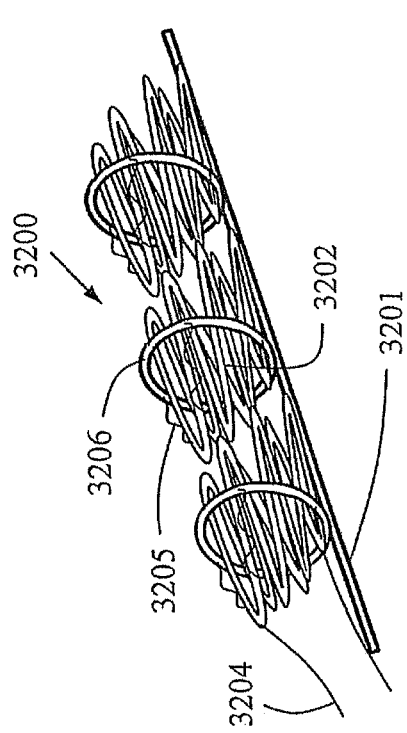
FIGS. 38a-38d illustrate another clot retrieval device of the invention.
Figure 38B:
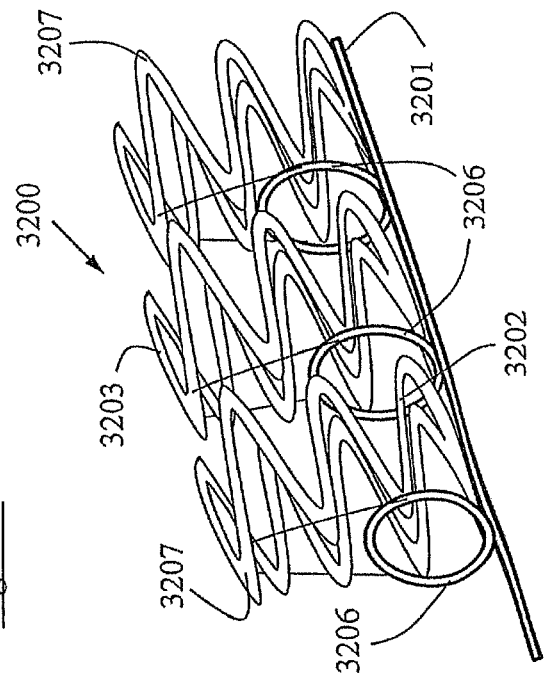
Figure 38C:
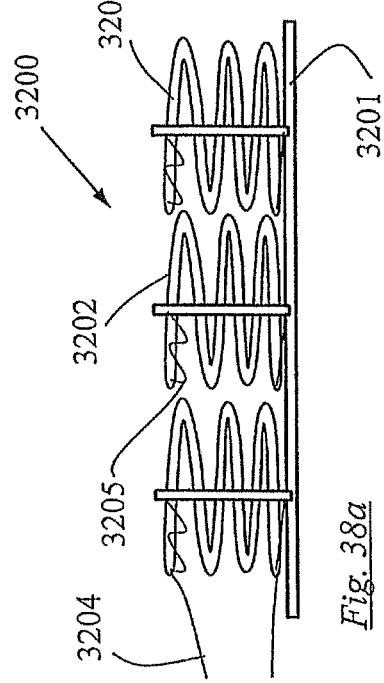
Figure 38D:
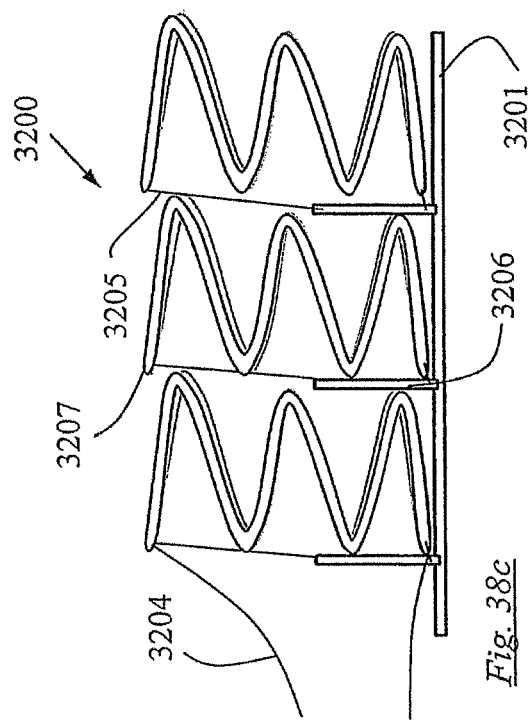

FIGS. 35a-35b represents another embodiment of a mechanical clot retrieval device of the present invention. The retrieval device 3120 includes an elongate member 3121 having a distal end that extends interior of the artery and a proximal end that extends exterior of the artery, a plurality of ring elements 3122 configured at the distal end of the elongate member 3121, a proximal collar 3129, and a bumper tube 3126. The ring elements 3122 are self-expandable from a collapsed configuration to an expanded configuration and have a radial force biasing the ring elements 3122 toward the expanded configuration. Each ring element 3122, comprising a plurality of struts 3123, is interconnected by ring connecting tethers 3125. Each strut 3123 has a crown element 3127 with an eyelet 3128. A tether loop 3130 engages each ring element 3122 to the elongate member 3121 to restrain the retrieval device 3120 in the collapsed configuration when it is advancing through a microcatheter 3003. In the collapsed configuration, the radial force is absorbed by tether loops 3130. The device contains a pair of control tethers 3124, having distal ends which are attached to the crown element 3127 of the most proximal ring element 3122 and proximal ends which extend out of the artery. The elongate member 3121 is manually retracted proximally to disengage it and allow each ring element 3122 reach the expanded configuration.

Another embodiment of a mechanical clot retrieval device of the present invention is shown in FIGS. 36a-36d. The retrieval device 3140 includes an elongate member 3141 having a distal end that extends interior of the artery and a proximal end that extends exterior of the artery, a plurality of ring elements 3142 arranged at the distal end of the elongate member 3141, a bumper tube 3146 and a proximal collar 3149. The ring elements 3142 are self-expandable from a collapsed configuration to an expanded configuration and comprise a radial force biasing ring elements toward the expanded configuration. In the collapsed configuration, the radial force is absorbed by the elongate member 3141. Each ring element 3142 comprising a plurality of struts 3143 is interconnected by ring connecting tethers 3145. Each strut 3143 has a crown element 3147 with an engagement tab 3148 having an eyelet 3144. The elongate member 3141 passes through each eyelet 3144 engaging each ring element 3142 to the elongate member 3141 to restrain the retrieval device 3140 in the collapsed configuration when it is advancing through a microcatheter 3003. The elongate member 3141 is manually retracted proximally to disengage it and allow each ring element 3142 reach the expanded configuration.

FIGS. 37a-37i represents a mechanical clot retrieval device of the present invention which is a slightly variant embodiment of the retrieval device 3140 as shown in FIGS. 36a-36d. The retrieval device 3160 includes an elongate member 3161 having a distal end that extends interior of the artery and a proximal end that extends exterior of the artery, a plurality of ring elements 3162 configured at the distal end of the elongate member 3161, a bumper tube (not labeled) and a proximal collar (not labeled). The ring elements 3162 are self-expandable from a collapsed configuration to an expanded configuration and comprise a radial force biasing the ring elements 3162 toward the expanded configuration. In the collapsed configuration, the radial force is absorbed by the elongate member 3161. Each ring element 3162 comprising a plurality of struts 3163 is interconnected by ring connecting tethers (not labeled). Each strut has a crown element 3167 with an engagement tab 3166 and an eyelet 3168. The elongate member 3161 passes through each eyelet 3168 engaging each ring element 3162 to the elongate member 3161 to restrain the retrieval device 3160 in the collapsed configuration when it is advancing through a microcatheter 3003. The elongate member 3161 is manually retracted proximally to disengage and allow each ring element 3162 reach the expanded configuration.

Another embodiment of a mechanical clot retrieval device of the present invention is illustrated in FIGS. 38a-38d. The retrieval device 3200 has an elongate member 3201 having a distal end that extends interior of the artery, a proximal end that extends exterior of the artery and a plurality of restraining loops 3206 configured at the distal end of the elongate member 3201, and a plurality of ring elements 3202 arranged at the distal end of the elongate member 3201. The ring elements 3202 are self-expandable from a collapsed configuration to an expanded configuration and comprise a radial force that biases the ring elements 3202 toward the expanded configuration. In the collapsed configuration, the radial force is absorbed by the restraining loops 3206. Each ring element 3202 comprising a plurality of struts 3203 is connected to the loop 3206 by connecting tethers 3205. Each strut 3203 is having a crown element 3207. The device features a pair of control tethers 3204, having distal ends which are attached to the crown element 3207 of the most proximal ring element 3202, and proximal ends that extend out of the artery. The loops 3206 engage the ring elements 3202 to the elongate member 3201 in an offset loop mechanism. The offset loop mechanism restrains the retrieval device 3200 in the collapsed configuration when it is advanced through a microcatheter (not shown). The elongate member 3201 is manually retracted proximally to disengage it and allow each ring element 3202 to reach the expanded configuration.

Another embodiment of a mechanical clot retrieval device 3300 of the present invention is illustrated in FIGS. 39a-39d. The retrieval device 3300 has an elongate member 3301 having a distal end that extends interior of the artery and a proximal end that extend exterior of the artery, a plurality of ring elements 3302 arranged at the distal end of the elongate member 3301, a bumper tube 3306, and a proximal collar 3308. The ring elements 3302 are self-expandable from a collapsed configuration to an expanded configuration and comprise a radial force that biases the ring elements toward the expanded configuration. In the collapsed configuration, the radial force is absorbed by the elongate member 3301. Each ring element 3302, comprising a plurality of struts 3303, is interconnected by ring connecting tethers 3305. Each strut 3303 has a crown element 3307. The device has comprises a pair of control tethers 3304, having distal ends which are attached to the crown element 3307 of the most proximal ring element 3302 and proximal ends that are attached to the bumper tube 3306. The crown element 3307 of each strut 3303 is confined around the elongate member 3301 to restrain the ring element 3302 to the elongate member 3301 when it is advanced through a microcatheter 3309. The elongate member 3301 is retracted proximally to disengage it and allow each ring element 3302 to reach the expanded configuration.

FIGS. 40a-40e and 41a-41d shows a method of advancing a mechanical clot retrieval device 3405 in accordance with a preferred embodiment of the present invention in a tortuous vessel 3400. A guidewire 3402 is inserted in the vessel 3400 and is advanced through an obstructive clot 3401. An intravascular microcatheter 3403 is advanced over the guidewire to a location distal to the clot 3401 and then the retrieval device 3405 is advanced through the microcatheter 3403 to the clot 3401 in a collapsed configuration. The microcatheter 3403 is retracted to allow the plurality of ring elements (not labeled) to reach an expanded configuration. The ring elements (not labeled) contain a plurality of struts (not labeled). Each ring element is connected to the next ring element (not labeled) by a ring connecting tether 3406. A control tether 3407 is attached to the strut (not labeled) of the proximal ring element having a proximal end that extends out of the patient to allow physician to manually maneuver the retrieval device 3405. The retrieval device 3405 engages or captures the clot 3401 from the distal end of the clot 3401 and retracts the clot 3401 proximally into the microcatheter 3403.

FIGS. 42a-42d, 43a-43h and 44a-44b illustrates the mechanical clot retrieval device 3420 of the present invention. The retrieval device 3420 includes an elongate member 3421 having a distal end that extends interior of the artery and a proximal end that extends exterior of the artery, and a plurality of ring elements 3422 configured at the distal end of the elongate member 3421. The ring elements 3422 are self-expandable from a collapsed configuration to an expanded configuration and comprise a radial force that biases the ring elements 3422 toward the expanded configuration. In the collapsed configuration, the radial force is absorbed by an intravascular microcatheter (not shown) through which the retrieval device 3420 is delivered inside the artery. Each ring element 3422, comprising a plurality of struts 3423, is interconnected by ring connecting tethers 3425. Each strut 3423 has a crown element 3427 with or without a shaped tab 3428 or an eyelet 3426. The crown element 3427 is connected to neighboring crown element 3427 by the tether 3425 which may be looped around tab 3428 or passed through eyelet 3426.

The crown element 3427 which is without the shaped tab 3428 or the eyelet 3426 may be connected to neighboring crown element 3427 by an adhesive bond 3429. Crown-to-crown 3427 connection restrains the retrieval device 3420 in the collapsed configuration when advanced through the intravascular microcatheter (not shown). The device features a pair of removal tethers 3424, having distal ends which are attached to the crown element 3427 of the most proximal ring element 3422, and proximal ends that extend out of the artery. The microcatheter is retracted proximally and tether 3424 is manually pulled proximally to disengage it and allow each ring element 3422 reach the expanded configuration.

Figure 45:
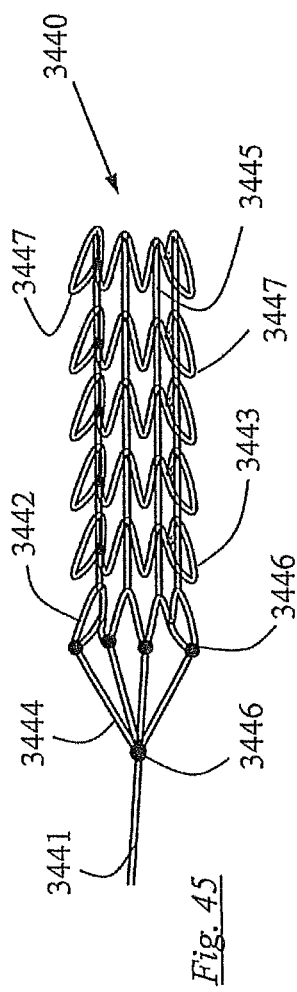
FIG. 45 illustrates another clot retrieval device of the invention.

Another embodiment of a mechanical clot retrieval device of the present invention is represented in FIG. 45. The retrieval device 3440 has an elongate member 3441 having a distal end that extends interior of the artery and a proximal end that extends exterior of the artery, a plurality of ring elements 3442 having a first diameter and a second diameter, and a control strut 3444 having distal end attached to proximal ring element 3442 and proximal end attached to the elongate member 3441 by adhesive bonds 3446. The ring elements 3442 are self-expandable from a collapsed configuration to an expanded configuration and have a radial force that biases the ring elements 3442 toward the expanded configuration. In the collapsed configuration, the radial force is absorbed by an intravascular microcatheter (not shown) through which the retrieval device 3440 is delivered inside the artery. Each ring element 3442, comprising a plurality of struts 3443, is connected by ring connecting tethers 3445. Each strut 3443 has a crown element 3447. The crown element 3447 is connected to neighboring crown element 3447 by the tether 3445. Crown-to-crown connection restrains the retrieval device 3440 in the collapsed configuration when it is advanced through the microcatheter (not shown). The microcatheter is retracted proximally and each ring element 3442 disengages to create a zigzag stent surface for improved clot engagement.

Figure 46:
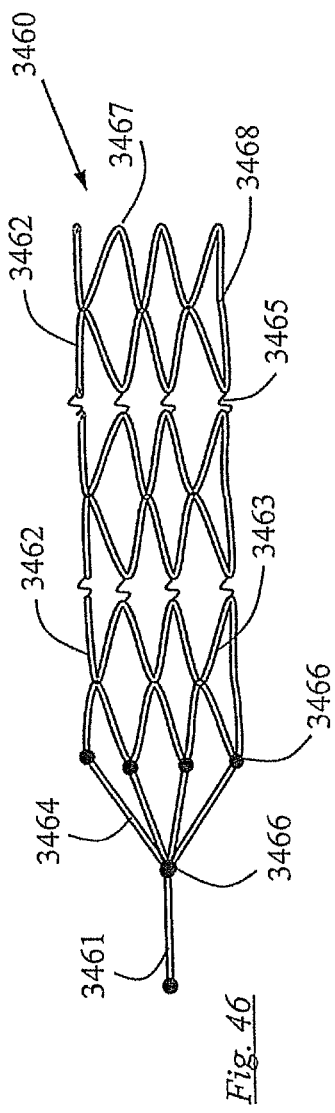
FIG. 46 illustrates a further clot retrieval device of the invention.

FIG. 46 represents a mechanical clot retrieval device 3460 of the present invention which is a slightly variant embodiment of the retrieval device as illustrated by FIG. 46. The retrieval device 3460 has an elongate member 3461 having a distal end that extends interior of the artery and a proximal end that extends exterior of the artery, a plurality of ring elements 3462 attached at the distal end of the elongate member and a control strut 3464 having a distal end attached to the most proximal ring element 3462 and a proximal end attached to the elongate member 3461 by adhesive bonds 3466. The ring elements 3462 are self-expandable from a collapsed configuration to an expanded configuration and comprise a radial force that biases the ring elements toward the expanded configuration. In the collapsed configuration, the radial force is absorbed by an intravascular microcatheter (not shown) through which the retrieval device 3460 is delivered inside the artery. Each ring element 3462, comprising a plurality of struts 3463, is connected by ring connecting tethers 3465. Each strut 3463 has a crown element 3467. The crown element 3467 is connected to the neighboring crown 3467 by a connecting strut 3468 to restrain the retrieval device 3460 in the collapsed configuration when it is advanced through the microcatheter (not shown). The microcatheter is retracted proximally and each ring element 3462 disengages to create a zigzag stent surface for improved clot engagement.

Figure 47:
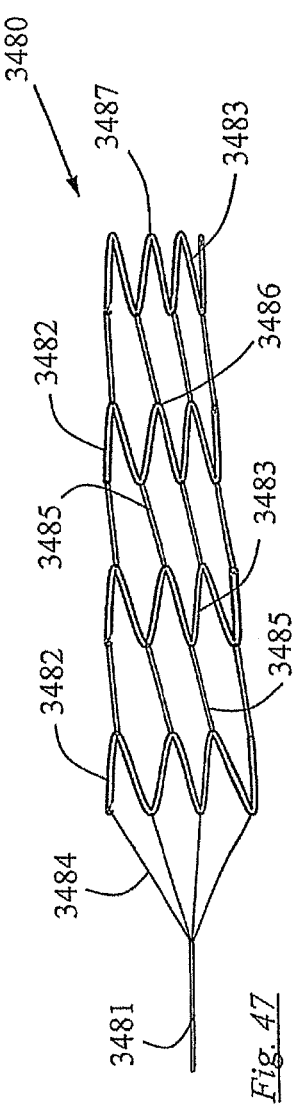
FIG. 47 illustrates another clot retrieval device of the invention.

FIG. 47 represents a mechanical clot retrieval device 3480 of the present invention which is another variant embodiment of the retrieval device as illustrated in FIG. 46. The retrieval device 3480 has an elongate member 3481 having a distal end that extends interior of the artery and a proximal end that extends exterior of the artery, a plurality of ring elements 3482 and a control strut 3484 having a distal end attached to the proximal ring element 3482 and a proximal end attached to the elongate member 3481. The ring elements 3482 are self-expandable from a collapsed configuration to an expanded configuration and have a radial force that biases the ring elements 3482 toward the expanded configuration. In the collapsed configuration, the radial force is absorbed by an intravascular microcatheter, through which the retrieval device 3480 is delivered inside the artery. Each ring element 3482, comprising a plurality of struts 3483, is connected by ring connecting tethers 3485. Each strut 3483 has a crown element 3487. The crown element 3487 is connected to the neighboring crown 3487 by the tether 3485 and adhesive bond 3486. Crown-to-crown connection restrains the retrieval device 3480 in the collapsed configuration when it is advanced through a microcatheter (not shown). The microcatheter is retracted and each ring element 3482 disengages to create a zigzag stent surface for improved clot engagement.

Another preferred embodiment of a mechanical clot retrieval device of the present invention is illustrated in FIGS. 48a-48f. The retrieval device 3500 includes an elongate member 3501 having a distal end that extends interior of the artery and a proximal end that extends exterior of the artery, a plurality of ring elements 3502, and a pair of removal tethers 3504 having distal ends attached to the proximal ring element 3502 and proximal ends attached to the elongate member 3501. The ring elements 3502 are self-expandable from a collapsed configuration to an expanded configuration and have a radial force that biases the ring elements 3502 toward the expanded configuration. In the collapsed configuration, the radial force is absorbed by an intravascular microcatheter 3403, through which the retrieval device 3500 is delivered inside the artery. Each ring element 3502, comprising a plurality of struts 3503, is interconnected by ring connecting tethers 3505. Each strut 3503 has a crown element 3507. The distally facing crown element 3507 is connected to the neighboring proximally facing crown 3507 by the tether 3505. Crown-to-crown connection restrains the retrieval device 3500 in the collapsed configuration when advanced through the microcatheter 3403. The microcatheter 3403 is advanced inside a torturous artery 3400 and is positioned distal of an obstructive clot 3401. The microcatheter 3403 is retracted to allow each ring element 3502 reach the expanded configuration and engage or capture the clot 3401 from the distal end of the clot 3401 and the device is then retracted proximally into the microcatheter 3403.

FIGS. 49a-49f represents a mechanical clot retrieval device of the present invention which is a slightly variant embodiment of the retrieval device 3500 as illustrated in FIGS. 48a-48f. The retrieval device has an elongate member 3521 having a distal end that extends interior of the artery and a proximal end that extends exterior of the artery, a plurality of ring elements 3522, and a control strut 3524 having a distal end attached to the proximal ring element 3522 and a proximal end attached to the elongate member 3521. The ring elements 3522 are self-expandable from a collapsed configuration to an expanded configuration and comprise a radial force that biases the ring elements 3522 toward the expanded configuration. In the collapsed configuration, the radial force is absorbed by an intravascular microcatheter 3403 through which the retrieval device 3520 is delivered inside the artery. Each ring element 3522, comprising a plurality of struts 3523, is connected by ring connecting tethers 3525. Each strut 3523 has a crown element 3527. The distally facing crown element 3527 is connected to neighboring proximally facing crown 3527 by the tether 3525. Crown-to-crown 3527 connection restrains the retrieval device 3520 in the collapsed configuration when advanced through the microcatheter 3403. The microcatheter 3403 is advanced over a guidewire (not shown) inside a torturous artery 3400 and positioned distal of an obstructive clot 3401. The microcatheter 3403 is retracted proximally to allow each ring element 3522 reach the expanded configuration and engage or capture the clot 3401 from the distal end of the clot 3401 and the device is then retracted proximally into the microcatheter 3403.

FIGS. 50a-50g shows a mechanical clot retrieval device 3540a of the present invention which is another slightly variant embodiment of the retrieval device 3500 as illustrated in FIGS. 48a-48f. The retrieval device 3540a includes an elongate member 3541 having a distal end that extends interior of the artery and a proximal end that extends exterior of the artery, a plurality of ring elements 3542 configured at the distal end of the elongate member 3541 and a plurality of connecting tethers 3545 having distal ends attached to the ring element 3542 and proximal ends attached to the elongate member 3541. The ring elements 3542 are self-expandable from a collapsed configuration to an expanded configuration and comprise a radial force that biases the ring elements 3542 toward the expanded configuration. In the collapsed configuration, the radial force is absorbed by an intravascular microcatheter 3403 through which the retrieval device 3540a is delivered inside the artery. Each ring element 3542 comprising a plurality of struts 3543. Each strut 3543 has a crown element 3547. The distally facing crown element 3547 is connected to neighboring proximally facing crown 3547 by the tether 3545. Crown-crown 3547 connection restrains the retrieval device 3540a in the collapse configuration when advanced through a microcatheter 3403. The microcatheter 3403 is advanced over a guidewire (not shown) inside a tortuous artery 3400 and positioned distal of an obstructive clot 3401. The microcatheter 3403 is retracted to allow each ring element 3542 to reach the expanded configuration and engage or capture the clot 3401 from the distal base of the clot 3401 and the device is then retracted proximally to the microcatheter 3403.

Another embodiment of a mechanical clot retrieval device 3560 of the present invention is illustrated in FIGS. 51a-51f. The retrieval device 3560 includes an elongate member 3561 having a distal end that extends interior of the artery and a proximal end that extends exterior of the artery, a plurality of ring elements 3562 configured at the distal end of the elongate member 3561, a plurality of connecting tethers 3565 having distal ends attached to the ring element 3562 and proximal ends attached to the elongate member 3561, and a pair of removal tethers 3564 having distal ends attached to the most proximal ring element 3562 and proximal ends that extend out of the artery. The ring elements 3562 are self-expandable from a collapsed configuration to an expanded configuration and comprise a radial force that biases the ring elements 3562 toward the expanded configuration. In the collapsed configuration, the radial force is absorbed by an intravascular microcatheter 3403 through which the retrieval device 3560 is delivered inside the artery. Each ring element 3562 comprises a plurality of struts 3563. Each strut 3563 has a crown element 3567. The connecting tether 3565 engages each ring element 3562 to the elongate member 3562 to restrain the retrieval device 3560 in the collapsed configuration when it is advanced through a microcatheter 3403. The microcatheter 3403 is advanced over a guidewire (not shown) inside a tortuous artery 3400 and positioned distal of an obstructive clot 3401. The microcatheter 3403 is retracted to allow each ring element 3562 reach the expanded configuration and engage or capture the clot 3401 from the distal base of the clot 3401 and retracted proximally to the microcatheter 3403.

FIGS. 52a-52d represents a mechanical clot retrieval device 3580 of the present invention which is a slightly variant embodiment of the retrieval device 3560 as illustrated in FIGS. 51a-51f. The retrieval device 3580 has an elongate member 3581 having a distal end that extends interior of the artery and a proximal end that extends exterior of the artery, a plurality of ring elements 3582 configured at the distal end of the elongate member 3581 and a plurality of connecting tethers 3585 having distal ends attached to the ring member 3582 and proximal ends attached to the elongate member 3581. The ring elements 3582 are self-expandable from a collapsed configuration to an expanded configuration and comprise a radial force that biases the ring elements 3582 towards the expanded configuration. In the collapsed configuration, the radial force is absorbed by an intravascular microcatheter 3403 through which the retrieval device 3580 is delivered inside the artery. Each ring element 3582 comprises a plurality of struts 3583. Each strut 3583 has a crown element 3587. Each ring element 3582 is wrapped around the elongate member 3581 to restrain the retrieval device 3580 in the collapsed configuration when it is advanced through a microcatheter 3403. The microcatheter 3403 is advanced over a guidewire (not shown) inside a tortuous artery and positioned distal of an obstructive clot 3401. The microcatheter 3403 is retracted to allow each ring element 3582 to reach the expanded configuration and engage or capture the clot 3401 from the distal base of the clot (not shown) and then the device is retracted proximally into the microcatheter 3403.

FIGS. 53*a*-53*f* shows a method of using a mechanical clot retrieval device 3600 of the present invention in the embodiment as illustrated in FIGS. 52*a*-52*d*. A guide catheter 3601 is inserted inside the artery and a guidewire (not shown) is advanced within the catheter 3601 bypassing an occlusive clot (not shown). A microcatheter 3602 is advanced over the guidewire (not shown) to a location distal to the clot (not shown) and then the retrieval device 3600 is advanced through the microcatheter 3602 to the clot (not shown) in a collapsed configuration. The microcatheter 3602 is retracted to allow ring elements 3604 to reach an expanded configuration. The ring elements 3604 are self-expandable from the collapsed configuration to the expanded configuration and each ring element comprises plurality of struts 3605. Each strut 3605 has a crown element 3607. The ring elements 3604 are attached to the elongate member 3603 by connecting tethers 3606 and are wrapped around the elongate member 3603 to restrain the retrieval device 3600 in the collapsed configuration when it is advanced through the microcatheter 3602. The ring elements 3604, when expanded, engage or capture the clot (not shown) from the distal base of the clot (not shown) and retract the clot (not shown) proximally to the microcatheter 3602. The retrieval device 3600 returns to the collapsed configuration while retracting into the guide catheter 3601 and is easily removed from the artery.

FIGS. 54*a*-54*h* shows another method of using a mechanical clot retrieval device 3620 of the present invention in accordance with the embodiment as illustrated in FIGS. 52*a*-52*d*. A guidewire 3404 is inserted in a tortuous artery 3400 and advanced through an obstructive clot 3401. A microcatheter 3403 is advanced over the guidewire 3404 to a location distal to the clot 3401 and then the retrieval device 3620 is advanced through the microcatheter 3403 to the clot 3401 in a collapsed configuration. The microcatheter 3403 is retracted when the retrieval device 3620 is positioned distal of the clot 3401 to allow ring elements 3622 to reach an expanded configuration. The ring elements 3622 are self-expandable from the collapsed configuration to the expanded configuration and are wrapped around the elongate member 3621 to restrain the retrieval device 3620 in the collapsed configuration when advanced through the microcatheter 3403. A removal tether 3624 is attached to the retrieval device 3620. The ring elements 3622, when expanded using an activation element 3626, engage or capture the clot 3401 from the distal base of the clot 3401 and retract the clot 3401 proximally to the microcatheter 3603. The retrieval device 3620 returns to the collapsed configuration while retracting into a guide catheter 3627 and is easily removed from the artery 3400.

Another embodiment of a mechanical clot retrieval device of the present invention is represented in FIG. 55. The retrieval device 3700 has an elongate member 3701 having a distal end that extends interior of the artery and a proximal end that extends exterior of the artery, a plurality of ring elements 3702*a* having a larger diameter and a plurality of ring elements having a smaller diameter 3702*b*, and a control strut 3704 having distal end attached to proximal ring element 3702*a* and proximal end attached to the elongate member 3701 by adhesive bonds 3706. The ring elements 3702*a* and 3702*b* are self-expandable from a collapsed configuration to an expanded configuration and have a radial force that biases the ring elements 3702*a* and 3702*b* toward the expanded configuration. In the collapsed configuration, the radial force is absorbed by an intravascular microcatheter (not shown) through which the retrieval device 3700 is delivered inside the artery. Each ring element 3702*a*, and 3702*b* comprises a plurality of struts 3703. Each strut 3703 has a crown element 3707. The crown element 3707 is connected to neighboring crown element 3707 by the ring to ring connection 3705. The ring to ring connection 3705 restrains the retrieval device 3700 in the collapsed configuration when it is advanced through the microcatheter (not shown). The microcatheter is retracted proximally and each ring element 3702 disengages to form the expanded configuration.

Another embodiment of a mechanical clot retrieval device of the present invention is represented in FIG. 56. The retrieval device 3720 has an elongate member 3721 having a distal end that extends interior of the artery and a proximal end that extends exterior of the artery, a plurality of ring elements 3722, and a removal tether 3724 having distal end attached to proximal ring element 3722 and proximal end attached to the elongate member 3721. The ring elements 3722 are self-expandable from a collapsed configuration to an expanded configuration and have a radial force that biases the ring elements 3722 toward the expanded configuration. In the collapsed configuration, the radial force is absorbed by an intravascular microcatheter (not shown) through which the retrieval device 3720 is delivered inside the artery. Each ring element 3722 comprises a plurality of struts 3723. The outer mesh 3725 restrains the retrieval device 3720 and limits it to a certain diameter in the expanded configuration. The microcatheter is retracted proximally and each ring element 3722 disengages to form the maximum allowable diameter within the outer mesh.

Another embodiment of a mechanical clot retrieval device of the present invention is represented in FIG. 57. The retrieval device 3740 has an elongate member 3741 having a distal end that extends interior of the artery and a proximal end that extends exterior of the artery, a plurality of ring elements 3742, and a removal tether 3744 having distal end attached to proximal ring element 3742 and proximal end attached to the elongate member 3741. The ring elements 3742 are self-expandable from a collapsed configuration to an expanded configuration and have a radial force that biases the ring elements 3742 toward the expanded configuration. In the collapsed configuration, the radial force is absorbed by an intravascular microcatheter (not shown) through which the retrieval device 3740 is delivered inside the artery. Each ring element 3742 comprises a plurality of struts 3743. The tether net cover 3745 restrains the retrieval device 3740 and limits it to a certain diameter in the expanded configuration. The microcatheter is retracted proximally and each ring element 3742 disengages to form the maximum diameter allowed by the tether net cover.

Another embodiment of a mechanical clot retrieval device of the present invention is represented in FIG. 58. The retrieval device 3760 has an elongate member 3761 having a distal end that extends interior of the artery and a proximal end that extends exterior of the artery, a plurality of ring elements 3762, and a control strut 3764 having distal end attached to proximal ring element 3762 and proximal end attached to the elongate member 3761 by adhesive bonds 3766. The ring elements 3762 are self-expandable from a collapsed configuration to an expanded configuration and have a radial force that biases the ring elements 3762 toward the expanded configuration. In the collapsed configuration, the radial force is absorbed by an intravascular microcatheter (not shown) through which the retrieval device 3760 is delivered inside the artery. Each ring element 3762 comprises a plurality of struts 3763. Each strut 3763 has a crown element 3767. The crown element 3767 is connected to neighboring crown element 3767 by the ring to ring connection 3765. The ring to ring connection 3765 restrains the retrieval device 3760 in the collapsed configuration when it is advanced through the microcatheter (not shown). The microcatheter is retracted proximally and each ring element 3762 disengages to form the expanded configuration.

Another embodiment of a mechanical clot retrieval device of the present invention is represented in FIG. 59. The retrieval device 3780 has an elongate member 3781 having a distal end that extends interior of the artery and a proximal end that extends exterior of the artery, a plurality of ring elements 3782, and a removal tether 3784 having distal end attached to proximal ring element 3782 and proximal end attached to the elongate member 3781. The ring elements 3782 are self-expandable from a collapsed configuration to an expanded configuration and have a radial force that biases the ring elements 3782 toward the expanded configuration. In the collapsed configuration, the radial force is absorbed by an intravascular microcatheter (not shown) through which the retrieval device 3780 is delivered inside the artery. Each ring element 3782 comprises a plurality of struts 3783. The tether net cover 3785 restrains the retrieval device 3780 and limits it to a certain diameter in the expanded configuration. The device also comprises a tapered ring element at the distal end of the tether net cover 3785. The microcatheter is retracted proximally and each ring element 3782 disengages to form the maximum diameter allowed by the tether net cover 3785.

Another embodiment of a mechanical clot retrieval device of the present invention is represented in FIG. 60. The retrieval device 3800 has an elongate member 3801 having a distal end that extends interior of the artery and a proximal end that extends exterior of the artery, a plurality of ring elements 3802, and a control strut 3804 having distal end attached to proximal ring element 3802 and proximal end attached to the elongate member 3801 by adhesive bonds 3806. The ring elements 3802 are self-expandable from a collapsed configuration to an expanded configuration and have a radial force that biases the ring elements 3802 toward the expanded configuration. In the collapsed configuration, the radial force is absorbed by an intravascular microcatheter (not shown) through which the retrieval device 3780 is delivered inside the artery. Each ring element 3802 comprises a plurality of struts 3803. Each strut 3803 has a crown element 3807. The crown element 3807 is connected to neighboring crown element 3807 by the ring to ring connection 3805. The ring to ring connection 3805 restrains the retrieval device 3800 in the collapsed configuration when it is advanced through the microcatheter (not shown). The ring elements are wrapped in an outer mesh/net cover 3808 which limits the diameter of the ring elements in the expanded configuration. The microcatheter is retracted proximally and each ring element 3802 disengages to form the expanded configuration with the maximum diameter allowed by the outer mesh/net cover 3808.

Another preferred embodiment of a mechanical clot retrieval device 3820 of the present invention is illustrated in FIGS. 61a-61c. The retrieval device 3820 is advanced through a microcatheter 3821 inside the patient artery and includes an activation tether 3824, having a distal end that extends interior of the artery and a proximal end that extends exterior of the artery, a distal collar 3827, and a plurality of ring elements 3822 configured to the distal end of the activation tether 3824. The ring elements 3822 are self-expandable from a collapsed configuration to an expanded configuration and have a radial force that biases the ring elements 3822 in the expanded configuration. In the collapsed configuration, the radial force is absorbed by an intravascular microcatheter 3821 through which the retrieval device 3820 is delivered inside the artery. Each ring element 3822, comprising a plurality of struts 3823, is interconnected by bridges 3825. The microcatheter 3821 is retracted and the activation tether 3824 is manually pulled proximally to compress the device and allow ring elements 3822 to reach the expanded configuration.

FIGS. 62a-62b shows a mechanical clot retrieval device 3840 of the present invention which is a slightly variant embodiment of the retrieval device as illustrated in FIGS. 61a-61c. The retrieval device 3840 is advanced through a microcatheter 3841 inside the artery and has an activation tether 3844, having a distal end that extends interior of the artery and a proximal end that extends exterior of the artery, a distal collar 3847, and a ring element 3846 configured at the distal end of the activation tether 3844. The ring element 3846 is self-expandable from a collapsed configuration to an expanded configuration and comprises a radial force that biases the ring element 3846 to the expanded configuration. The ring element comprises a plurality of struts 3843. The microcatheter 3841 is retracted and the activation tether 3844 is manually pulled proximally to compress the device proximally and allow ring elements 3842 to reach the expanded configuration.

FIGS. 63a-63b shows a mechanical clot retrieval device 3860 of the present invention which is a slightly variant embodiment of the retrieval device 3840 as illustrated in FIGS. 62a-62b. The retrieval device 3862 is advanced through a microcatheter 3861 inside the artery and has an activation tether 3864 having a distal end that extends interior of the artery and a proximal end that extends exterior of the artery, a distal collar 3867, a ring element 3866 configured at the distal end of the activation tether 3864, and a pair of removal tethers 3862 attached to the ring element 3866 having proximal ends that extend out of the artery. The ring element 3866 is self-expandable from a collapsed configuration to an expanded configuration and comprises a radial force that biases the ring element 3866 to the expanded configuration. In the collapsed configuration, the radial force is absorbed by the microcatheter. The microcatheter 3861 is retracted and the activation tether 3864 is manually pulled proximally to compress the device proximally and allow ring element 3866 to reach the expanded configuration.

FIGS. 64a-64b shows a mechanical clot retrieval device 3880 of the present invention which is a slightly variant embodiment of the retrieval device 3860 as illustrated in FIGS. 63a-63b. The retrieval device 3882 is advanced through a microcatheter 3881 inside the patient artery and has an activation tether 3884 having a distal end that extends interior of the artery and a proximal end that extends exterior of the artery, a couple of collars 3887, a couple of ring elements 3886 configured at the distal end of the activation tether 3884, and a pair of removal tethers 3882 having distal ends attached to the ring element 3886 and having proximal attached to the collar 3887. The ring element 3886 is self-expandable from a collapsed configuration to an expanded configuration and has a radial force that biases the ring element 3886 to the expanded configuration. In the collapsed configuration, the radial force is absorbed by the microcatheter 3881. Each ring element 3886 comprises a plurality of struts 3883. The microcatheter 3881 is retracted and the activation tether 3884 is manually pulled proximally to compress the device and to allow ring element 3886 reach the expanded configuration.

FIGS. 65a-65d illustrates another preferred embodiment of a mechanical clot retrieval device 3900a of the present invention. The retrieval device 3900a is advanced through a microcatheter 3901 inside the patient artery and has a pair of activation tethers 3904 having distal ends that extend interior of the artery and proximal ends that extend exterior of the artery, a distal collar 3907, and a plurality of ring elements 3902 configured to the distal end of the activation tether 3904. The ring elements 3902 are self-expandable from a collapsed configuration 3900a to an expanded configuration 3900b and have a radial force that biases the ring elements 3902 to the expanded configuration 3900b. In the collapsed configuration, the radial force is absorbed by an intravascular microcatheter 3901 through which the retrieval device 3900a is delivered inside the artery. Each ring element 3902, comprising a plurality of struts 3903, is connected by bridges 3905. Each strut includes a tether guide tube 3908. The distal end of activation tether is passed through the guide tube 3908. The microcatheter 3901 is retracted and the activation tethers 3904 are manually pulled proximally to compress the device proximally and to allow ring elements 3902 to reach the expanded configuration 3900b.

FIGS. 66a-66c illustrates a mechanical clot retrieval device 3920a of the present invention which is a slightly variant embodiment of the retrieval device shown in FIGS. 61a-61c. The retrieval device 3920a is advanced through a microcatheter 3921 inside the patient artery and has a pair of activation tethers 3924 having distal ends that extend interior of the artery and proximal ends that extend exterior of the artery, a distal collar 3927, and a plurality of ring elements 3922 configured to the distal end of the activation tether 3824. The ring elements 3922 are self-expandable from a collapsed configuration 3920a to an expanded configuration 3920b and comprise a radial force that biases the ring elements 3922 in the expanded configuration 3920b. In the collapsed configuration, the radial force is absorbed by an intravascular microcatheter 3921 through which the retrieval device 3920a is delivered inside the artery. Each ring element 3922 comprising a plurality of struts 3923 and a limiting tether 3928 is interconnected by bridges 3925. The microcatheter 3921 is retracted and the activation tether 3924 is manually pulled proximally to compress the device and to allow ring elements 3922 to reach the expanded configuration 3920b. The limiting tether 3928 prevents the ring element from expanding beyond a certain diameter.

FIGS. 67a-67b shows a mechanical clot retrieval device 3940 of the present invention which is a slightly variant embodiment of the retrieval device 3840 as illustrated in FIGS. 62a-62b. The retrieval device 3940 is advanced through a microcatheter 3941 inside the patient artery and has an activation tether 3944 having a distal end that extends interior of the artery and a proximal end that extends exterior of the artery, a distal collar 3947, and a ring element 3946 configured at the distal end of the activation tether 3944. The ring element 3946 is self-expandable from a collapsed configuration to an expanded configuration and has a radial force that biases the ring element 3946 to the expanded configuration. The ring element comprising a plurality of struts 3943 and a limiting tether 3948. The microcatheter 3941 is retracted and the activation tether 3944 is manually pulled proximally to compress the device and to allow ring elements 3942 to reach the expanded configuration.

FIGS. 68a-68b shows a mechanical clot retrieval device 3960 of the present invention which is a slightly variant embodiment of the retrieval device 3860 as illustrated in FIGS. 63a-63b. The retrieval device 3962 is advanced through a microcatheter 3961 inside the artery and has an activation tether 3964 having a distal end that extends interior of the artery and a proximal end that extends exterior of the artery, a distal collar 3967, a ring element 3966 configured at the distal end of the activation tether 3964, and a pair of removal tethers 3962 attached to the ring element 3966 having proximal ends that extend exterior of the artery. The ring element 3966 is self-expandable from a collapsed configuration to an expanded configuration and has a radial force that biases the ring element 3966 to the expanded configuration. In the collapsed configuration, the radial force is absorbed by the microcatheter 3961. Each ring element 3966 comprises a plurality of struts 3963 and a limiting tether 3968. The microcatheter 3961 is retracted and the activation tether 3964 is manually pulled proximally to compress the device and allow ring elements 3966 to reach the expanded configuration.

FIGS. 69a-69b shows a mechanical clot retrieval device 3980 of the present invention which is a slightly variant embodiment of the retrieval device 3880 as illustrated in FIGS. 64a-64b. The retrieval device 3980 is advanced through a microcatheter 3981 inside the artery and has an activation tether 3984 having a distal end that extends interior of the artery and a proximal end that extends exterior of the artery, a couple of collars 3987, a couple of ring elements 3986 configured at the distal end of the activation tether 3984, and a pair of removal tethers 3982 having distal ends attached to the ring element 3986. The ring element 3986 is self-expandable from a collapsed configuration to an expanded configuration and has a radial force that biases the ring element 3986 to the expanded configuration. In the collapsed configuration, the radial force is absorbed by the microcatheter 3981. Each ring element comprises a plurality of struts 3983 and a limiting tether 3988. The microcatheter 3981 is retracted and the activation tether 3984 is manually pulled proximally to compress the device and allow the ring elements 3986 reach the expanded configuration.

The ring elements used in the above description are made of shape-memory material, preferably Nitinol. Remaining elements of the retrieval device as described herein are preferably formed of a material such as a stainless steel, a nickel-based super alloy, a spring steel alloy, particularly a composition sold under the trademark nitinol.

It will be apparent from the foregoing description that, while particular embodiments of the present invention have been illustrated and described, various modifications can be made without departing from the spirit and scope of the invention.

Modifications and additions can be made to the various embodiments of the invention described herein. For example, while embodiments may refer to particular features, the invention includes embodiments having different combinations of features. The invention also includes embodiments that do not include all of the specific features described.

The invention is not limited to the embodiments hereinbefore described which may be varied in construction and detail.

What is claimed is:

1. A clot retrieval device for removing a clot from a blood vessel, comprising:
   a plurality of ring elements comprising:
   one or more distal apices;
   one or more proximal apices offset from the one or more distal apices; and
   a plurality of struts forming one or more closed cells having one or more crown elements,
   wherein the plurality of ring elements are attached together by connecting tethers at connection points including at at least the one or more proximal apices; and
   a plurality of openings through which the clot may pass and enter the device, each opening being disposed between respective ring elements;
   wherein each ring element being self-expandable from a collapsed configuration to an expanded configuration wherein a radial force biases the ring elements toward the expanded configuration; and
   wherein at least one of the crown elements terminates in an apex away from a center axis of the device.

2. The device of claim 1, wherein adjacent struts of the plurality of struts of each of the plurality of ring elements couple to one another in the collapsed configuration and uncouple from one another in the expanded configuration.

3. The device of claim 1, wherein in the expanded configuration, a distal end of at least one end of the ring elements extends radially outwardly.

4. The device of claim 1, wherein the one or more distal apices and the one or more proximal apices are offset from each other in a sinusoidal configuration.

5. A clot retrieval device comprising:
   a plurality of clot engaging ring elements, the plurality of clot engaging ring elements comprising distal apices, proximal apices offset from the distal apices, and struts connected between respective distal and proximal apices of respective clot engaging ring elements, each clot engaging ring element being expandable between a retracted delivery configuration and an expanded deployed configuration,
   wherein the plurality of clot engaging ring elements are attached together by connecting tethers at connection points including at at least the proximal apices, and
   wherein to move to the expanded deployed configuration from the retracted delivery configuration, a shaft is axially translated thereby applying a radial force that biases the plurality of clot engaging ring elements to expand to the expanded deployed configuration.

6. The device of claim 5, further comprising:
   the shaft extending between a proximal end and a distal end, the clot engaging ring elements being connected to the distal end of the shaft.

7. The device of claim 5, wherein respective struts of respective clot engaging ring elements are connected through the connecting tethers.

8. The device of claim 5, wherein each of the clot engaging ring elements comprise a collar and an interior circumferential surface.

9. The device of claim 5, wherein each of the plurality of clot engaging ring elements is connected to at least one other of the plurality of clot engaging ring elements.

10. The device of claim 5, wherein in the expanded deployed configuration, a clot inlet opening is defined between the distal side of a first clot engaging ring element and a second adjacent clot engaging ring element.

11. The device of claim 5, wherein adjacent struts of the struts of each of the plurality of clot engaging ring elements couple to one another in the retracted delivery configuration and uncouple from one another in the expanded deployed configuration.

12. The device of claim 11, wherein connectors of the adjacent struts of the struts of each of the plurality of clot engaging ring elements include hooks.

13. The device of claim 5, wherein, in a partially deployed configuration, a distal end of at least one of the plurality of clot engaging ring elements tapers radially outwardly.

14. The device of claim 13, further including a tube, wherein the shaft is axially translatable within a lumen of the tube.

15. The device of claim 14, wherein the tube includes a proximal collar.

16. A clot retrieval device comprising:
   a shaft extending between a proximal end and a distal end;
   at least three clot engaging ring elements, the clot engaging ring elements comprising one or more distal apices, one or more proximal apices offset from the one or more distal apices, and struts connected through one or more connectors, each clot engaging ring element being expandable between a retracted delivery configuration and an expanded deployed configuration,
   wherein the at least three clot engaging ring elements are attached together by connecting tethers at connection points including at at least the one or more proximal apices,
   wherein in the retracted delivery configuration, the at least three clot engaging ring elements are configured to radially surround the shaft; and
   wherein to move to the expanded deployed configuration from the retracted delivery configuration, the shaft is axially translated thereby biasing the at least three clot engaging ring elements to expand to the expanded deployed configuration.

17. The device of claim 16, wherein the connecting tethers are disposed between a distal side of a first clot engaging ring element of the at least three clot engaging ring elements, and a proximal side of a second adjacent clot engaging ring element of the at least three clot engaging ring elements.

18. The device of claim 16, wherein in the expanded deployed configuration, a clot inlet opening is defined between each adjacent clot engaging ring element.

19. The device of claim 16, wherein the clot engaging ring elements comprise one or more crown elements that terminate in an apex away from a center axis of the device, wherein in the expanded deployed configuration, a clot inlet opening for receiving a clot is defined between distal and proximal sides of each adjacent clot engaging ring element.

20. The device of claim 16, wherein adjacent struts of the struts of each of the at least three clot engaging ring elements couple to one another in the retracted delivery configuration and uncouple from one another in the expanded deployed configuration.

21. The device of claim 16, further including a microcatheter, wherein the shaft is axially translatable within a lumen of the microcatheter.

22. The device of claim 16, wherein one or more tethers are connected to the shaft.

* * * * *